United States Patent [19]
Beyar et al.

[11] Patent Number: 6,127,597
[45] Date of Patent: Oct. 3, 2000

[54] SYSTEMS FOR PERCUTANEOUS BONE AND SPINAL STABILIZATION, FIXATION AND REPAIR

[75] Inventors: Mordechay Beyar, Caesarea; Oren Globerman; Elad Magal, both of Herzelia, all of Israel

[73] Assignee: DiscoTech N.V., Herzelia, Israel

[21] Appl. No.: 09/036,719

[22] Filed: Mar. 6, 1998

Related U.S. Application Data

[60] Provisional application No. 60/038,942, Mar. 7, 1997, provisional application No. 60/038,618, Mar. 7, 1997, and provisional application No. 60/071,531, Jan. 15, 1998.

[51] Int. Cl.$^7$ ............................................. A61F 5/04
[52] U.S. Cl. ................................................. 623/16; 623/11
[58] Field of Search .................................. 623/11, 16, 20

[56] References Cited

U.S. PATENT DOCUMENTS

| | | |
|---|---|---|
| 3,426,364 | 2/1969 | Lumb . |
| 4,170,990 | 10/1979 | Baumgart et al. . |
| 4,204,531 | 5/1980 | Aginsky . |
| 4,309,777 | 1/1982 | Patil . |
| 4,313,434 | 2/1982 | Segal . |
| 4,349,921 | 9/1982 | Kuntz . |
| 4,453,539 | 6/1984 | Raftopoulos et al. . |
| 4,522,200 | 6/1985 | Stednitz . |
| 4,554,914 | 11/1985 | Kapp et al. . |
| 4,558,693 | 12/1985 | Lash .......................................... 623/11 |
| 4,636,217 | 1/1987 | Ogilvie et al. . |
| 4,686,973 | 8/1987 | Frisch . |
| 4,697,584 | 10/1987 | Haynes . |
| 4,759,769 | 7/1988 | Hedman et al. . |
| 4,772,287 | 9/1988 | Ray et al. . |
| 4,854,312 | 8/1989 | Raftopoulos et al. . |
| 4,904,260 | 2/1990 | Ray et al. . |
| 4,932,969 | 6/1990 | Frey et al. . |
| 5,059,193 | 10/1991 | Kuslich . |
| 5,102,413 | 4/1992 | Poddar . |

(List continued on next page.)

FOREIGN PATENT DOCUMENTS

| | | |
|---|---|---|
| 0748615 A1 | of 0000 | European Pat. Off. . |
| 2629337 | of 0000 | France . |
| 2674119 | of 0000 | France . |
| 2821785 | of 0000 | Germany . |
| 293-485 | of 0000 | Germany . |
| 1011-119 | of 0000 | U.S.S.R. . |
| 662-082 | of 0000 | U.S.S.R. . |
| 2114005 | of 0000 | United Kingdom . |
| 2268068 | of 0000 | United Kingdom . |
| WO 9000037 | of 0000 | WIPO . |
| WO 9214423 | of 0000 | WIPO . |
| WO 94/12112 | of 0000 | WIPO . |
| WO 96/32899 | of 0000 | WIPO . |
| WO 9611643 | of 0000 | WIPO . |
| WO 9637170 | of 0000 | WIPO . |

OTHER PUBLICATIONS

Closed Intramedullary Pinning of Metacarpal and Phalanx Fractures, by Charles D. Varela, M.D. and James B. Carr, M.D. pp. 213–214, Orthopedics, Feb. 1990.

AIM Titanium Humeral Nail System by J. Dean Cole, M.D. in collaboration with Professor Dr. Harald Hertz, Surgical Technique, Ace Medical Company.

*Primary Examiner*—Paul J. Hirsch
*Attorney, Agent, or Firm*—Levisohn, Lerner, Berger & Langsam

[57] ABSTRACT

Systems for bone and spinal stabilization, fixation and repair include intramedullar nails, intervertebral cages and prostheses, remotely activatable prostheses, tissue extraction devices, and electrocautery probes. The intramedullar nails, intervertebral cages and prostheses, are designed for expansion from a small diameter for insertion into place to a larger diameter which stabilizes, fixates or repairs the bone, and further can be inserted percutaneously. Remotely activatable prostheses can be activated from an external unit to expand and treat prosthesis loosening. Tissue extraction devices, and electrocautery probes are used to remove tissue from desired areas.

27 Claims, 35 Drawing Sheets

U.S. PATENT DOCUMENTS

| | | |
|---|---|---|
| 5,108,404 | 4/1992 | Scholten et al. . |
| 5,122,400 | 6/1992 | Stewart . |
| 5,131,382 | 7/1992 | Meyer . |
| 5,171,278 | 12/1992 | Pisharodi . |
| 5,303,718 | 4/1994 | Krajicek . |
| 5,376,123 | 12/1994 | Klaue et al. . |
| 5,423,850 | 6/1995 | Berger . |
| 5,480,400 | 1/1996 | Berger . |
| 5,520,690 | 5/1996 | Errico et al. . |
| 5,522,816 | 6/1996 | Dinello et al. . |
| 5,522,899 | 6/1996 | Michelson . |
| 5,571,189 | 11/1996 | Kuslich . |
| 5,645,598 | 7/1997 | Brosnahan, III . |
| 5,658,310 | 8/1997 | Berger . |
| 5,704,895 | 1/1998 | Scott et al. .............................. 623/11 |
| 5,827,289 | 10/1998 | Reiley et al. . |

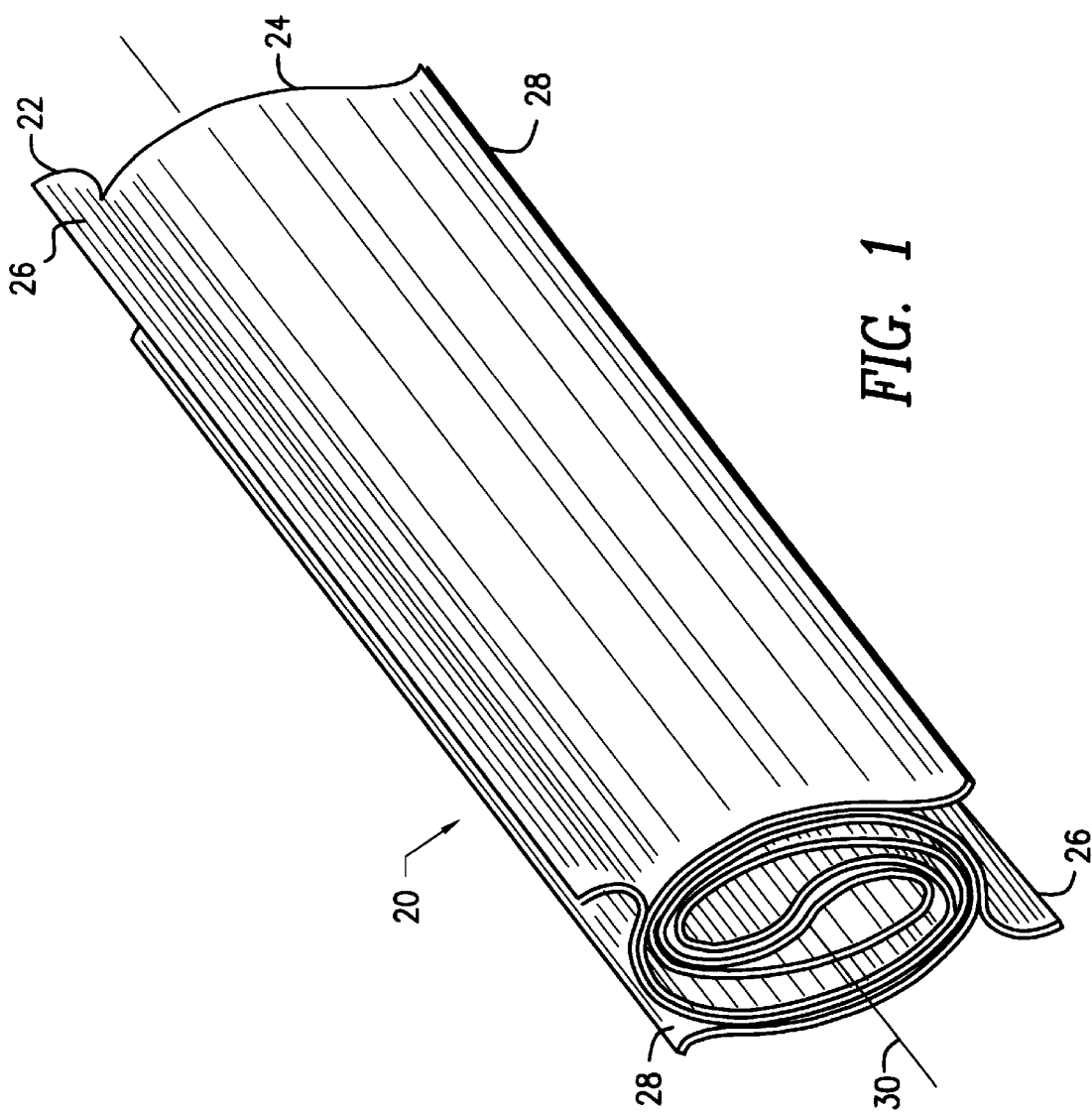
FIG. 1

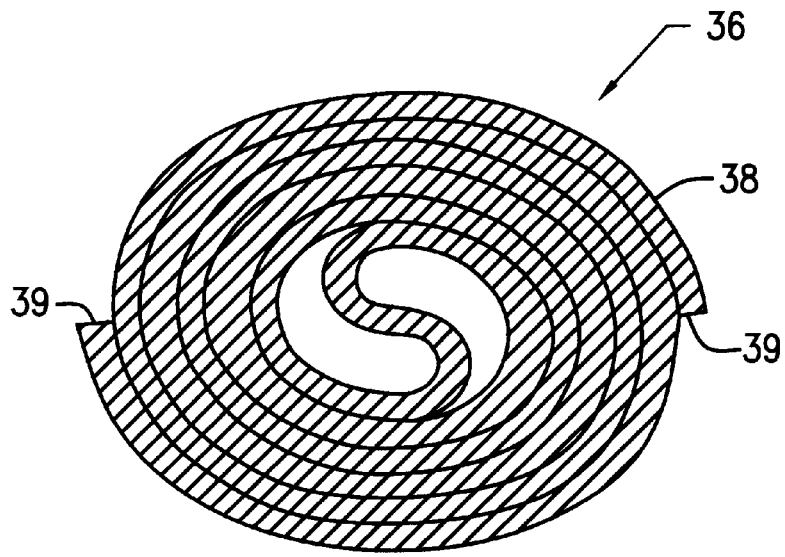
*FIG. 2A*
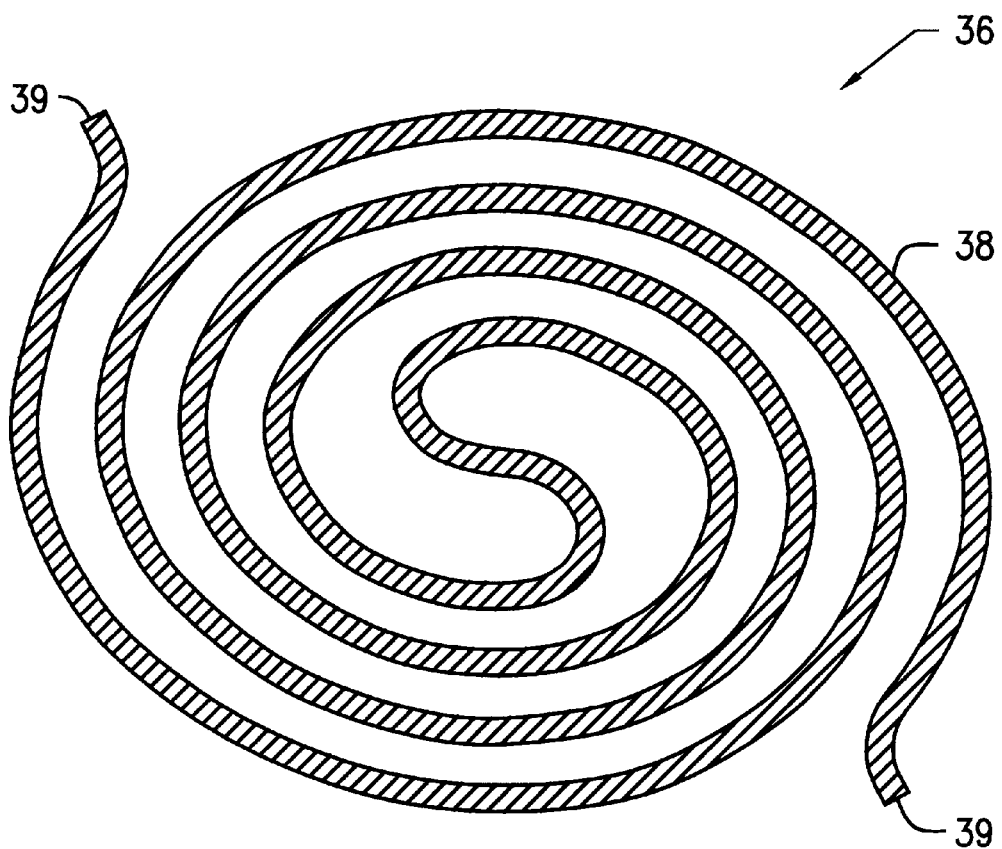
*FIG. 2B*

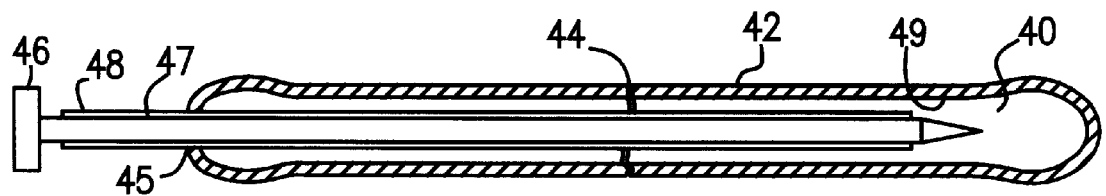
FIG. 3A
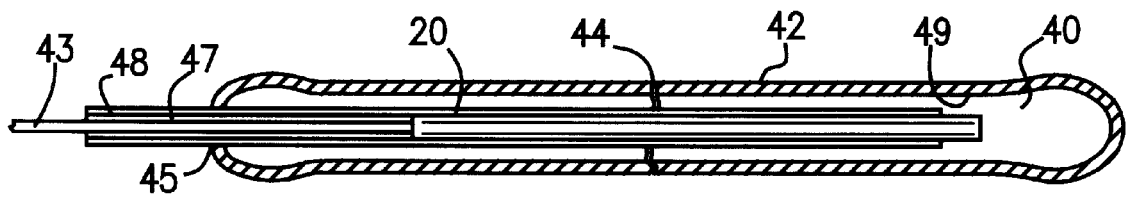
FIG. 3B
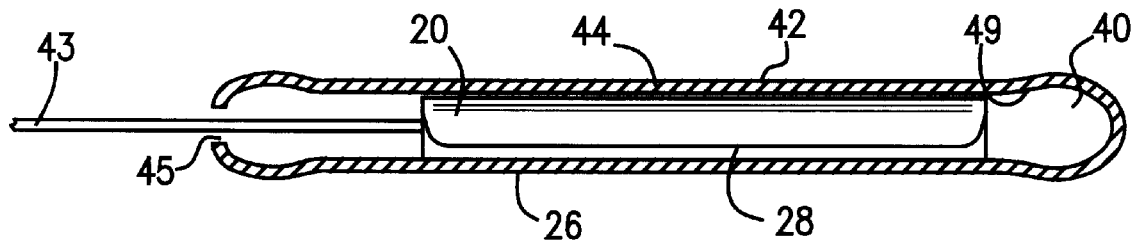
FIG. 3C

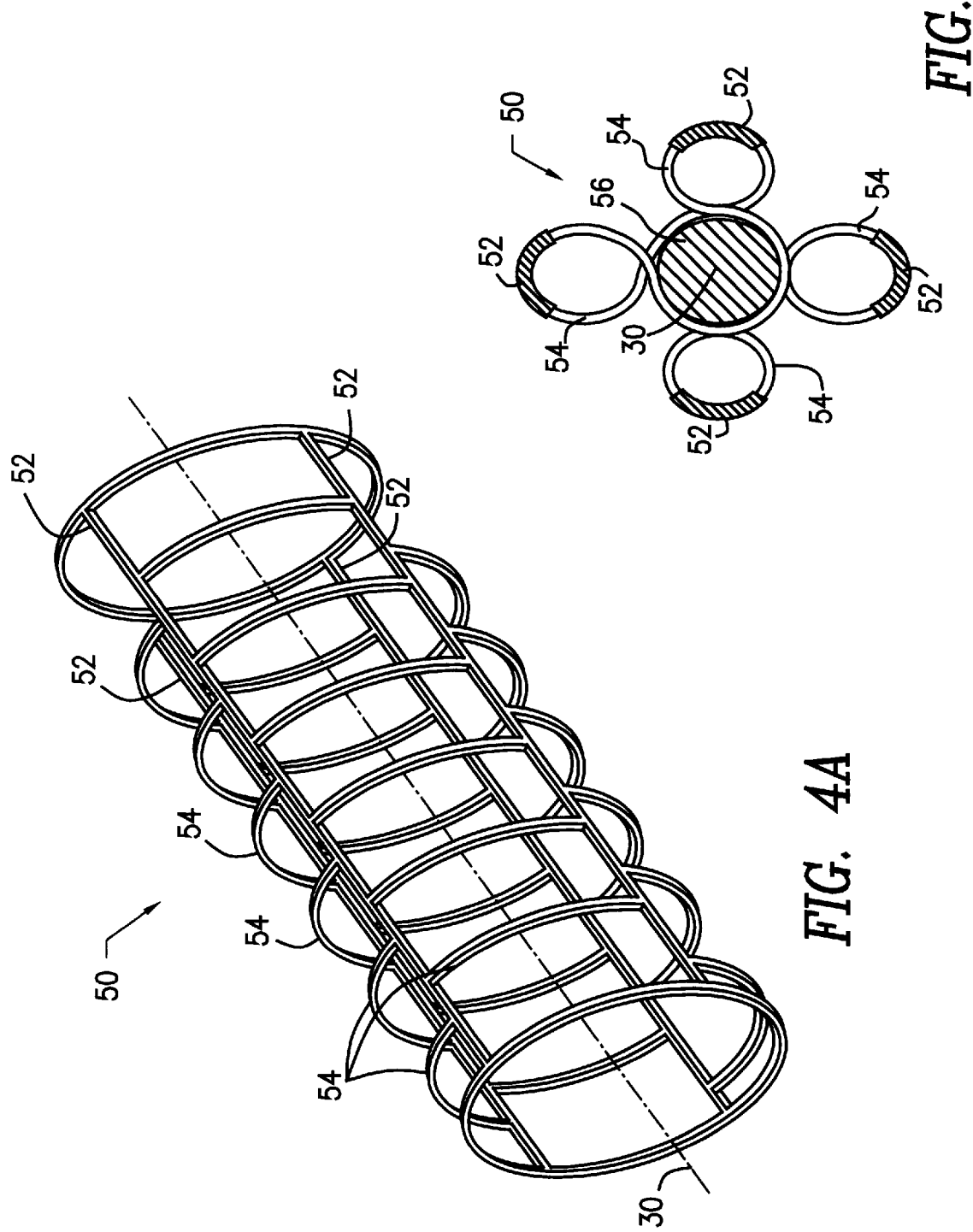

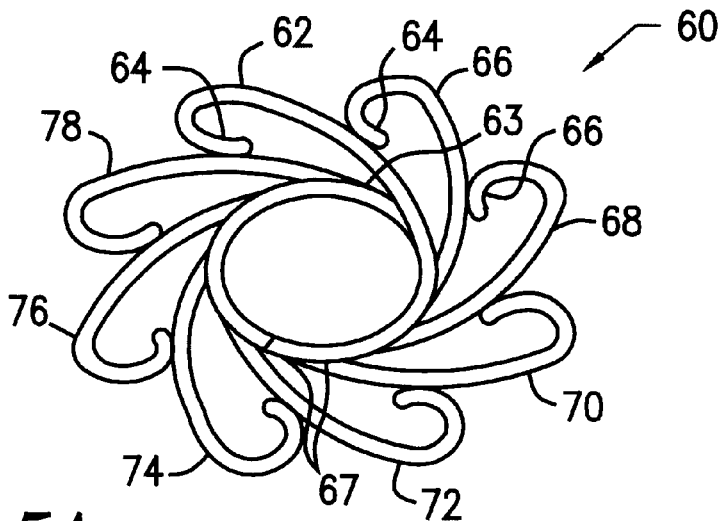
FIG. 5A
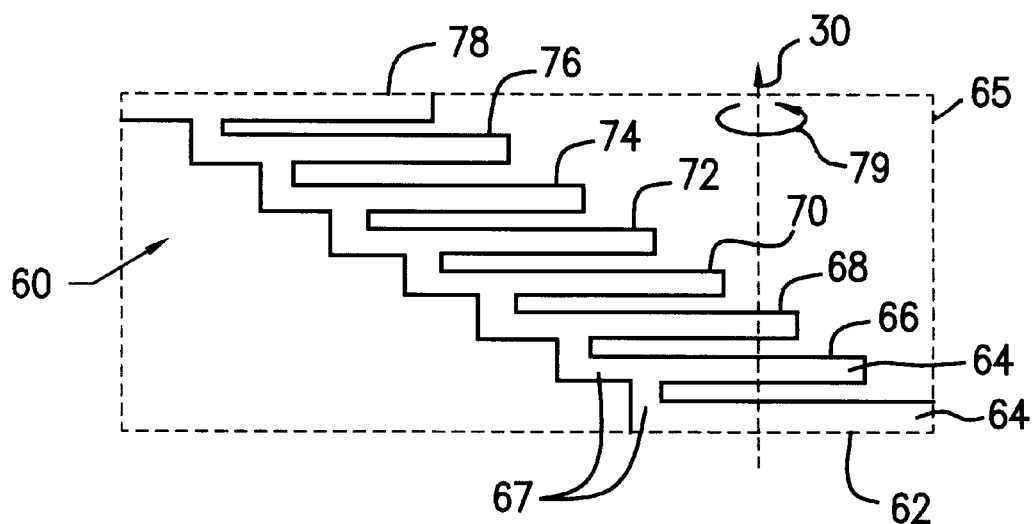
FIG. 5B
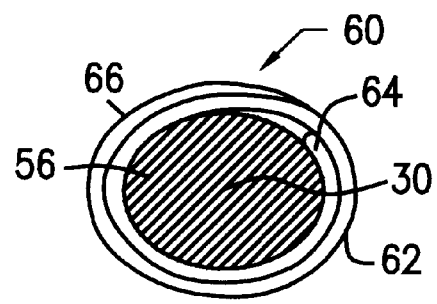
FIG. 5C

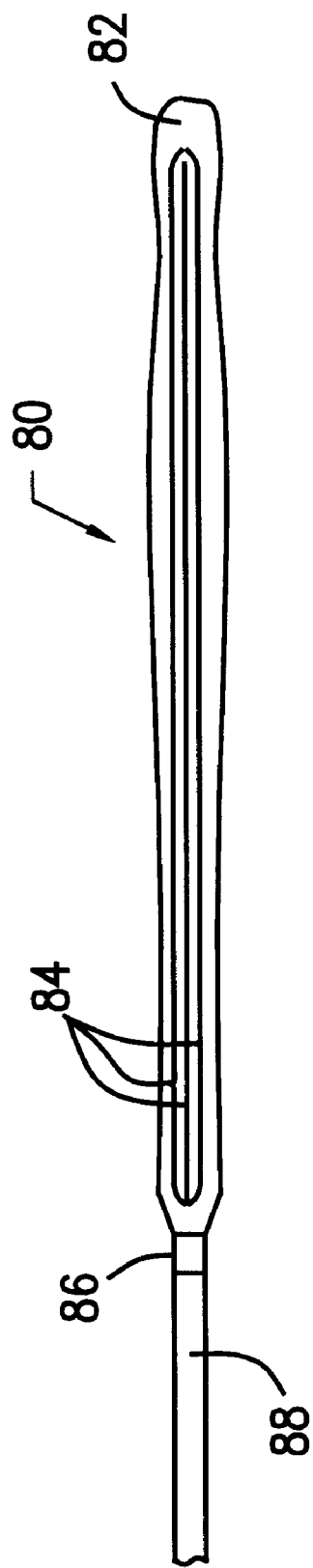
FIG. 6

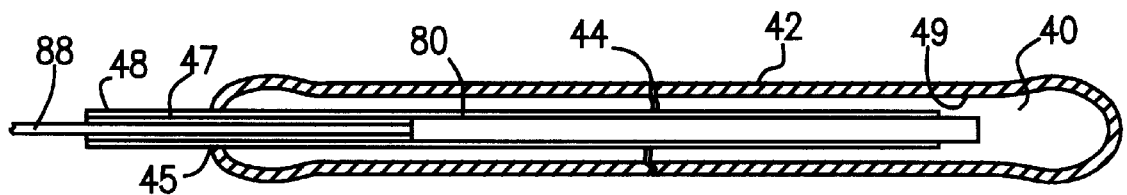
FIG. 7A
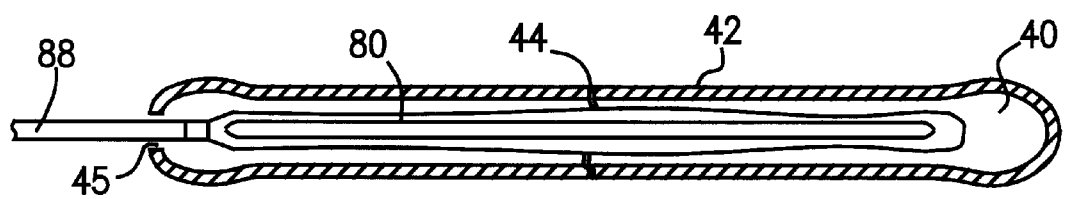
FIG. 7B
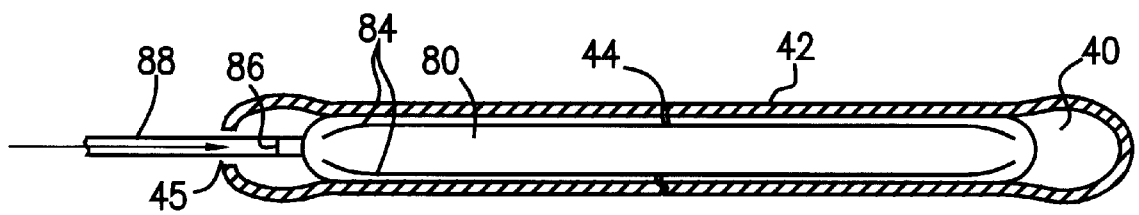
FIG. 7C
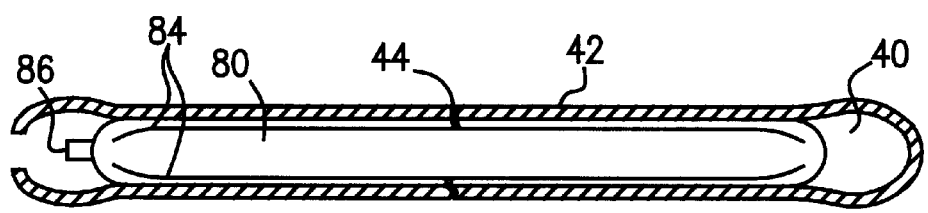
FIG. 7D

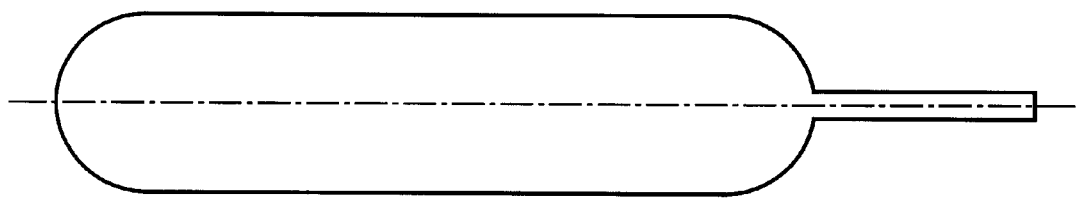
FIG. 8A
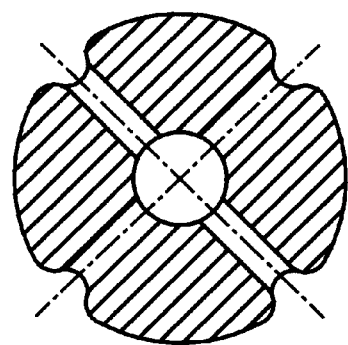
FIG. 8B

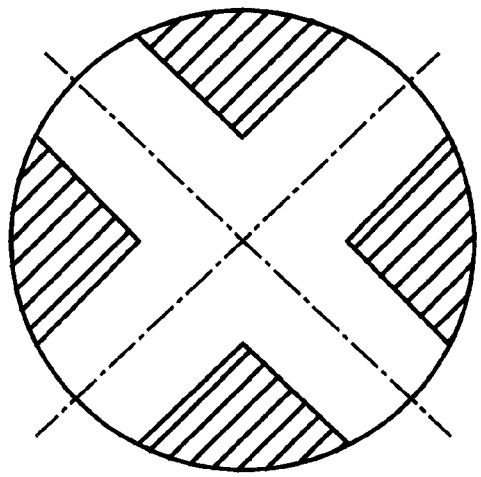
FIG. 9A
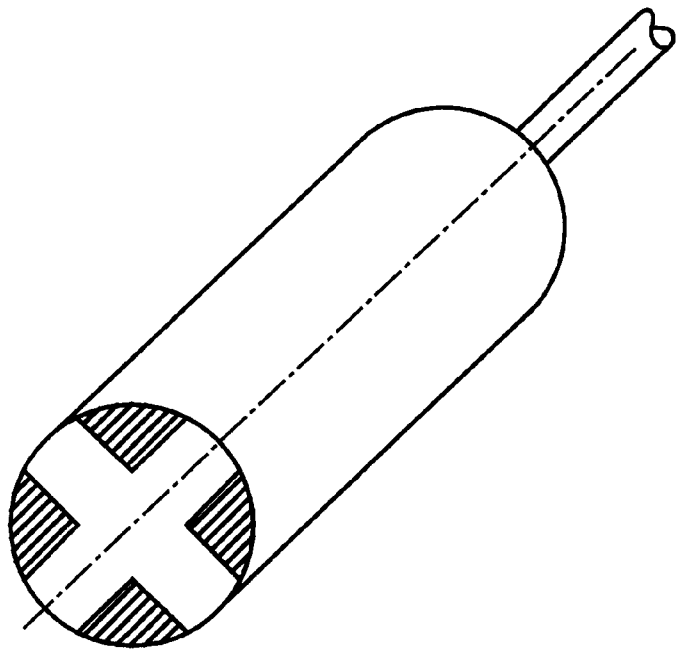
FIG. 9B

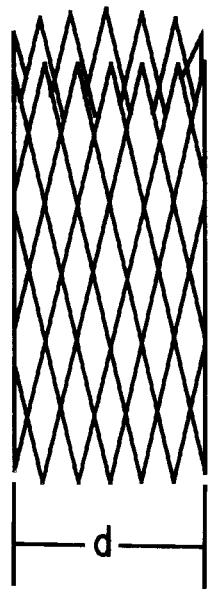
FIG. 10A
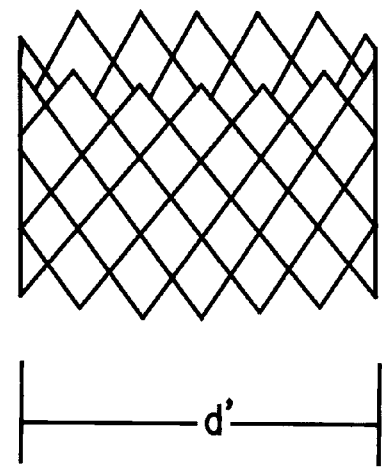
FIG. 10B
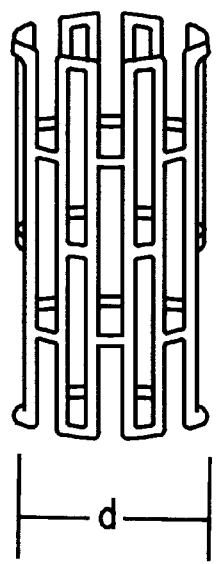
FIG. 10C
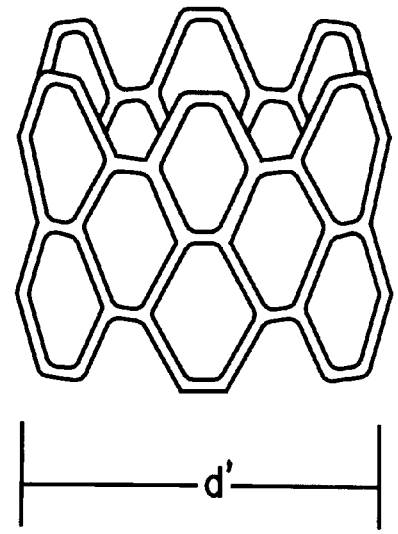
FIG. 10D

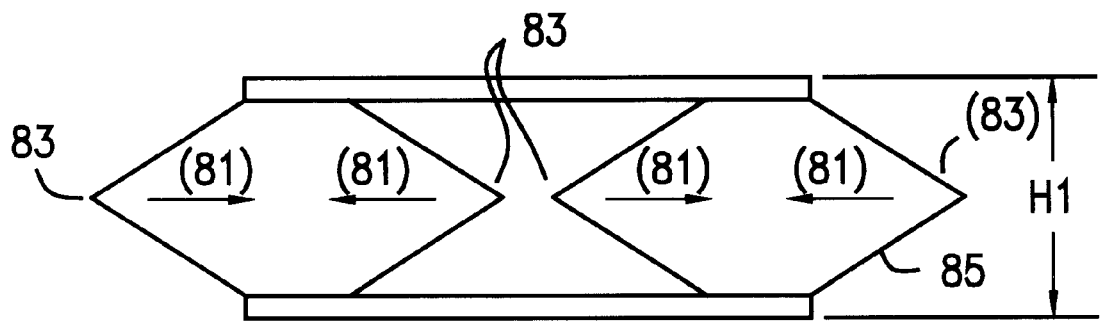
*FIG. 11A*
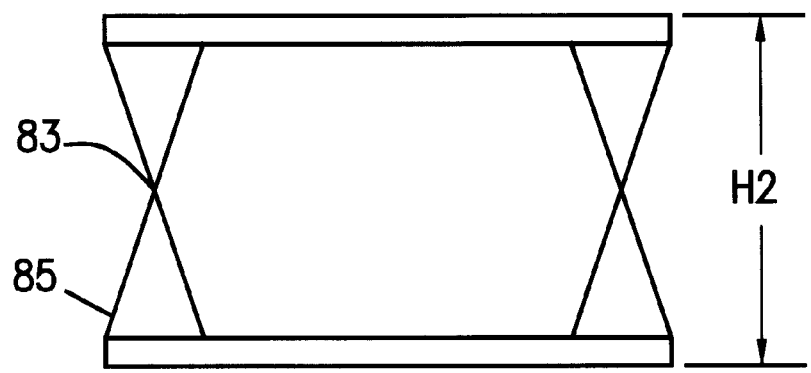
*FIG. 11B*

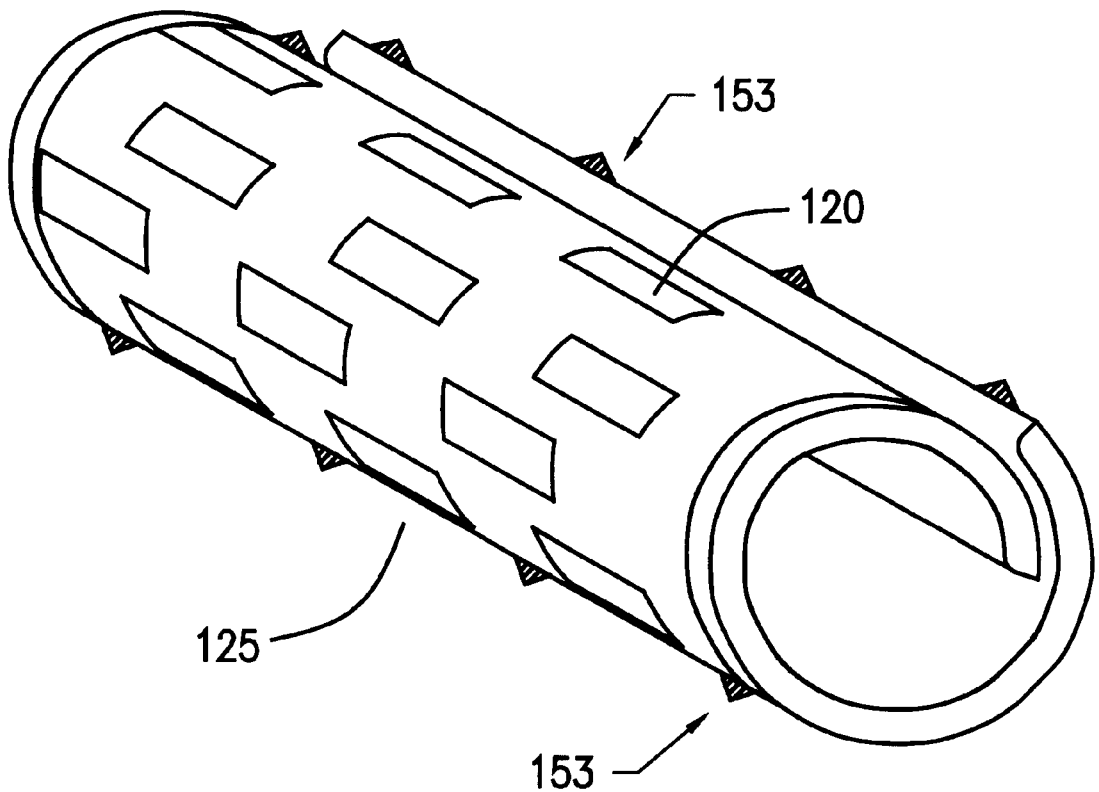
FIG. 12

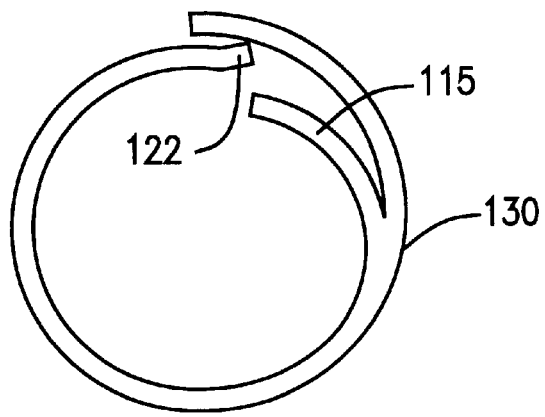
FIG. 13A
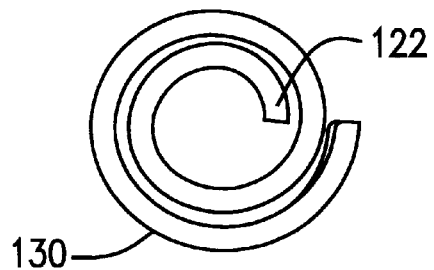
FIG. 13B
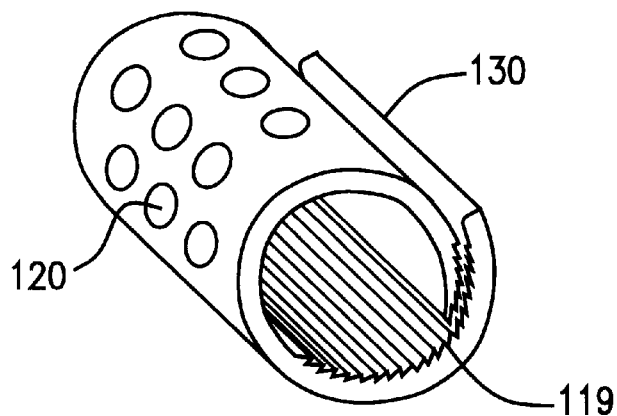
FIG. 13C

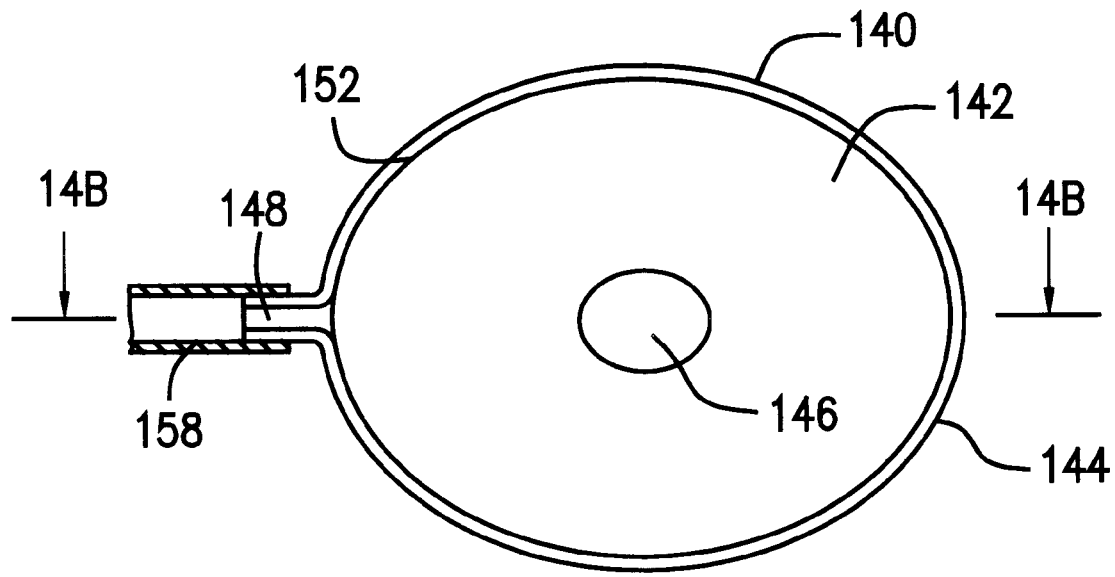
FIG. 14A
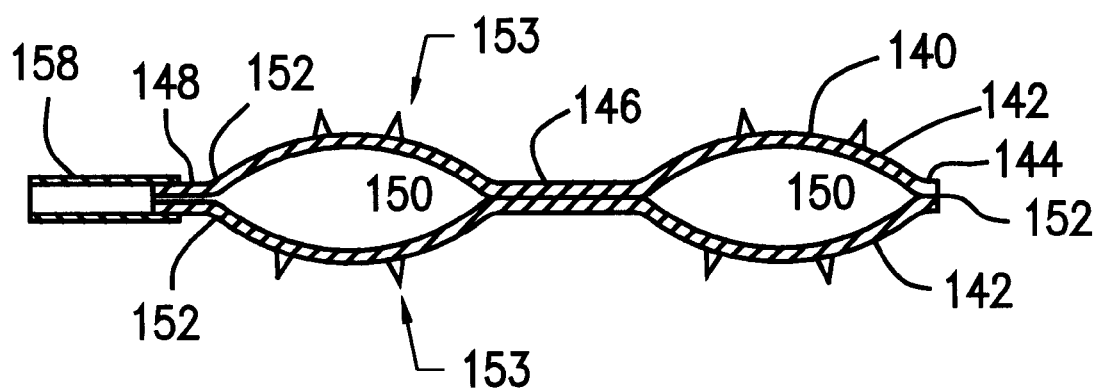
FIG. 14B

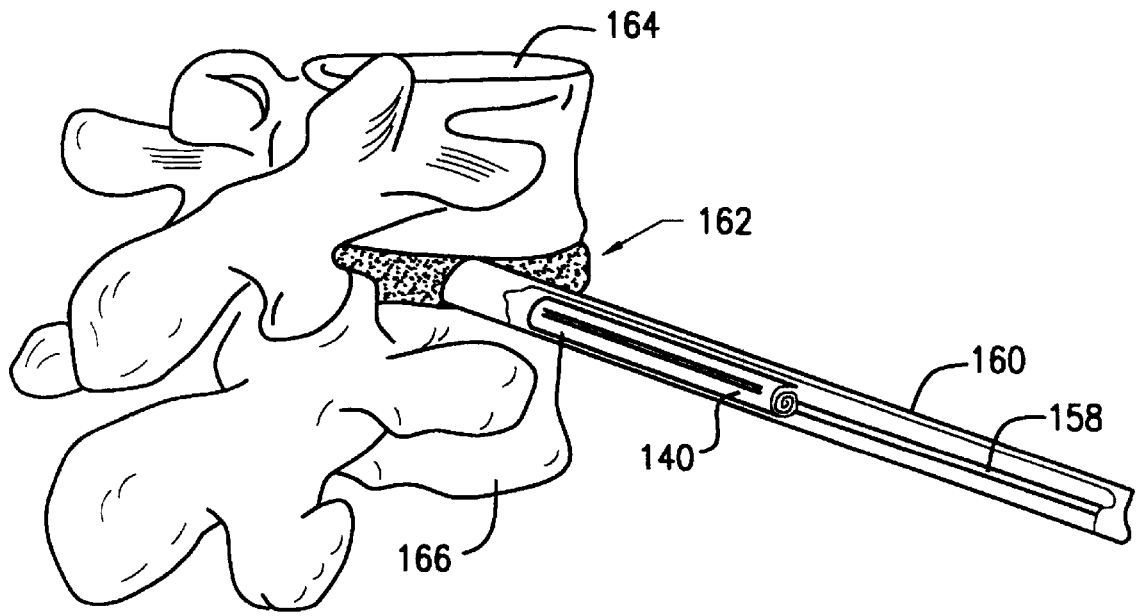
FIG. 15
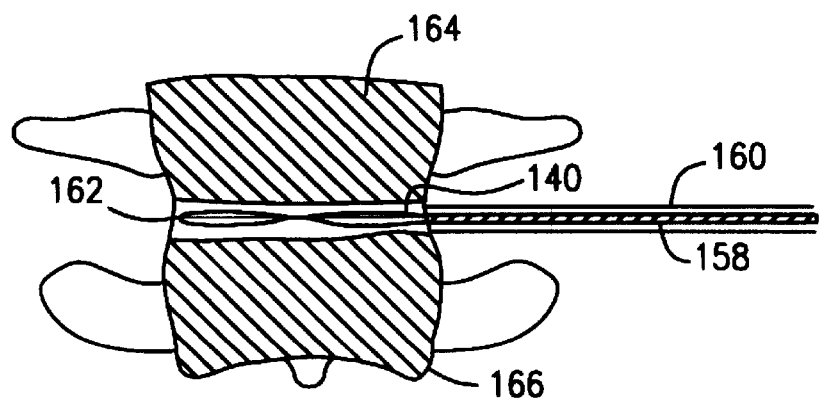
FIG. 16

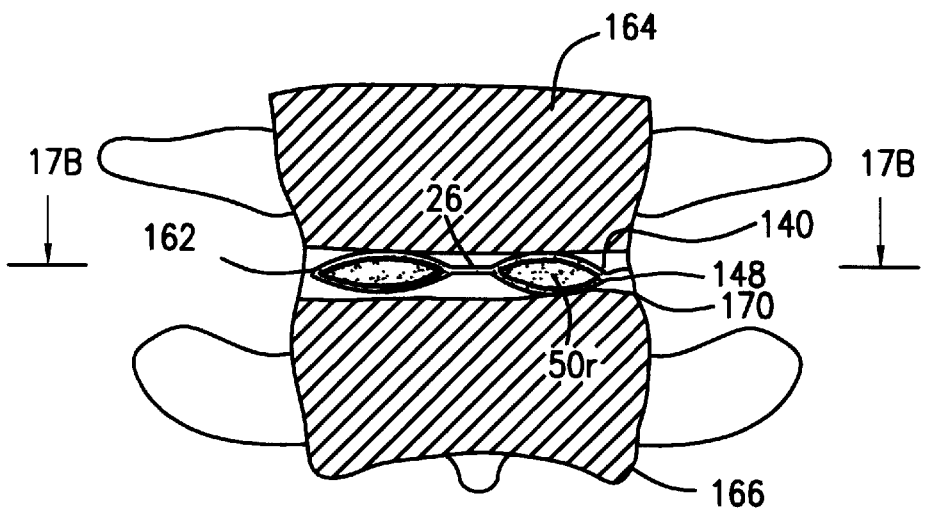
FIG. 17A
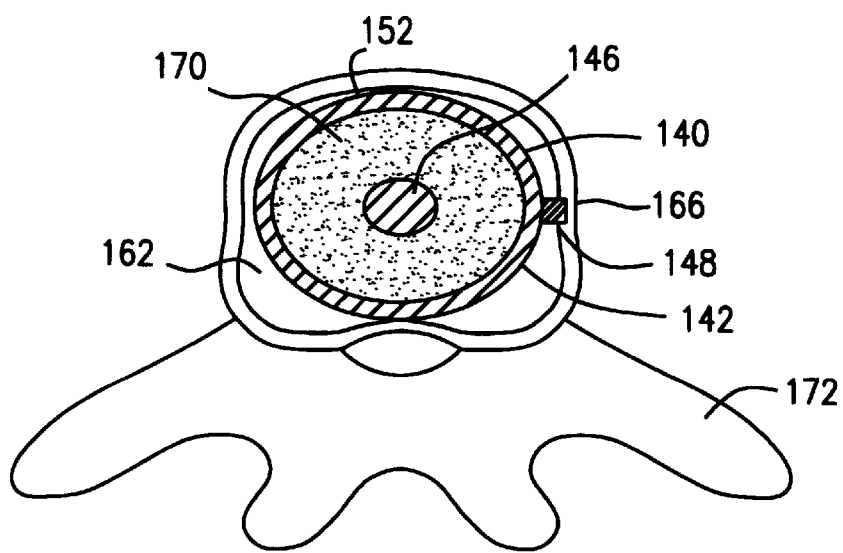
FIG. 17B

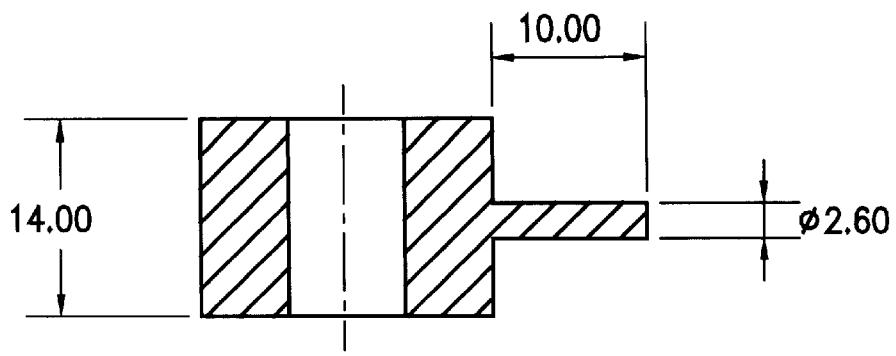
FIG. 18A
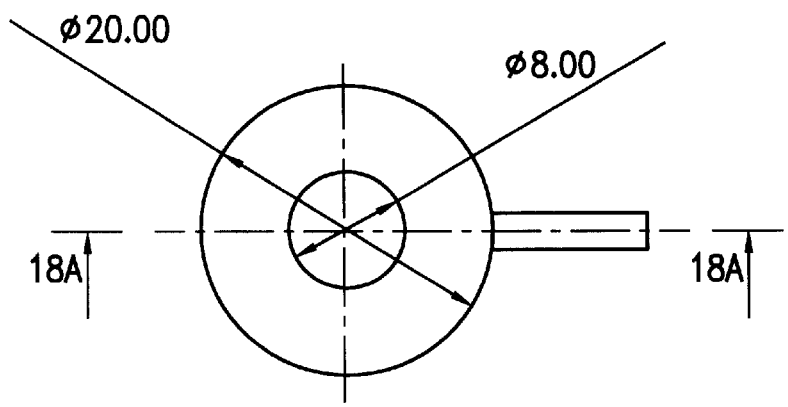
FIG. 18B
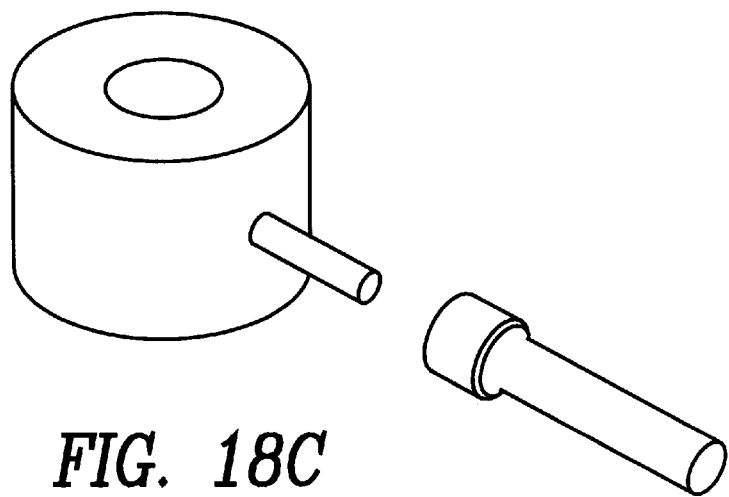
FIG. 18C

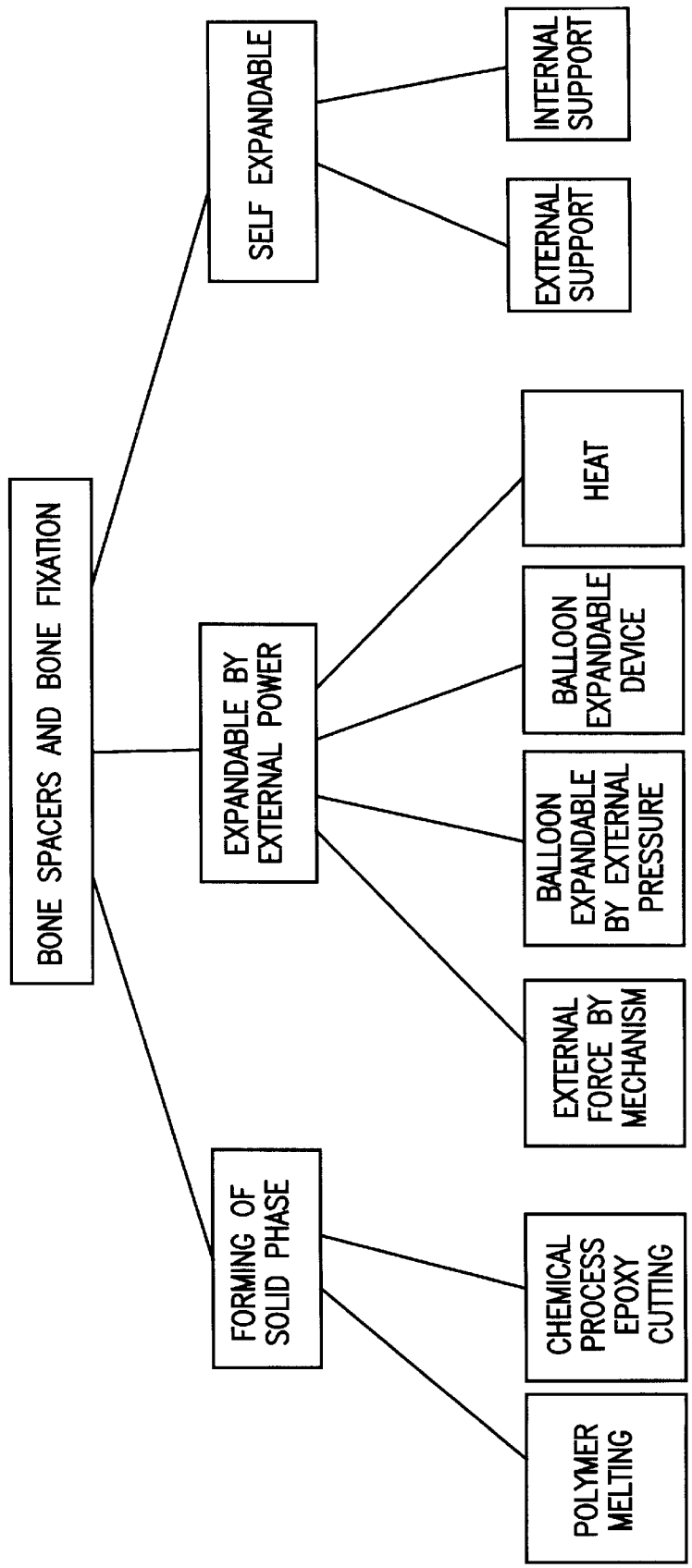
FIG. 19

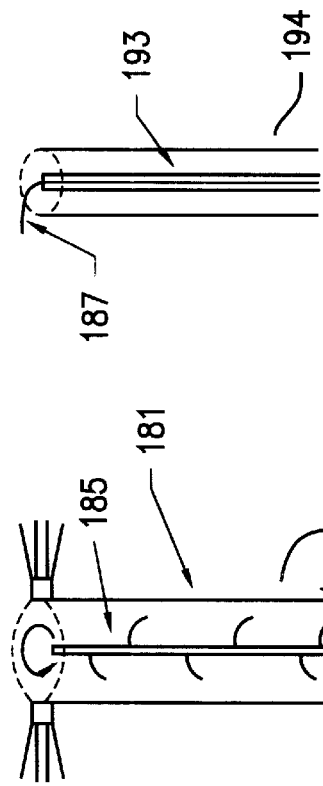
FIG. 20A
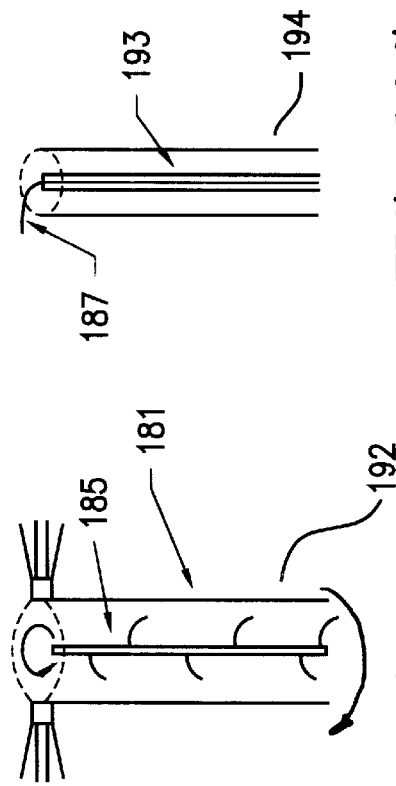
FIG. 20B
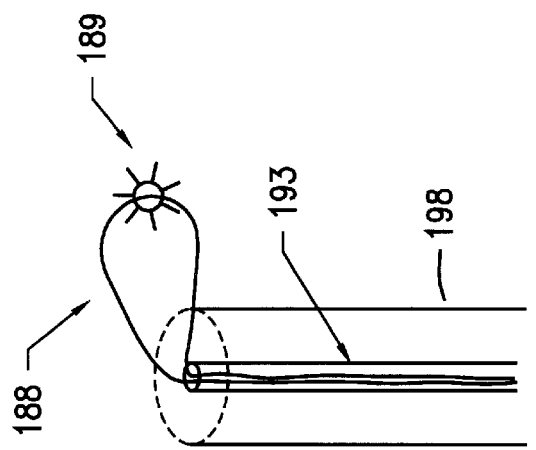
FIG. 20C
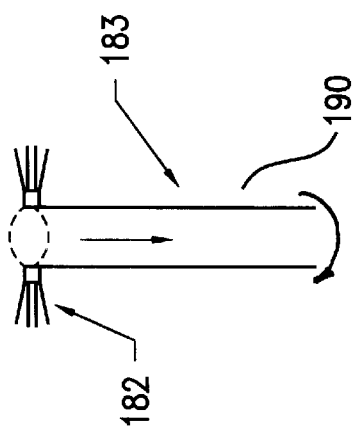
FIG. 20D
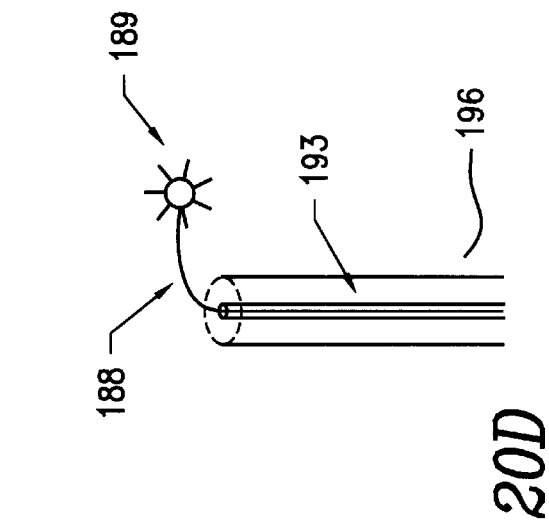
FIG. 20E

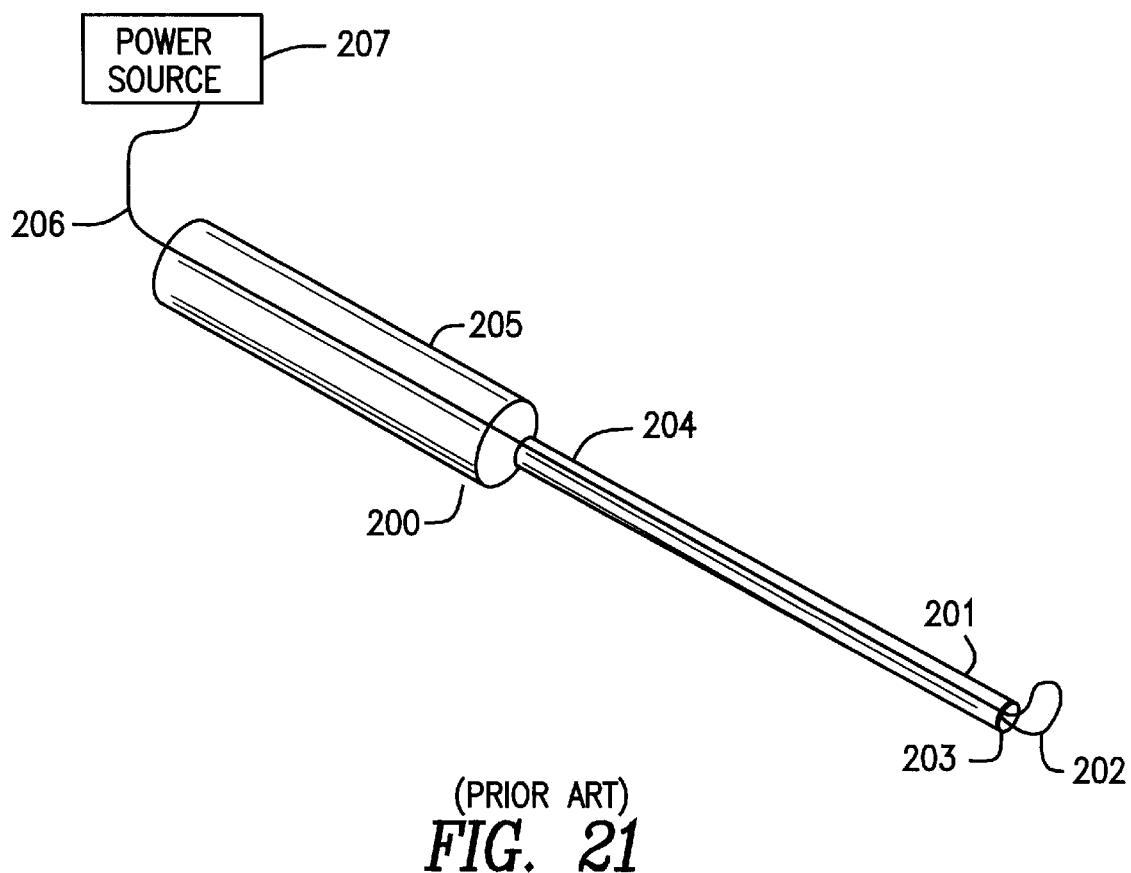
(PRIOR ART)
FIG. 21
(PRIOR ART)
FIG. 22

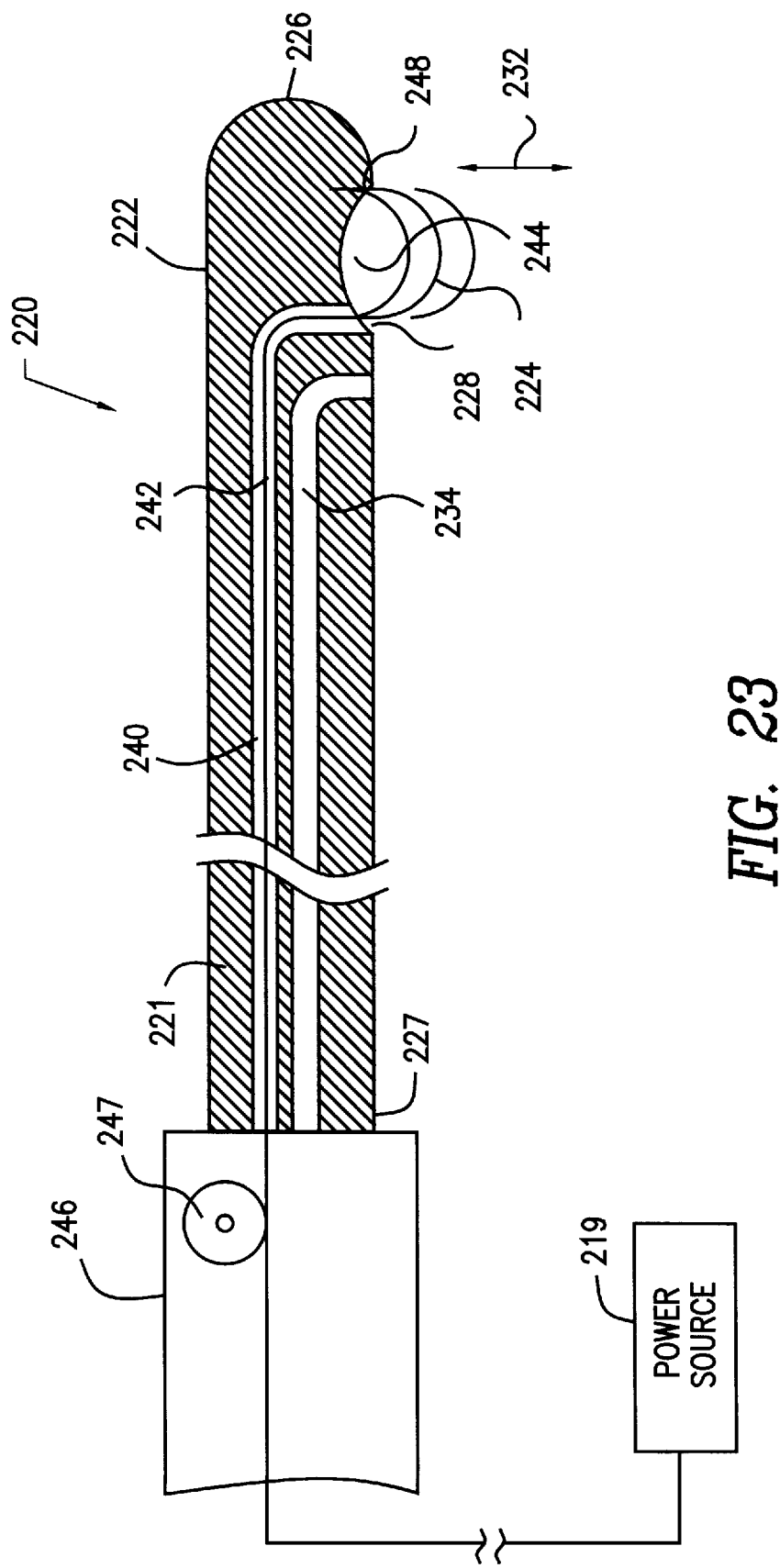
FIG. 23

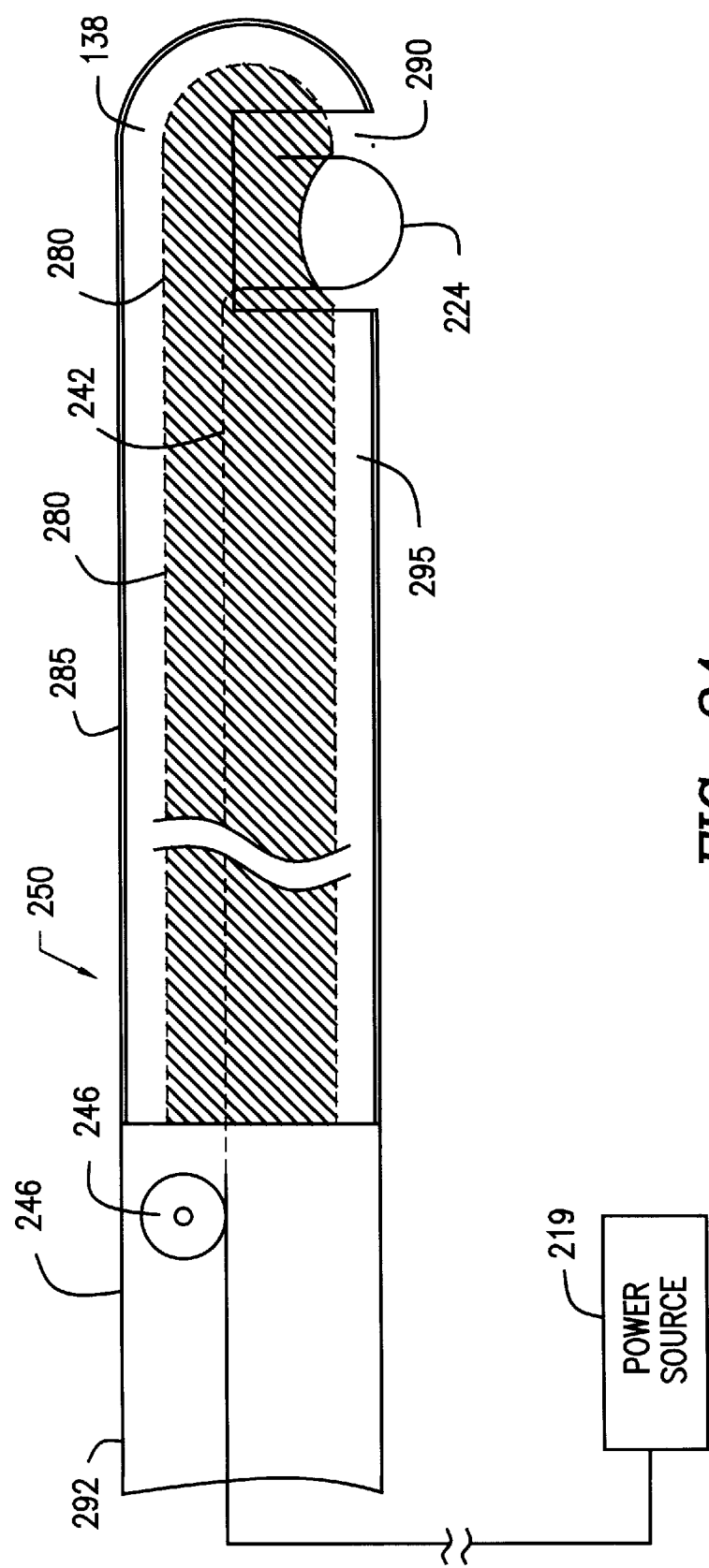

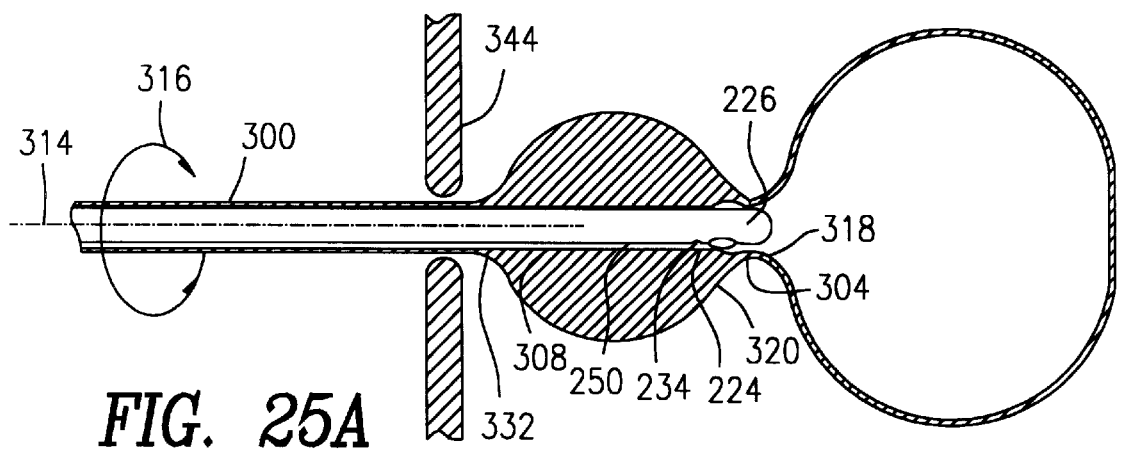
FIG. 25A
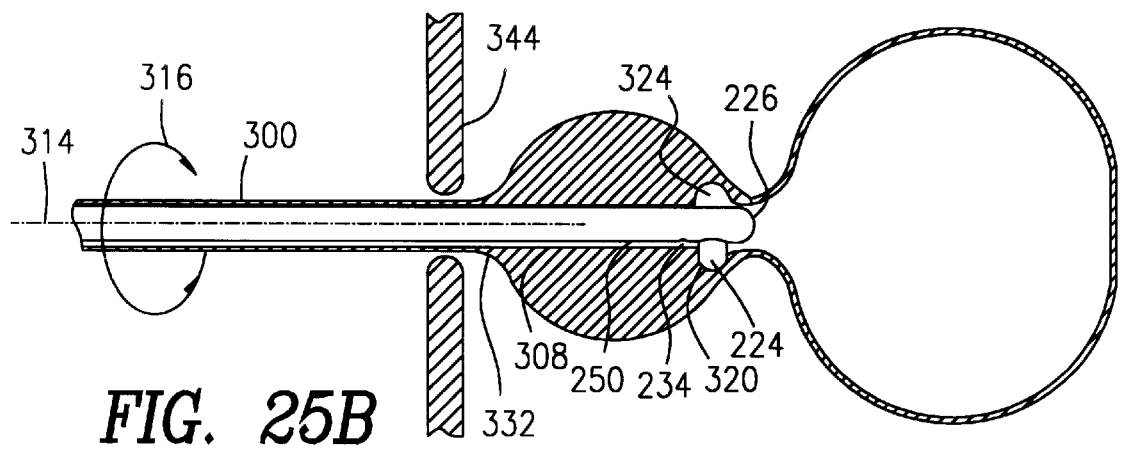
FIG. 25B
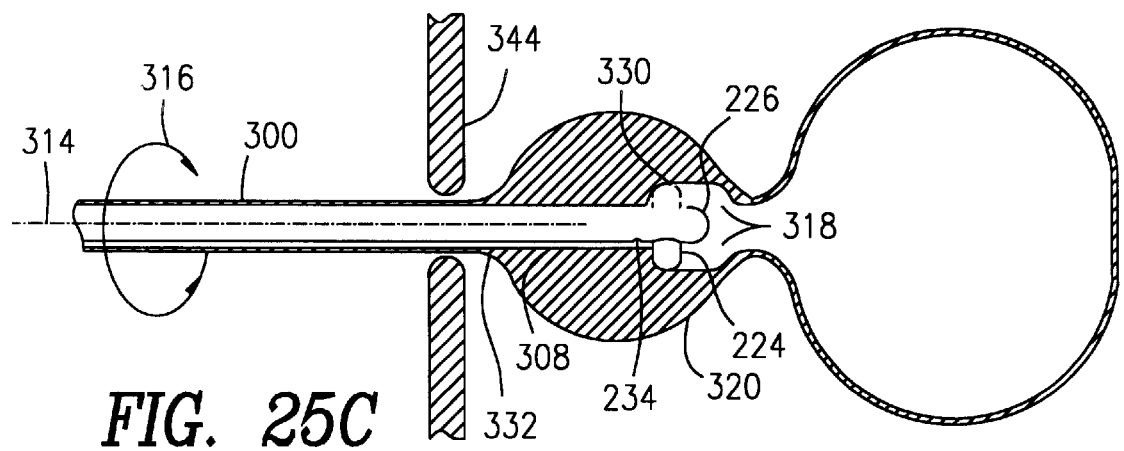
FIG. 25C

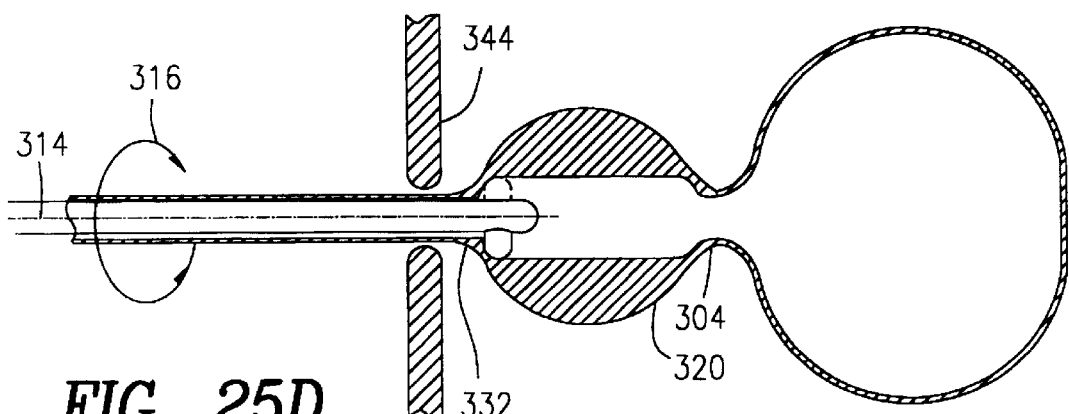
FIG. 25D
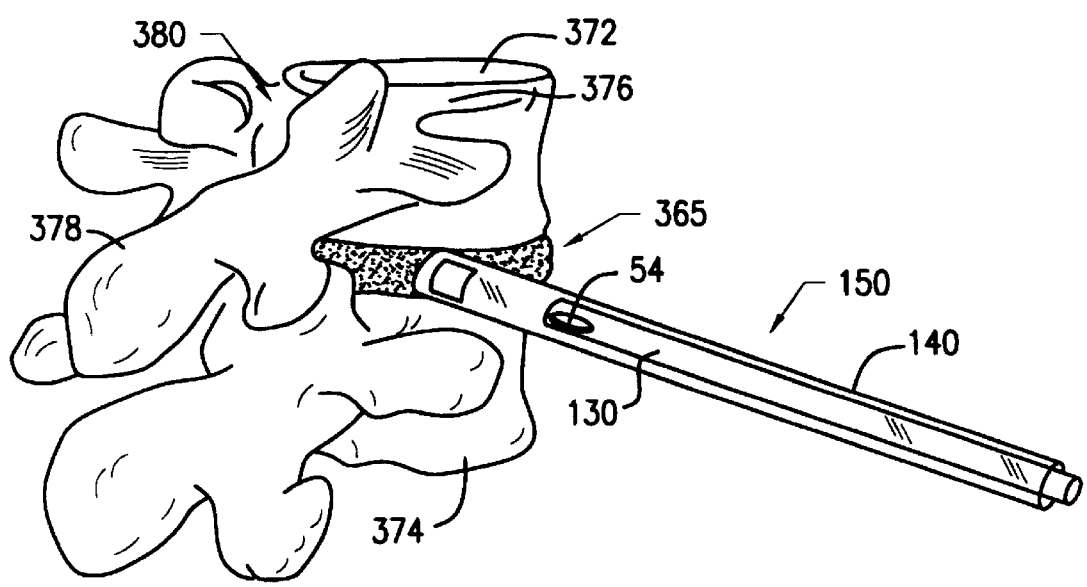
FIG. 26

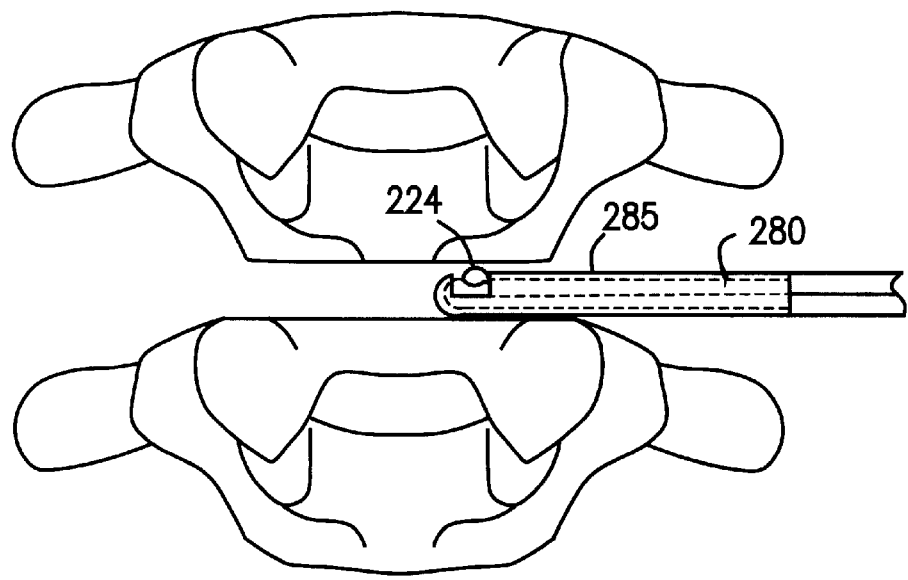
FIG. 27A
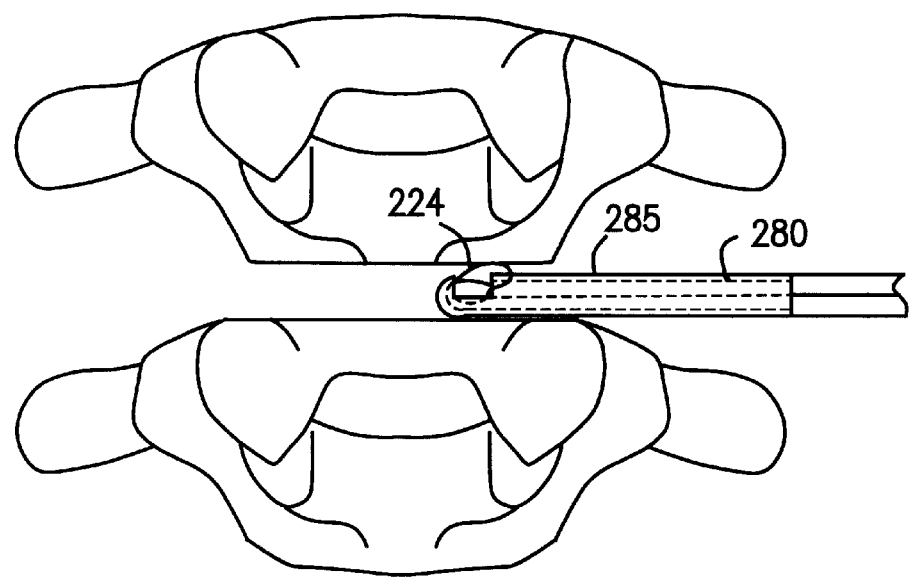
FIG. 27B

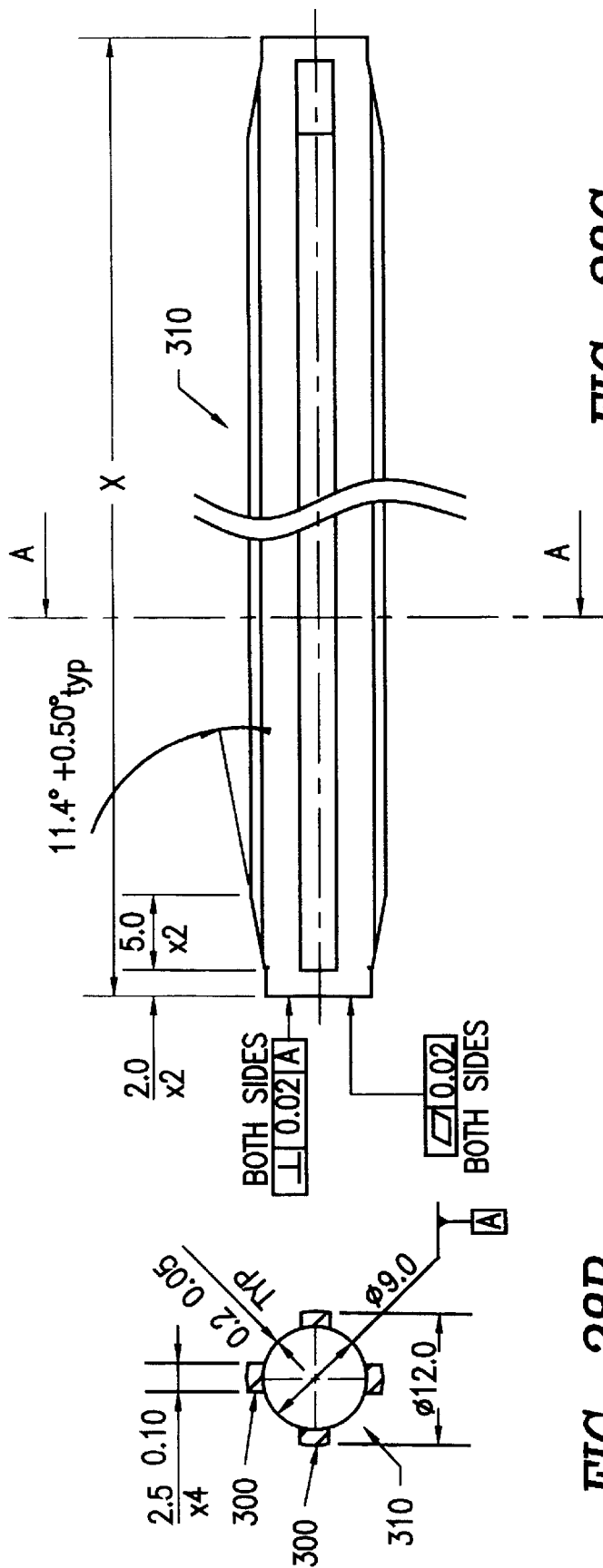
FIG. 28C
FIG. 28B
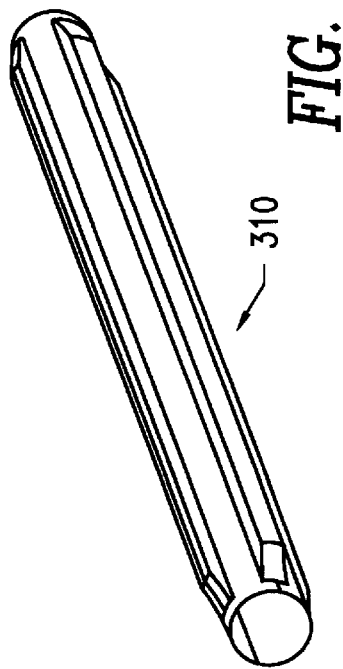
FIG. 28A

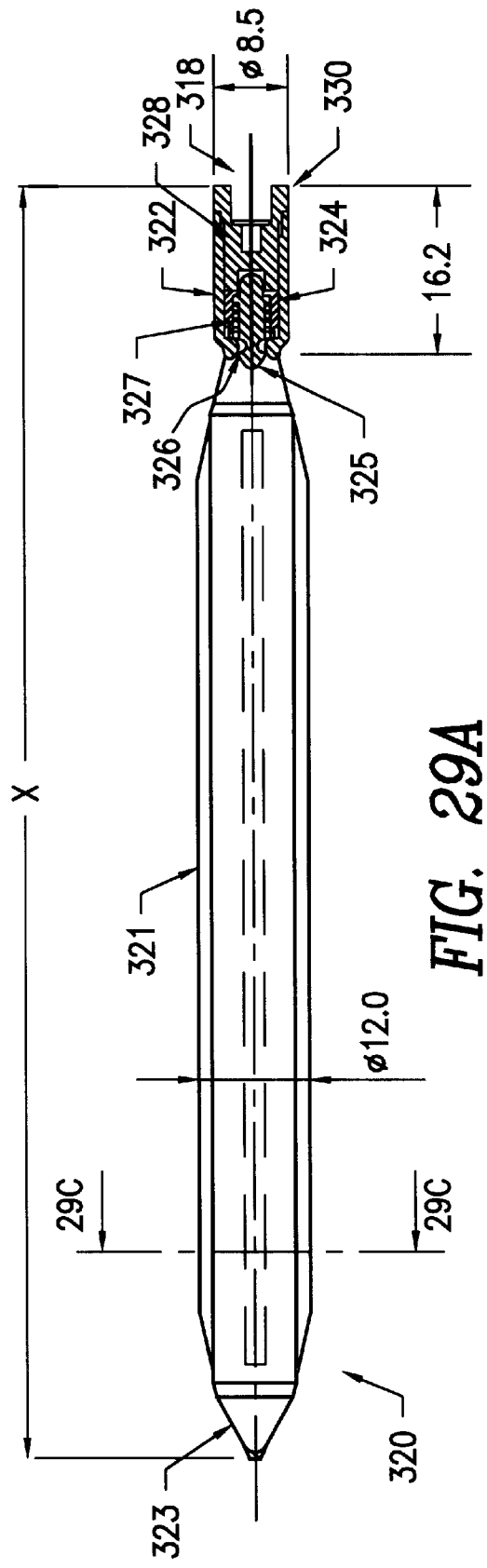

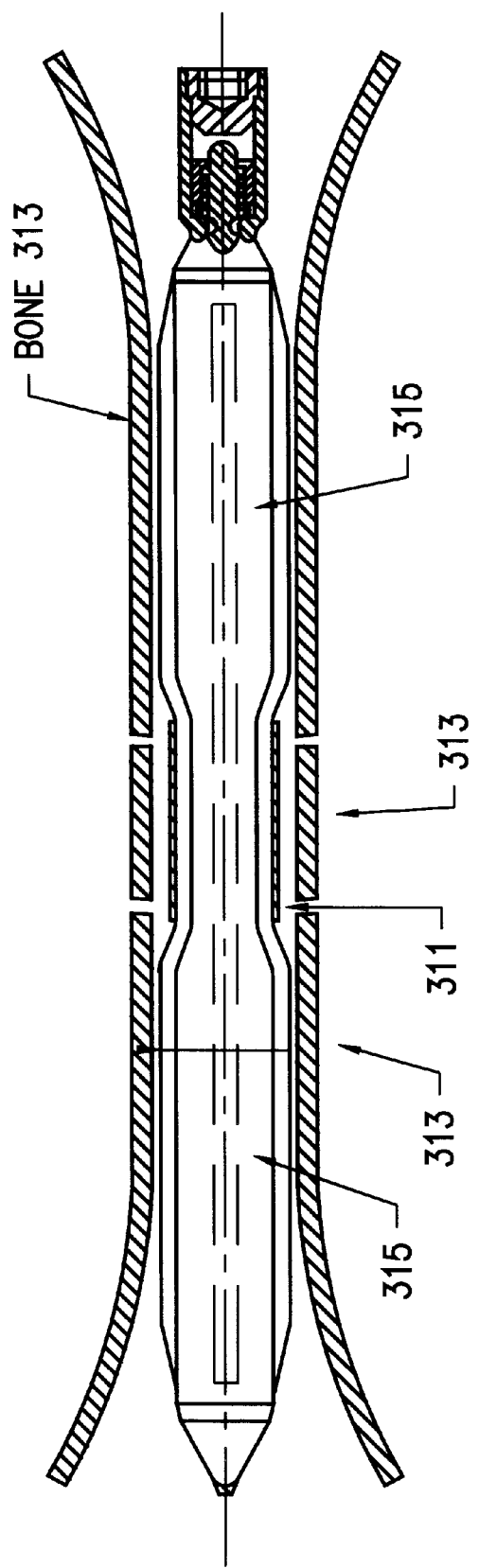
FIG. 29D

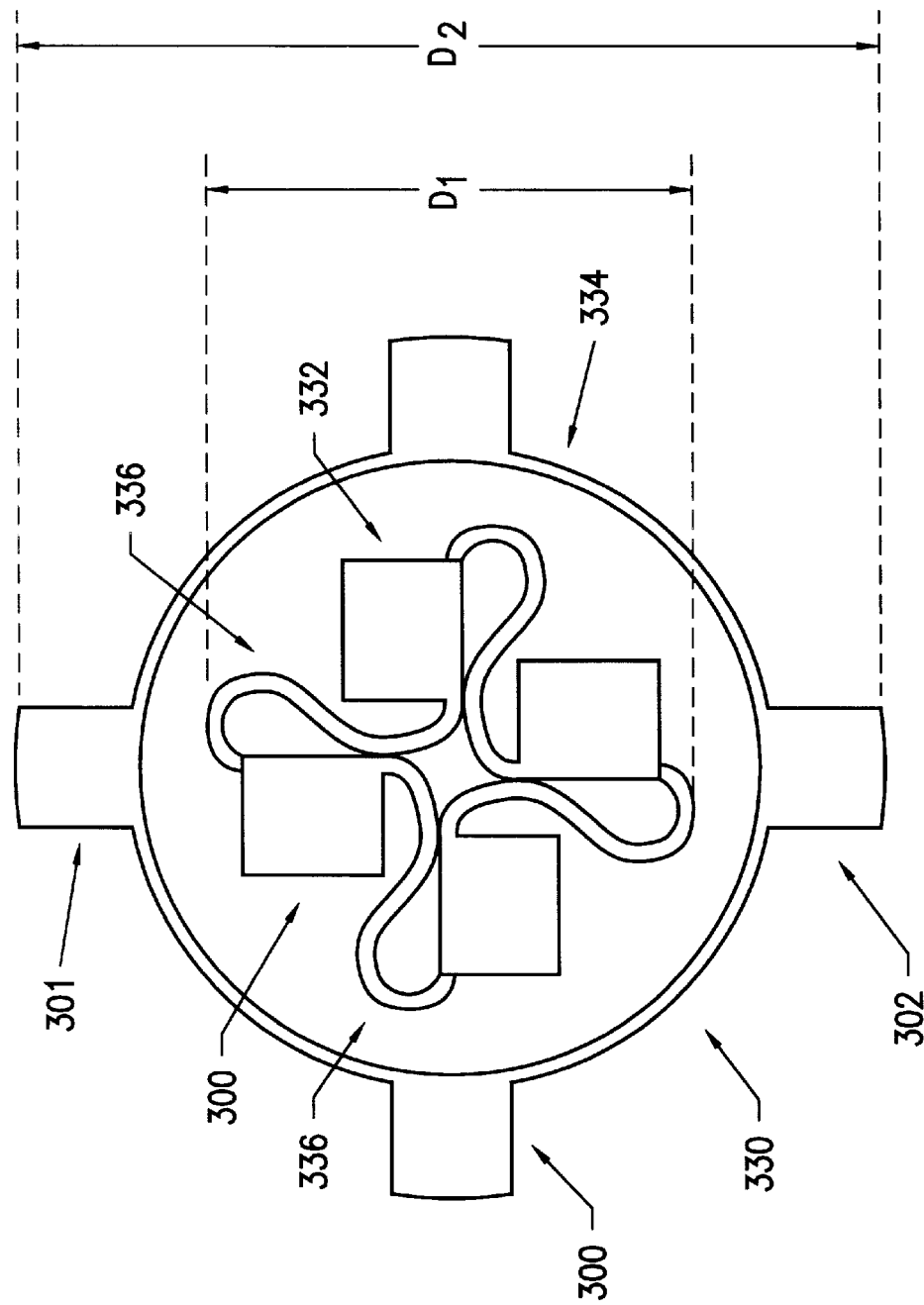
FIG. 30A

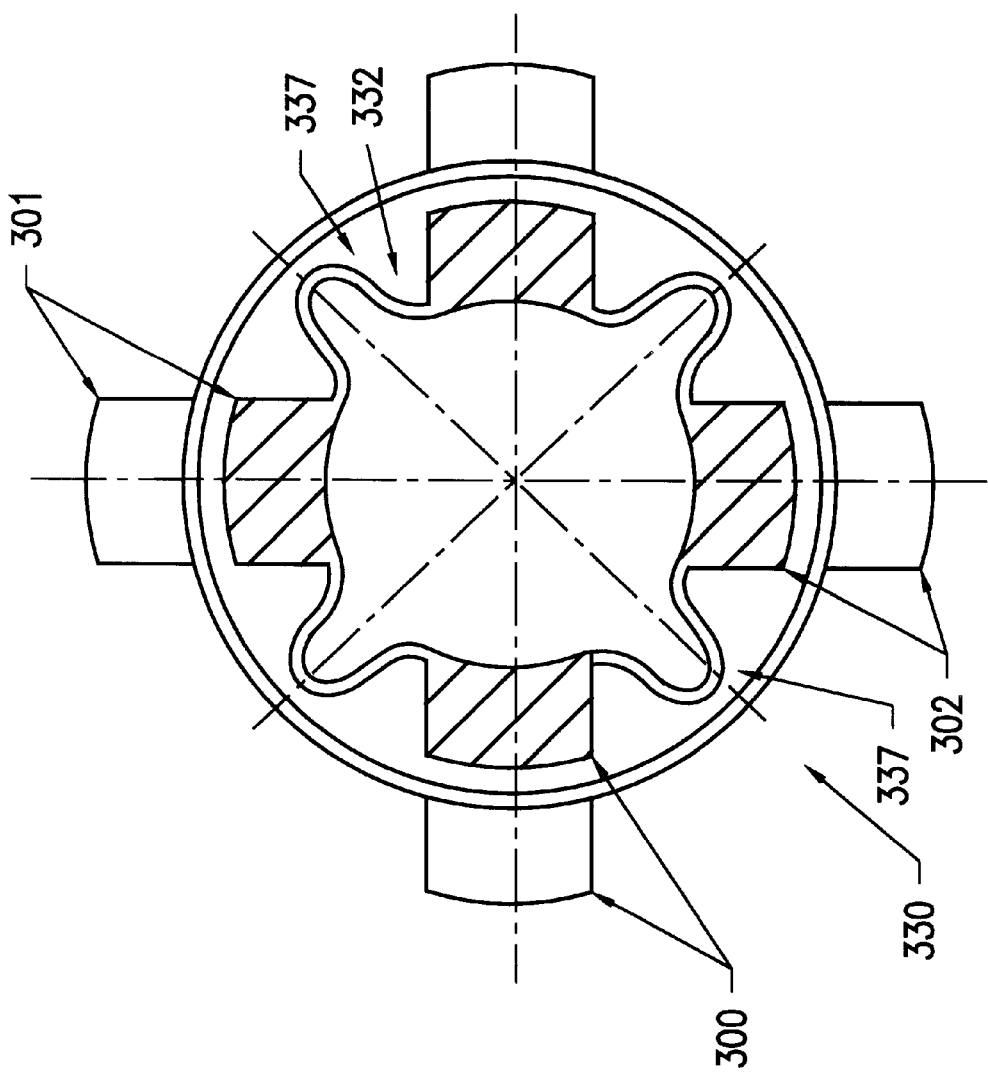
FIG. 30B

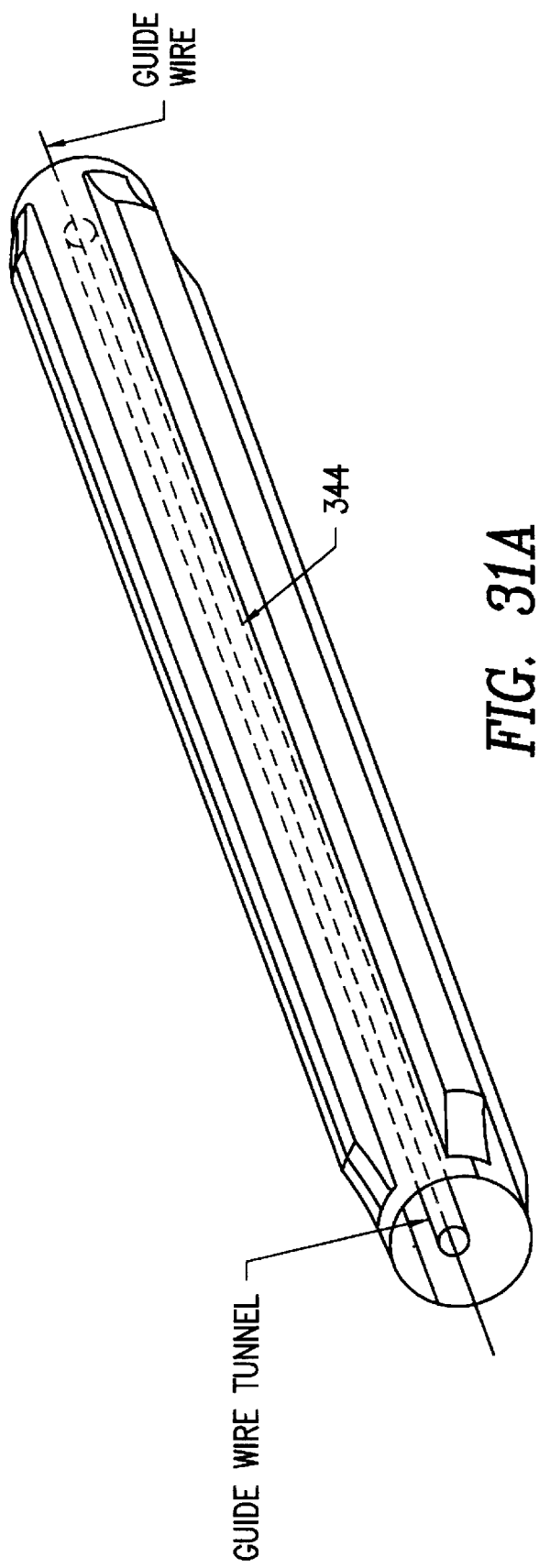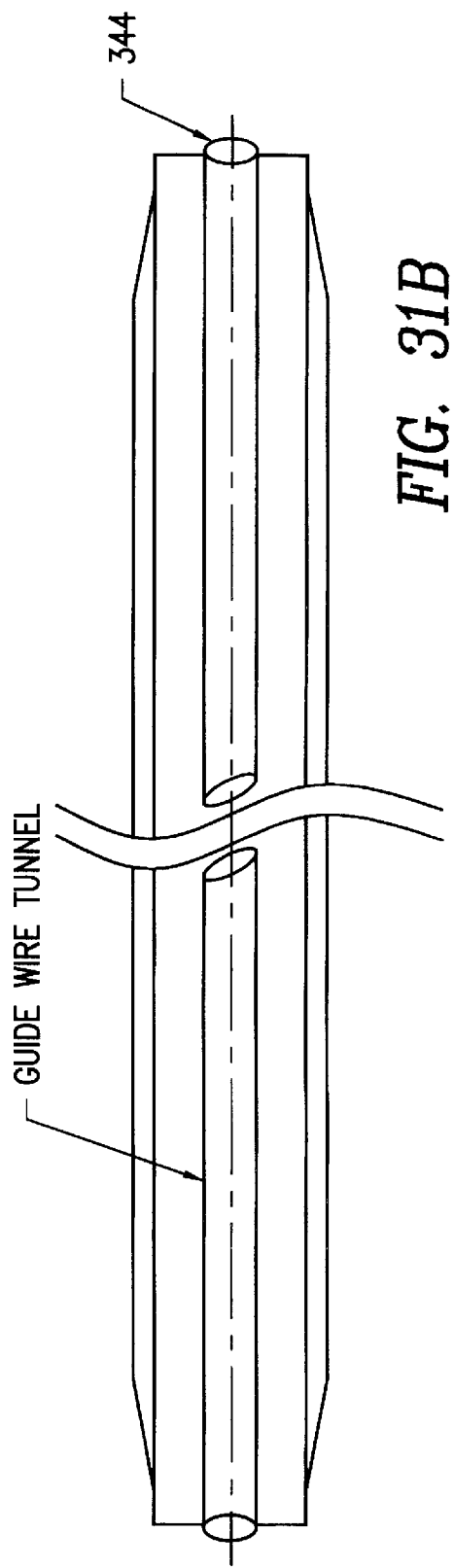

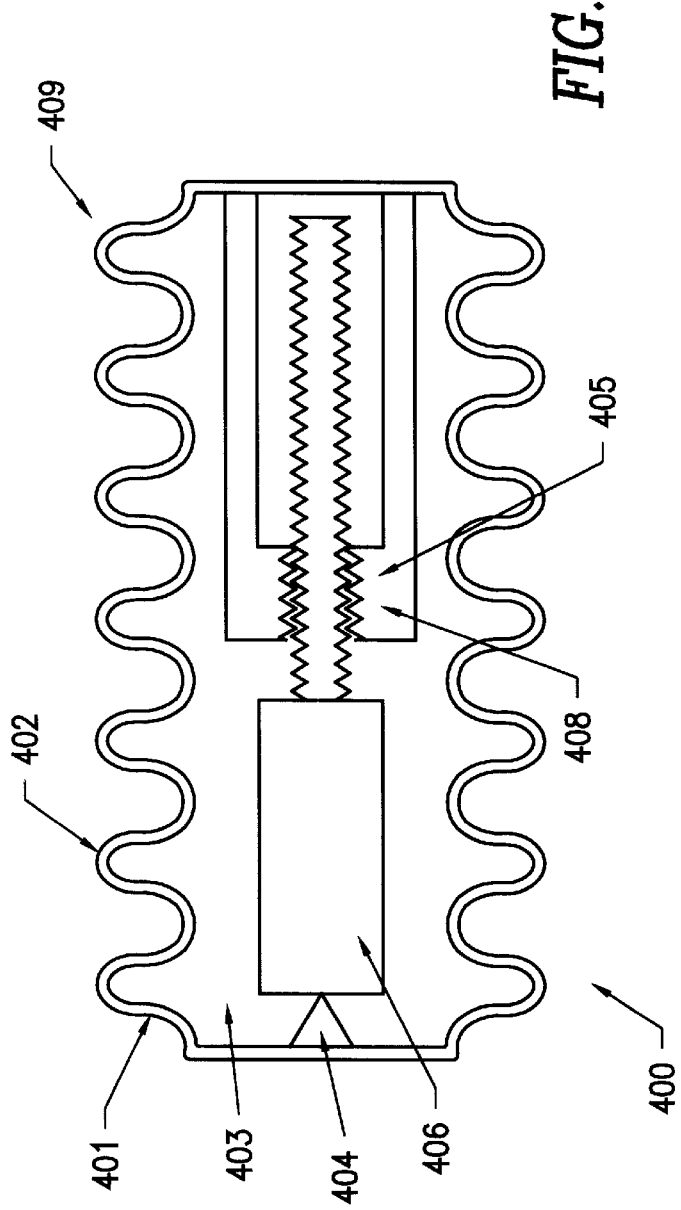
FIG. 32A
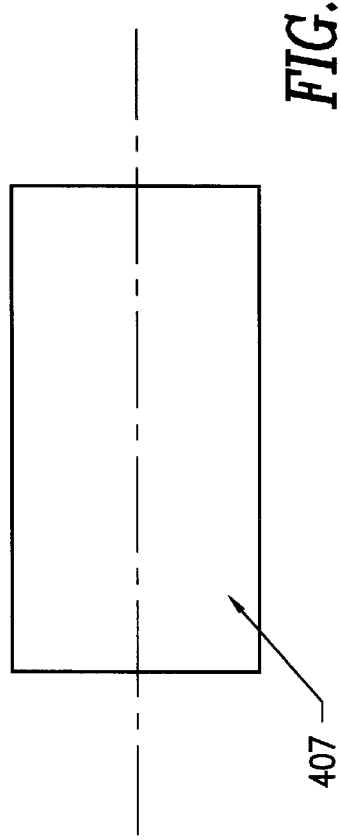
FIG. 32B

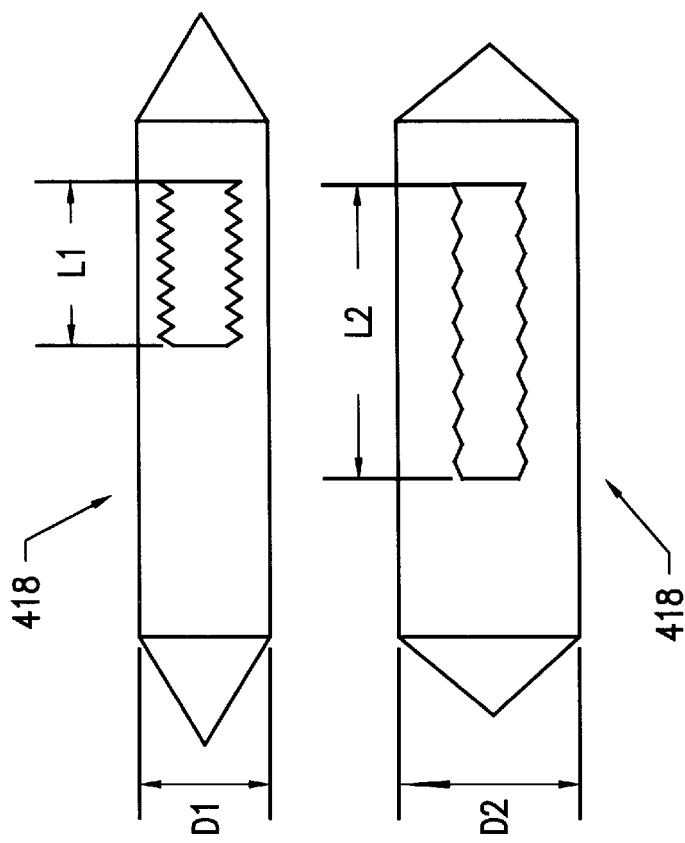
FIG. 34
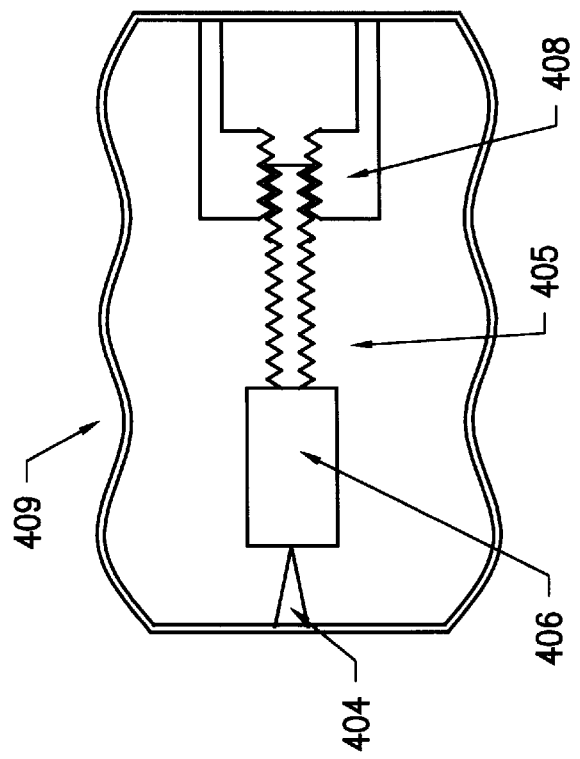
FIG. 33

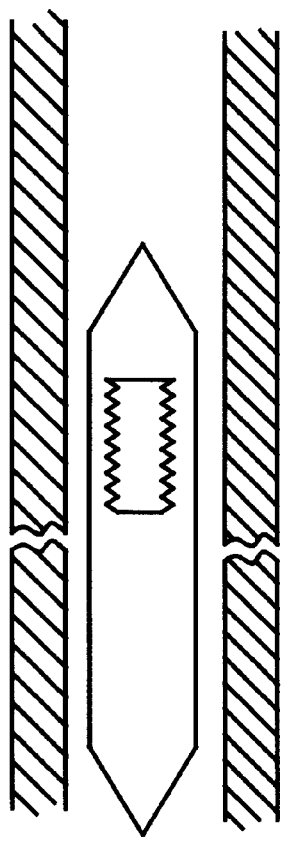
FIG. 35
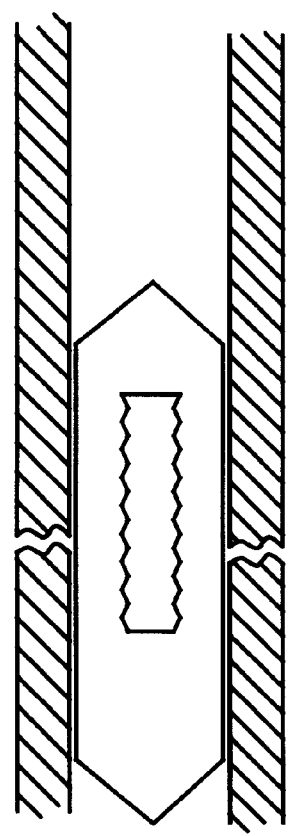
FIG. 36

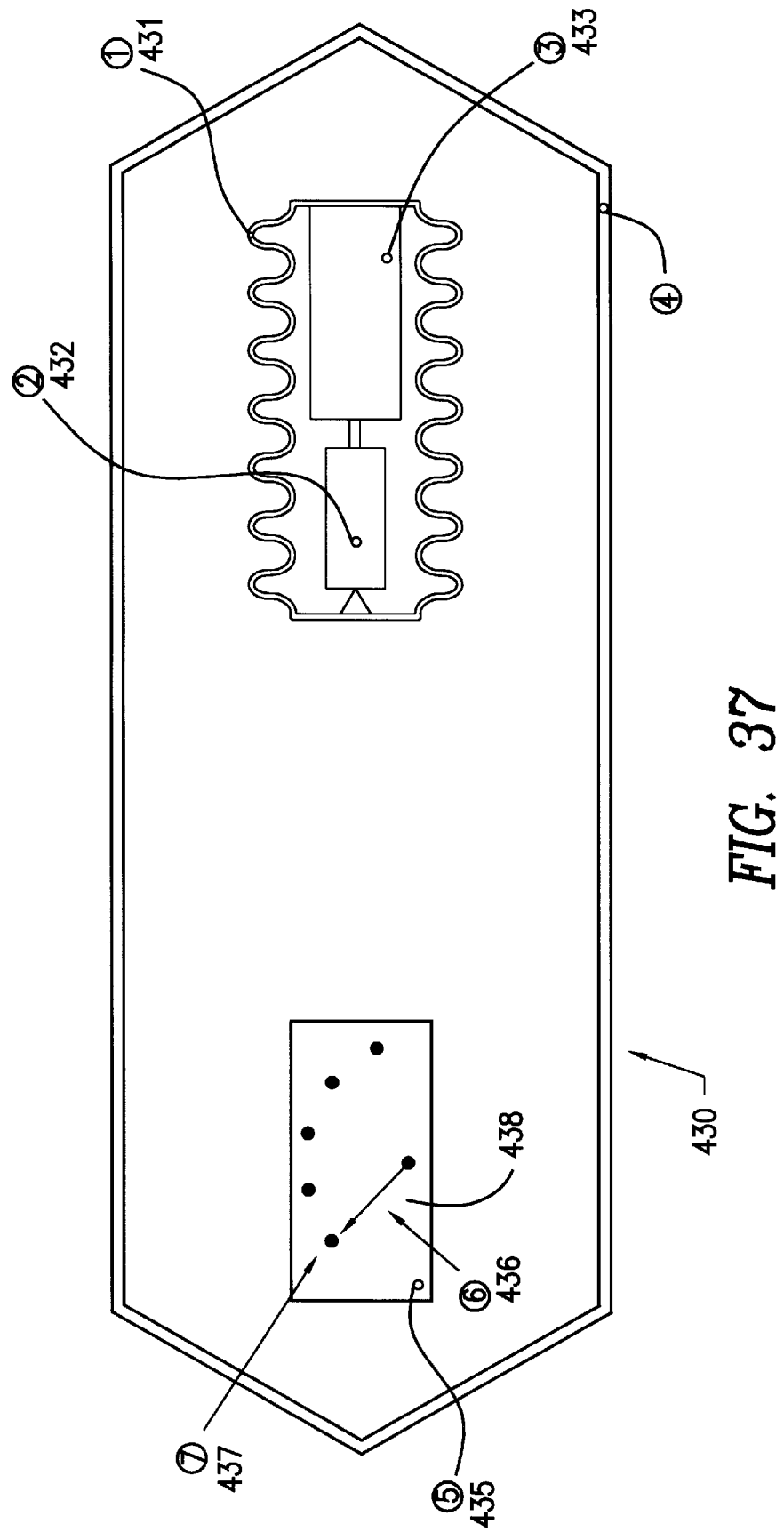
FIG. 37

SYSTEMS FOR PERCUTANEOUS BONE AND SPINAL STABILIZATION, FIXATION AND REPAIR

RELATED APPLICATIONS

The present application claims the priority of Israeli Application Serial Number 121106, filed Jun. 18, 1997 and entitled "Electrocautery Probe" (pending); U.S. Provisional Patent Application Ser. No. 60/038,942, filed Mar. 7, 1997 and entitled "Intramedullar Bone Fixation" (pending); U.S. Provisional Patent Application Ser. No. 60/038,618, filed Mar. 7, 1997, and entitled "Intravertebral Disc Prosthesis" (pending), and U.S. Provisional Patent Application Ser. No. 60/071531, filed Jan. 15, 1998, and entitled "Percutaneous Inserted, Bone Fixator Apparatus and Method" (pending), the disclosures of which are incorporated herein by reference.

FIELD OF THE INVENTION

The present invention relates to systems for percutaneous bone and spinal stabilization, fixation and repair, including intramedullar bone and vertebral fixtures, vertebral disc prostheses, and electrocautery probes.

BACKGROUND OF THE INVENTIONS

Intramedullar Fixtures for Repair of Broken Bones

Intramedullar fixtures for use in repair of broken bones are well known in the art. Such fixtures, which generally have the form of long, narrow nails, are inserted longitudinally into the bone's intramedullar cavity, so as to connect together and jointly brace two or more sections of a severely fractured bone, and thereby promote healing.

A fixture of this type must have a radial diameter large enough to firmly and rigidly hold its position after insertion. The problem of holding the fixture in position is complicated by the fact that the intramedullar cavity of most long bones is not uniform, but is, rather, narrow at the middle of the bone and flares out at the ends. The problem is further complicated by the fact that a rod inserted into such canal does not normally provide stabilization for rotational and bending movement.

Frequently, the bone medulla must be reamed out before insertion of the fixture, to make room for the fixture therein. Such reaming destroys tissue within the bone and may consequently retard proper healing. Therefore, various intramedullar nails and fixtures have been designed to have a narrow shape during insertion and then to expand radially outward to fit the shape of the intramedullar cavity and hold firmly therein.

For example, U.S. Pat. No. 4,204,531 to Aginsky, which is incorporated herein by reference, describes an intramedullar nail with an expanding mechanism. The nail includes an outer tubular sheath, a rod-shaped element longitudinally movable in the sheath, and an expandable element having two or more spreadable longitudinal branches at the front (inner) end of the nail. The nail is inserted into the medullar cavity of a bone, front end first, leaving the rear end of the nail to protrude out of the end of the bone. The rod-shaped element is then pulled back, causing the branches of the expander element to spread radially outward, thereby anchoring the front end of the nail within the intramedullar cavity.

Similarly, U.S. Pat. No. 4,854,312 to Raftopoulous et al., which is also incorporated herein by reference, describes an expanding intramedullar nail. The nail is formed of two elongate members. A first one of the members has an articulated channel, which slidably engages the second member. After the nail is inserted into the intramedullar cavity, the second member is slid longitudinally relative to the first, causing the end of the second member to bend, so that the nail spreads laterally within the cavity and is anchored in place.

U.S. Pat. No. 4,313,434 to Segal, which is incorporated herein by reference, describes a method for fixation of fracture of long bones using a flexible, inflatable bladder inside the intramedullar cavity. A small opening is drilled in the bone, and the bladder is inserted through the hole into the intramedullar cavity. The bladder is then inflated with sterile air and sealed, to fixate the bone. After the fracture has healed, the bladder is deflated and removed.

U.S. Pat. Nos. 5,423,850 and 5,480,400 both to Berger, which are incorporated herein by reference, describe methods and devices of bone fixation using a balloon catheter. The catheter, with the deflated balloon at its distal end, is inserted into the intramedullar cavity, past the fracture site. In the '850 Patent, the balloon is inserted by guiding it along guide wires that are fed through the cavity, before introducing the catheter. Once fully inserted in the cavity, the balloon is inflated to anchor it in place, and the catheter is tightened against the balloon to provide compression to the fracture.

The intramedullar fixtures and methods of implantation thereof that are described in all of the above-mentioned patents require that a portion of the expandable intramedullar fixture be left protruding through the patient's skin. Such protruding portions, however, increase the likelihood of postoperative infection and interfere with mobilization of the bone. Accordingly, it is an object of the present invention to provide methods and devices which eliminate the need for such protrusions.

In addition to fracture of large bones, fracture of long small bones is also a very common occurrence. However, a simple treatment which allows early mobilization with fracture stabilization is not currently available.

Varela and Carr in an article entitled "Closed Intramedullary Pinning of Metacarpal and Phalanx Fractures," in *Orthopedics* 13 (2), 213–215 (1990), which is incorporated herewith by reference, describe one method for fixation of finger fractures using K-wires. To fixate a fractured finger bone, several such wires, slightly bent, are inserted one after another into the intramedullar cavity. Each wire is inserted through a respective hole drilled near one end of the bone. Typically, between two and five wires are needed to fixate the bone. After insertion, the wires are cut off flush with the bone surface, and the skin is closed over the insertion site.

However, the treatment of choice today for fractured small tubular bones is the insertion of a thin metal rod (intramedullary nailing). To prevent this rod from moving, an edge of the rod is left projecting from outside the bone, such as is done in metatarsal bone fracture nailing where the end of the rod projects out of the finger tip. This fixation, however, prevents the patient from using the finger or the broken bone limb. It also does not allow good rotational stabilization. In addition, it can also result in infection due to communication between the bone medulla and the exterior of the body.

Some patents and methods for the fixation of small bones without use of protruding rods currently exist in the art. Examples include, for example, Lewis, R. C., Jr., Nordyke, M., Duncan, K., Clinical Orthopedics Related Research, 1987, 214 (85–92); Nordyke, M. D., Lewis, R. C., Janssen, H. F., Duncan, K. H. J. of Hand Surgery, 1988, 13/11 (128–134); Varela, C. D., Carr, J. B., Orthopedics, 1990, 13/2: 213–215; and, WO 94/12112, U.S. Pat. No. 4,204,531, and U.S. Pat. No. 4,854,312.

One method in particular is described in an article "Expandable Intramedullary Device for the Treatment of Fractures in the Hand", Royce C. Lewis et al., Clinical Orthopedics and Related Research, Tech. Ortho., 1989, 1:18–91. In this article, an expandable intramedullary nail is inserted after the fractured bone is opened and the nail is inserted through the broken part. The nail is inserted through the fracture and not through the bone extremities. Yet, there still exists a need for a percutaneous minimal trauma insertion of an internal fixator for small bones which does not necessitate exposure of the bone surface.

Intramedullar nailing through the finger tip is also discussed in the article "Closed intramedullary pinning of metacarpal fractures", Varela, C. D.; Carr, J. B., Orthopedics, 1990, 13/2: 213–215. However, this nailing does not involve an expandable nail.

Numerous of the bone fixation patents mentioned above involve implantation of different metal devices (i.e., Nitinol, Titanium, etc.). Another possibility is to use a detachable inflatable balloon as an expandable intramedullary bone fixator. There are patents that exist today for bone fixation with a balloon, but these do not provide intramedullary nailing. They provide only a joining effect as in the pulling of one broken bone towards the other. Examples of these include U.S. Pat. Nos. 5,423,850 and 5,480,400 (described above).

Accordingly, a variety of significant shortcomings exist in the present art of fracture stabilization. To address these problems, the present inventors have provided an intramedullary nailing which is accomplished using a variety of inventions desribed below. For example, by using a detachable intramedullary balloon located at the middle of the fracture, and extended across both bone segments, a improved device is provided which addresses the numerous shortcomings of the prior art. Such devices provide the patient with a rapid post-surgery fracture stabilization resulting in mobilization of the limb and reduced chance for infection, as well as the possibility of removal after bone healing, if needed.

Intervertebral Disc Ablation and Spacer Placement

Back pain is a widespread ailment which is often attributed to disc pathologies and vertebral instability. Nowadays, the treatment of choice of spinal fusion involves disc removal followed by implantation of a plate with or without screws into the intervertebral space (See e.g., U.S. Pat. No. 5,520,690, U.S. Pat. No. 5,522,816, and U.S. Pat. No. 5,529,899). The procedure also involves implantation of a bone graft in the intervertebral space.

Patents and applications employing artificial intervertebral discs currently exist, although they have not yet been proven successful in patients (U.S. Pat. No. 4,759,769; WO 92/14423; WO 90/00037; WO 96/37170). Existing treatments involve introductory surgery for removal of the original spinal disc tissue and placement of the intervertebral support. An intervertebral spacer and stabilizer is placed within the intervertebral space followed by the removal of the damaged disc and cleaning of the intervertebral bone surfaces by use of different cutters and retractors (U.S. Pat. No. 4,904,260 and U.S. Pat. No. 5,645,598 for example). A bone graft is then implanted to facilitate spine fusion.

All procedures utilizing the above method require actual opening and dissection of the back and/or the abdomen or performing the procedure laparoscopically. Accordingly, there is currently a need in the art for a percutaneous non-laparoscopic type minimally invasive technique to facilitate and improve the current method for spine fusion.

In addition, the disc ablation procedure may involve the interposition of a spacer in the intervertebral space to support the vertebrae until spine fusion is achieved by osteogenesis. The existing spacers are constructed with a fixed diameter according to the space needed to be kept in the intervertebral area. Although one spacer has been disclosed which expands by rotating a screw, it only expands upwards and downwards, and therefore still has a large insertion profile. This does not allow for the insertion of the device percutaneously in a minimally invasive technique. As discussed in greater detail below, there is a need for a spacer or prosthesis that is created with a small diameter and which can expand radially once implanted. In addition, as also discussed below, there is also a need for an intervertebral tissue extractor which can likewise function percutaneously for use in the procedures described.

Intervertebral Disc Prostheses

Intervertebral disc prostheses are also known in the art. Such a prosthesis is generally inserted into the intervertebral space following the removal of all or a part of the disc matter from the space. Upon insertion, the prosthesis holds two adjacent vertebrae apart from each other, so as to maintain the vertebrae in an anatomically correct spacing and orientation. Following surgery to implant the prosthesis, bone generally grows from the vertebrae into and around the prosthesis, thereby holding the prosthesis firmly in place and preventing undesirable motion of the vertebrae relative to each another.

U.S. Pat. Nos. 4,772,287 and 4,904,260 to Ray et al., which are incorporated herein by reference, describe prosthetic disc capsules having a generally cylindrical shape and containing a gel material having properties similar to those of the disc matter. After removal of a portion of the disc matter, two such prosthetic capsules are implanted in the disc space, one on either side of the sagittal axis of the spine. The capsules may be implanted in a deflated state and then inflated with the gel to a pressure sufficient to hold the adjoining vertebrae apart.

To implant the prosthetic disc capsules in the disc space, it is necessary to open the patient's back and perform a partial laminectomy to gain access to the disc space. Such open laminectomy is a major surgical procedure, with attendant risks, side effects and long recovery time. Other disc prostheses, as described, for example, in U.S. Pat. Nos. 3,875,595, 4,349,921, 3,867,728, 4,554,914, 4,309,777, 3,426,364, and 4,636,217, and incorporated herein by reference, similarly require major surgery for implantation thereof.

In response to the risks and lengthy recovery period associated with open surgery for treatment of bulging or herniated discs, an alternative, minimally-invasive surgical technique of percutaneous diskectomy has been developed. In percutaneous diskectomy, a narrow cannula is inserted into the disc space in a lateral approach through a small incision in the patient's side. The lateral approach to the disc obviates the need to cut through bone and/or substantial amounts of muscle, as required by other surgical methods known in the art. Surgical tools are passed through the cannula to cut away and remove disc material, so as to relieve the outward pressure of the disc on surrounding nerves and thus to alleviate the pain caused by the bulging or herniated disc.

Percutaneous diskectomy can be performed as an outpatient procedure and, when successful, allows the patient to return to full activity after only a short recovery period. The procedure is successful only in about 70% of cases or less, however, and does not allow the full range of treatment afforded by open back surgery. For example, disc prostheses and methods of implantation of such prostheses that are known in the art are not suitable for use in the percutaneous approach.

The vertebrate spine is the axis of the skeleton, on which the body parts hang. The bony vertebral bodies of the spine are separated by intravertebral discs, which serve as a cushion between vertebral segments of the axial skeleton. These discs comprise a fibrous annulus and a nucleus, which is a gel-like substance, contained within the annulus. A disc herniation occurs when the tissue of the nucleus bulges out of the annulus. The herniated nucleus may exert pressure on a spinal nerve adjacent to the disc, resulting in pain or loss of muscle control. The normal procedure in such cases is to remove the herniated disc tissue in open surgery, but this is a major procedure with long recovery and potentially serious side effects.

In response to the dangers and complications of open spinal surgery, minimally invasive procedures for removal of herniated tissue have been developed. One type of such procedure as described above, is percutaneous diskectomy, in which herniated tissue of the nucleus of the disc is removed from the patient's body. Apparatus for such procedures is described, for example, in U.S. Pat. No. 5,131,382, which is incorporated herein by reference. The nuclear tissue is removed thorough a cannula, which is inserted through a small incision, preferably in the patient's side, into the intervertebral space. By making the incision as small as possible and entering the body laterally, rather than dorsally, trauma to the patient is minimized. Removal of the herniated tissue is a long process, however, frequently requiring removal and reinsertion of resection tools many times.

In some diskectomy procedures, after the tissue is removed, a disc prosthesis is inserted to replace the nucleus and possibly the annulus, as described above, and in PCT publication WO 96/11643 for example, whose disclosure is incorporated herein by reference. Generally, it is desired that the two adjacent vertebrae fuse together, around the prosthesis. In order to facilitate insertion of the prosthesis and encourage subsequent bone fusion, the disc tissue should be thoroughly cleaned out during diskectomy. However, percutaneous diskectomy procedures and devices known in the art do not generally achieve such thorough cleaning.

Prosthesis Loosening

As discussed herein, medical implants such as orthopedic fixation devices can be inserted into the body in a small diameter state, and, once inserted, can be inflated to a larger diameter and/or a longer length. In U.S. Pat. No. 5,376,123, for example, Dr. Klaue teaches a hip prosthesis having an inflatable member to firmly fixate the implant into the femoral bone medulla. Moreover, as discussed below in greater depth, the present inventors have provided novel devices, including intramedullary nails, spine cages, and other inflatable implants which can be inserted into the body in a minimally invasive technique in a small diameter state and then inflated with a non-compressible material to a larger diameter state.

In the past, prostheses have often shown a decrease in effectiveness over time due to loosening effects. For example, hip prosthesis implants and knee prosthesis implants have shown a high rate of implant loosening over time. This loosening is caused by a space which is created between the implant shaft in the area where it is attached to the bone. This complication, which usually appears 1–13 years after implantation, requires a second operation to eliminate the loosening. Likewise, it is known that bone implant complications generally can include loosening between the implant and the bone, causing relative movement between the bone and the implant, and forcing another operation to achieve good bone to implant fixation.

As a result, there is a need for a device which can be provided to prevent movement between an implant and the bone, to optimize the success and fixation of the implant over time. To address this need, the present inventors have provided a non-invasive technique and related device which allows a prosthesis to be changed in diameter and/or length whenever needed. In this manner, the need for another procedure to correct loosening (which usually appears within a few years) can be eliminated.

Electrocautery Probes

Electrocautery probes are used in a wide range of surgical procedures, particularly in less-invasive and minimally-invasive surgery. One of the most common uses of such probes is in surgical treatment to relieve urinary obstruction due to enlargement generally known as transurethral resection of the prostate (TURP).

FIG. 21 is a schematic diagram showing a prior art electrosurgical probe 200 for use in TURP and other procedures. Such probes are distributed, for example, by Olympus Optical Company, of Tokyo, and Karl Storz GmbH, of Tuttlingen, Germany. Probe 200 comprises a shaft 201 having a wire loop 202 of adjustable size, protruding from a distal end 203 of the shaft. Shaft 201 is connected at its proximal end 204 to a handle 205, which is used by a surgeon to manipulate and control the probe. Wire loop 202 is connected via a wire 206 to an electrosurgical power source 207, which supplies RF energy to the loop.

FIG. 22 is a schematic, sectional illustration showing the use of probe 200 in a TURP procedure, as is known in the art. Shaft 201 of probe 200 is inserted through urethra 209 of a subject so that distal end 203 thereof is within prostatic urethra 208, i.e., the portion of urethra 209 surrounded by prostate gland 210. Power source 207 is activated, so that an electrical current passes through wire 206 and loop 202. The current passes from loop 202 through the tissue or prostate 210 which is adjacent to the loop, thus resecting the tissue. The current returns via a grounding pad (not shown in the figures). The surgeon draws loop 202 back and forth along prostatic urethra 208, as indicated by an arrow 211 in the figure, so as to resect a "chip" of tissue from prostate 210 along the entire length of the prostatic urethra. This procedure is repeated until prostatic urethra 208 and prostate gland 210 have been completely resected.

In resecting prostate 210, the surgeon must take great care that electrocautery loop 202 not contact urethral sphincter 212, which is proximally adjacent prostatic urethra 208, as shown in FIG. 22. If loop 202 is drawn too far proximally along the direction of arrow 211, it will resect sphincter 212 and/or nerves associated therewith, with the result that the subject may become permanently and irreversibly incontinent.

SUMMARY OF THE INVENTION

It is an object of the present invention to provide improved devices and methods for intramedullar fixation of fractured bones.

It is an object of the invention to provide devices and methods for fixation of the humerus and other long bones.

It is an object of the invention to provide devices and methods for fixation of fractures of the phalanx bones or other small bones of the hands and feet.

It is an object of the present invention to provide devices and methods which allow intramedullar bone fixation using minimally-invasive surgical procedures, so as to generally reduce operative trauma and allow speedier post-operative recovery.

It is an object of the present invention to provide devices and methods for percutaneous bone and spinal stabilization, fixation and repair.

It is a further object of the present invention to provide a percutaneously inserted intramedullary bone fixation device for the stabilization of fractured bones.

It is an object of some aspects of the present invention to provide devices and methods for intramedullar fixation that allow mobilization of a bone within a short time of fixation thereof.

It is an object of other aspects of the present invention to reduce the risk of postoperative infection following intramedullar fixation.

It is a further object of the present invention to provide inflatable balloon fixation devices for intramedullary nailing.

It is a further object of the present invention to provide fixation devices having a valve for inflation and deflation of the devices.

It is a further object to provide intramedular devices having fixation elements for anchoring the devices against the inner surface of a bone.

It is a further object of the present invention to provide methods and devices which provide for a less invasive surgical treatment of intervertebral spine fusion.

It is a further object of the present invention to provide a minimally invasive method and device for treatment of intervertebral spine fusion which includes the extraction of intervertebral tissue and the placement of an intervertebral spacer.

It is an object of the present invention to provide an improved disc prosthesis for implantation in the intervertebral disc space.

It is a further object of some aspects of the present invention to provide a disc prosthesis suitable for implantation using minimally invasive methods of percutaneous diskectomy. It is another object of these aspects of the invention to provide devices and methods for use in percutaneous implantation of the prosthesis.

It is a further object of the present invention to provide a prosthesis whose size can be increased long after implantation, without the need for a second surgical procedure.

It is a further object of the present invention to provide a prosthesis whose size can be increased from outside the body by remote activation means.

It is a further object of the present invention to provide an orthopedic prosthesis whose size can be increased from outside the body by remote activation means to treat and eliminate loosening effects.

It is an object of some aspects of the present invention to provide an improved electrocautery probe.

It is another object of some aspects of the present invention to provide an improved method of minimally invasive diskectomy.

It is also an object of some aspects of the present inversion to provide an improved method of transurethral resection of the prostate (TURP) which minimizes the possibility of undesired side effects.

Further objects of the invention will become apparent upon reference to the drawings, description and/or claims herein.

FIG. 19 summarizes the classes of methods and devices for bone fixation and spacing which are presented herein. In accordance with the present invention, devices for bone fixation, spacing and prostheses may also be referred to, for brevity, as bone therapy devices. Likewise, the term prosthesis, implant, and fixture are used interchangeably herein.

As described below, in accordance with the present invention, these devices and their associated methods can be divided into 3 general categories or groups: (I) Self Expandable Implants; (II) Implants Expandable by External Power; and (III) Solid Phase Formation Devices. Devices in accordance with the present invention can be constructed according to the embodiments of each of these groups, and can be employed for either intramedullary or intervertebral applications.

Classes of Bone Fixation Devices and Methods

Group I: Self Expandable Implants.

Self expandable implants and related methods utilize the energy stored within the implant material itself, such that when a holding mechanism or restraining force is released from the implant, the implant material reverts to its original shape and/or diameter. In the preferred embodiments, the material is restrained in a small diameter, for use during implantation, and reverts to a larger diameter after implantation, for fixation of the bone. Implementation of this method is preferred using a material which exhibits shape memory such as Nitinol, taking advantage of the properties of Stress Induced Martensite, although other materials can be used, as well. The holding mechanism utilized can be incorporated into the device or around it.

Group II: Implants Expandable by External Power.

Implants which are expandable by external power utilize energy which does not exist in the device but originates from an outside source, to change the shape of the implant. Numerous different forms of external power can be utilized in accordance with the present invention. In the preferred embodiments, at least four alternative types of external power are contemplated:

(1) Heat. Various materials and/or configurations of material can be used in which the application of external heat to the implant (whether from a mechanical source, or body heat itself) causes a change in shape of the implant. In the preferred embodiments, this results from the properties of the implant materials. In particular, shape memory alloys can be used to cause a device to attain a new shape from a small to a larger diameter.

(2) Balloon Expandable Devices. In a second series of external power embodiments, an expandable balloon is used to change the shape of an implant. In these embodiments, the inflation of a balloon causes plastic deformation of the implant material, resulting in deformation of the device.

(3) Balloon Devices. In a third series of external power embodiments, the implant device is itself a balloon. This balloon device is inflated using hydraulic pressure by the insertion of fluid into the balloon's interior, thereby enlarging the device's diameter. In these embodiments, the pressure of the fluid within the sealed balloon provides the energy to support the balloon in its expanded shape.

(4) External Force Devices. In a fourth series of external power embodiments, a mechanism is utilized for application of force to the implant. In these embodiments, the system is designed such that force is transferred inwards, which acts eccentrically from the implant lumen causing an increase of the implant diameter.

Group III. Solid Phase Formation Devices.

In these devices, a material which solidifies (e.g. by polymerization) is inserted into a balloon, forming a solid which has a new shape. This material can have two-componential cement properties, and can be formed of epoxy or polymer. The material is compressed into the balloon and solidifies by change in temperature or humidity.

As disclosed herein, each of these types of devices and methods can be used for intramedullary or intervertebral treatments. Moreover, while different embodiments of the present inventions are discussed in separate sections below, it will be apparent that the disclosures of each section are meant to supplement each other and interrelate. Accordingly, the disclosures of each of the embodiments provided herein may be further relevant to and supplement the disclosures of other embodiments. As examples of the present inventions, a variety of different bone therapy devices and methods are disclosed in further detail below.

Intramedullary Fixtures

In the intramedullary fixture embodiments of the present invention, a radially-expandable intramedullar fixture is inserted percutaneously into a fractured bone. The fixture is inserted through a hole in the bone which is smaller in diameter than the medullar canal. In the preferred embodiments, the fixture is preferably inserted, using a syringe, through the end of a fractured bone and into the medulla. During insertion, the fixture is maintained in a closed configuration, i.e. a first, reduced diameter. The fixture is inserted so that it extends across the site of the fracture in the bone. When the fixture is properly placed within the bone, the syringe is withdrawn. It is highly preferred that the fixture be placed entirely within the bone, with no outward protrusion.

Once in place, the fixture expands radially outward, assuming an open configuration, i.e. a second, expanded diameter, and anchoring itself in place. Upon expansion, the radially expandable device extends through the bone, across both sides of the fracture, thus functioning as an intramedullary bone fixator. The expanded fixture thus holds the pieces of the broken bone together and provides reinforcement against both axial and lateral forces on the bone. Fixtures as those disclosed herein can be provided and sized for long bones, such as the femur, tibia, fibula, humerus, ulna and radius or for smaller bones, such as a phalanx.

After the fixture has been inserted, the skin wound made by the syringe is closed and allowed to heal over the bone. With the employment of the minimally invasive percutaneous procedure, which excludes all post-implantation communication with a contaminated skin surface, the present invention fixates the fractured bone rapidly, and allows mobilization of the patient's limb in minimal time and with a lower infection risk. Thus, when the fixture is used to repair a broken bone in an extremity (for example, a phalanx fracture in a finger), the patient can begin to move the extremity very shortly after the insertion. Such rapid mobilization promotes healing and reduces muscle atrophy. The patient regains use of the broken bone as quickly as possible. Even more importantly, healing proceeds without the need for extensive physiotherapy, which is typically required after the prolonged periods of immobilization commonly encountered when intramedullar nails known in the prior art are used. Furthermore, since there is no fixture left protruding through the skin after the insertion, post-surgical infection and other complications are reduced.

In the preferred embodiments, the implant is made of bio-compatible metals like Nitinol, titanium, S.S. 316 or suitable polymers. Preferably, after insertion, the radial expansion of the fixture is such that its diameter substantially increases. Thus, the diameter can increase by at least 20%, by 40%, by 50%, or more if desired. This large factor of expansion is advantageous in that during insertion, the unexpanded fixture is narrow enough to fit easily into the bone medulla. In contrast, the fixture expands after placement such that its diameter fills substantially all of the intramedullar cavity (i.e., such that the fixture extends across substantially all of the width of the bone) so that the bone is firmly fixated.

Thus, more generally, the initial size of the fixture maintains a reduced diameter small enough to be passed through a needle so as to be inserted into a bone through a syringe, and is capable of expanding to an expanded diameter large enough to fill substantially all of the intramedullary cavity of the bone in question, for fixation of the bone. The fixture is preferably substantially rod like (i.e. tubular in shape) after expansion.

Fixtures in accordance with preferred embodiments of the present invention generally fixate the bone more firmly than K-wires used for this purpose, as described in the above-mentioned article by Varela and Carr. The fixtures of the present invention require formation of only a single hole in the bone for intramedullar insertion, rather than multiple holes as is the case with K-wires.

In some preferred embodiments of the present invention, the intramedullar fixture comprises a self-expanding structure, as described in Group I above. In the context of the present patent application and the claims, the term "self-expanding" or "self-expandable" is used to refer to types of fixtures and to materials from which such fixtures are fabricated. The term is used herein to mean that once the fixture is inserted into the intramedullary cavity, it expands radially outward due to mechanical force generated by the fixture itself. This mechanical force may be due to potential energy stored in the fixture, for example, as a result of radially compressing the fixture before inserting it into the cavity. Additionally or alternatively, as described below, the fixture may expand due to heat absorbed by the fixture in the intramedullar cavity. As disclosed below, certain preferred configurations and materials are used to provide this self-expanding effect. Intramedullar fixtures in accordance with these preferred embodiments differ from expandable intramedullar fixtures known in the art, which require external application of mechanical force to the fixture to cause the fixture to expand within the intramedullar cavity.

Before introduction into the bone, the self-expanding fixture is preferably compressed radially inward into a closed, reduced diameter configuration and is inserted into the syringe in this closed, reduced diameter configuration. After the syringe is inserted and the fixture is put into place, the syringe is withdrawn, leaving the fixture behind in the bone. The fixture then expands radially outward, to bear against and fixate the bone. Thus, the structure and the material from which it is produced, as described below, should generally be sufficiently flexible to be compressed into the closed, reduced diameter configuration, but rigid enough to fixate the bone firmly in an open, expanded configuration.

In some preferred embodiments of the self-expanding implants, the fixture comprises a resilient or elastic, biocompatible material. Preferably, the resilient or elastic material is a superelastic or shape memory material, for example, Nitinol, or another metal, such as titanium, or else a polymer material. The fixture is fabricated, as is known in the art, so as to exert an outward radial force when compressed.

In other preferred embodiments of this type, the fixture comprises a biocompatible shape memory material, likewise such as Nitinol. Preferably, the material is chosen and prepared, as is known in the art, so that upon compression of the fixture into its closed, reduced configuration, the material assumes a state of stress-induced martensite, wherein it is relatively flexible and elastic. When released inside the bone's intramedullar cavity, the fixture springs back to its desired shape, the open, expanded configuration, and the material assumes an austenitic state, wherein it is substantially rigid and firmly fixates the bone.

The structure of the fixture itself can be formed by tightly rolling together one or more sheets of self-expanding material, preferably superelastic or shape memory material, as described above, to form a generally cylindrical spiral structure. After insertion of the fixture into the intramedullar cavity, the spiral partially unrolls as it expands radially outward, until it has expanded to substantially fill the cavity. Preferably, at least one edge of each of the one or more sheets of the material is bent so as to protrude radially outward from the outer, radial surface of the spiral. As the spiral expands, these protruding edges engage the inner surface of the bone, adjoining the medullar cavity, so as to anchor the fixture firmly in place and prevent sliding or rotation of sections of the bone fixated by the fixture. More preferably, two or more of the edges are bent at different angles, in order to prevent rotation of the bone in either a clockwise or a counterclockwise direction.

In other preferred embodiments of this type, the fixture includes a holding device, for example, a pin, which is fitted into the fixture before insertion of the fixture into the bone. The holding device is fitted into the fixture while the fixture is held mechanically in its compressed, closed configuration and then continues to hold the fixture in this configuration. After the fixture has been inserted and properly placed in the intramedullar cavity, the holding device is withdrawn, and the fixture self-expands radially outward to anchor itself in place and fixate the bone.

As an alternative to a self-expanding implant, the implant can be constructed to be expandable by the application of energy or external power. For example, the shape memory material can be chosen and prepared, as is known in the art, so as to have a critical temperature of approximately 30° C. Thus, at room temperature, the material is normally at least partially in a martensitic state, so that the fixture remains flexible and elastic before its insertion into the bone. When inserted into the bone, the implant becomes exposed to body temperature, at which temperature, the material assumes at least a partially austenitic state, and the fixture is substantially rigid.

In such embodiments, wherein heat is applied to the implant to cause it to expand, instead of, or in addition to the use of body temperature, after the fixture is inserted into the intramedullar cavity and the syringe is withdrawn, an external heat source can be used for the application of heat. This can be accomplished, for example, through a heating probe that is brought into contact with the fixture. The heat causes the fixture to expand radially outward and to become substantially rigid, so as to anchor itself in place and fixate the fractured bone. The heating probe or other heat source is then removed.

In other preferred embodiments of the present invention (whether falling within Group I or Group II), the fixture comprises a tube, made of stiff, resilient material, as described above, and having a plurality of openings through its radial wall, so that the wall has substantially the form of a meshwork. The meshwork preferably comprises a plurality of longitudinal ribs, interconnected by generally arcuate circumferential struts. When the fixture is radially compressed, the struts are bent inward, toward the central axis of the tube. The holding device, preferably a pin, is inserted along the axis and holds the struts in their bent configuration, thus preventing the fixture from expanding. When the pin is removed, with the fixture inside the bone, the struts resume substantially their arcuate shape, with the fixture either self-expanding radially outward, or expanding due to the application of energy, until the fixture engages the inner bone surface adjoining the intramedullar cavity.

Over time, after insertion of the fixture in the intramedullar cavity, bone tissue will tend to grow into and through the openings in the mesh-like wall of the fixture, so that the overall structure of the bone will be strengthened.

In another of the embodiments of the invention, the fixture comprises a plurality of leaves, which are bent so that the inner end of each leaf normally extends radially outward, away from a central, longitudinal axis of the fixture. The leaves are arranged along the axis in a generally spiral pattern, wherein each leaf extends outward at a different angle relative to a reference point on the axis from one or more other leaves that axially adjoin it. Preferably, the outer end of each leaf curves radially inward. Before inserting the fixture into the bone, the fixture is compressed by bending the leaves inward, to form a narrow, generally tubular shape. The holding device, preferably a pin, is then inserted along the axis of the tubular shape, so as to engage and hold the inward curved outer ends of the leaves and prevent their radial expansion. After the fixture has been inserted into the intramedullar cavity, the pin is withdrawn, and the leaves snap back radially outward, engaging the inner bone surface and anchoring the fixture in place.

Alternatively, in other embodiments of the present invention involving the application of external energy, a balloon may be inserted inside the fixture and inflated to expand the fixture. After the fixture is expanded, the balloon is preferably deflated and withdrawn although it can also be left implanted.

In another embodiment of the invention, the same intramedullary bone fixator is made of an inflatable balloon.

In other embodiments of the present invention, the fixture itself comprises a balloon, which is inserted into the intramedullar cavity. The balloon can be formed from a tube of a flexible, biocompatible plastic, for example, Dacron fabric, as is known in the art, sealed shut at a distal end thereof.

This balloon fixture is also preferably inserted using a syringe. After the placement of the syringe in the intramedullary space, a sleeve can be inserted therein, through which the balloon is inserted. Once the balloon is positioned and the sleeve and syringe are taken out, the balloon is inflated and detached of the inflating device which is also taken out. The same procedure can also be performed without a sleeve, with or without a guide wire.

Once the balloon is in place, it is inflated to fixate the bone. This can be accomplished with a biocompatible solidifying fluid under pressure from an external source, causing the balloon to expand radially outward to fixate the bone. The balloon is then sealed, and the external fluid source is disconnected.

Preferably, the solidifying fluid comprises a monomer material that polymerizes within the balloon, or alternatively, a two-component cement, such as an epoxy. Such solidifying fluid materials are known in the art. The fluid's solidification is preferably catalyzed by the increased temperature and/or humidity within the bone medulla.

Alternatively, when a non-solidifying non-compressible fluid is used, if the need should arise, the balloon can be perforated and removed utilizing the same basic technique (albeit in reverse) with which it was inserted.

In some of the preferred embodiments, the balloon can also include an internal structure, for example, resilient longitudinal wires. These wires can be fabricated from metal, and can extend lengthwise down the inner side of the balloon. While the balloon is deflated, the structure holds the balloon in a narrow, elongated, substantially closed configuration, so as to ease the insertion of the balloon into the bone. After the balloon has been inserted and inflated, the structure provides additional mechanical strength to the fixture, especially against shear forces. This gives the balloon the elasticity as well as the strength of a bone fixator, once the balloon is inflated in the intramedullary space.

Preferably, after the balloon is inserted into the bone, the balloon is filled with non-compressible fluid. In the preferred embodiments, the balloon has a valve to prevent fluid from escaping (while also allowing fluid to be released, once desired). Upon filling the balloon with fluid, it expands so that it substantially fills the intramedullar cavity. Preferably, an X-ray image is taken of the bone with the balloon inside (preferably while the balloon is still in a partially or non-expanded state). The balloon's internal structure is then observed in the image to ascertain that the balloon is properly positioned, before fully inflating the balloon with the solidifying fluid. In particular, the longitudinal wires will show up on the X-ray image so that proper positioning can be verified.

In the preferred embodiments of the invention, a metal balloon is utilized which has a unidirectional valve, and which is inflated with a high pressure fluid (preferably saline). The balloon is constructed having longitudinal bars which act as fixational elements, so that when inflated, the fixational elements or bars are compressed against the inner surface of the bone cortex, preventing rotational movement between the broken parts of the bone and preventing bending. This embodiment presents an advantage over standard intramedullar nails as no interlocking is needed due to the fact that the longitudinal rods prevent rotation. The nail may also have a medial longitudinal canal to facilitate performing the insertion procedure over a guide wire. During removal, the retrieval device is mounted on the tip of the implanted nail to open the valve, releasing the high pressure within the nail and allowing device diameter decrease.

Fixtures and methods of bone fixation in accordance with the embodiments of the present invention described herein are advantageous for fixation of fractured long bones or short bones. For example, the fixtures of the present invention may be used for fixation of the bones of the arms, legs, hands or feet. Thus, they may be used for fixation of the phalanges of the fingers or toes, the femur, the humerus, the metacarpals, the metatarsals, the tibia, the fibula, or so forth. It will be appreciated that fixtures in accordance with the present invention can be easily adapted to the necessary size for the broken bone required, by one of ordinary skill in the art.

Spine Fusion

In the preferred embodiment for spine fusion, a hollow syringe is inserted through the back into the intervertebral space using an imaging technique. An intervertebral tissue eroder is then inserted through the syringe lumen. Each embodiment is provided with an eroding element for eroding soft tissue in its vicinity. The device can come in the design of a brush or a spinning wire, to which might be attached an eroding element, such as an orb with cutting edges. Rotation of the eroding element, whether the brush, the spinning wire or the orb, causes erosion of soft tissue in the eroding element's vicinity. Upon eroding the soft tissue, the intervertebral tissue extractor then sucks out or removes the eroded intervertebral tissue, creating a space into which the intervertebral spacer, together with a bone graft, is inserted. The suction or removal is achieved by use of a vacuum through the longitudinal central lumen of the extractor's rotating shaft or any other desired lumen. Suction or removal can also be effected by a screw within the same lumen that would spin in the opposite direction of the extraction device or which stays as is and takes up and out the tissue remains.

The insertion of the intervertebral spacer (also referred to herein as an intervertebral cage), like the insertion of the intervertebral tissue extractor, is made through the hollow syringe lumen, circumventing the need for exposing the vertebra with subsequent invasive surgery.

Once in the intervertebral space and out of the insertion syringe, the intervertebral spacer expands in diameter due to its self-expandable properties, or is expanded with an expander, thus fixating and supporting the spine. Due to its porous design, the spacer further enables bone fusion of the two adjacent vertebrae, assisted by bone graft interposition with or without bone growth factors.

Intravertebral Disc Prostheses

In additional embodiments of the present inventions, a disc prosthesis is provided which comprises a balloon made of a biocompatible fabric. The balloon has an inlet port which is connected to an inflation tube. Preferably the fabric comprises inert, synthetic material, such as Dacron or Gore-Tex. Alternatively or additionally, the fabric may comprise bioabsorbable material, as is known in the art, or a combination of inert and bioabsorbable materials. Further preferably, the prosthesis includes a strong, resilient reinforcing structure, for example, stainless steel wires interwoven with the fabric. Further, the balloon can have a thin wall of metal, the balloon being compressed when inserted and expanded (in the upward and downward direction) during inflation. Further, the disc prosthesis can be made of a complex of inflatable elements interconnected so that, when inflated, it expands radially and up and down, with space provided between the tubes to allow bone growth.

After removal of some or all of the disc matter of an injured disc from the intervertebral disc space of a patient, the balloon is inserted into the disc space. (In the context of the present disclosure, the balloon prosthesis is referred to interchangeably either as the balloon or as the prosthesis.) The balloon is inserted in an at least partially deflated state, preferably completely deflated, in which state it preferably assumes a narrow, elongate shape, through a percutaneous cannula. After the balloon has been properly positioned in the disc space, a biocompatible solidifying fluid, for example, a bone cement or, alternatively, a polymerizing monomer, as are known in the art, is injected through the inflation tube to inflate the balloon. Once the fluid has hardened, the balloon remains firmly in place between the vertebrae adjoining the disc space and holds the vertebrae permanently at an anatomically suitable orientation. Also, a high pressure non-compressible fluid can be used to keep the prosthesis in its expandable state.

Preferably, before the prosthesis is inserted into the disc space, the disc matter is removed and the bone surfaces adjoining the disc space are cleaned using a percutaneous electrocautery probe. Alternatively, the disc matter may be removed and the bone surfaces may be cleaned using diskectomy methods and devices known in the art.

Preferably, the fabric is woven so as to have a roughened, porous surface, which encourages ingrowth of the vertebral bones adjacent to the prosthesis into the fabric. Such ingrowth forms a tight bond between the bone and the prosthesis. Further preferably, ground bone matter, taken, for example, from the patient's pelvic bone, is spread on the surface of the fabric, to further encourage bone growth. Eventually, the two vertebrae on the opposite sides of the prosthesis will generally grow around and through the prosthesis and fuse together. During the period of bone growth, the presence of the prosthesis holds the vertebrae at a suitable distance and mutual orientation.

In some embodiments of the present invention, the balloon comprises two circular pieces of the fabric having a diameter approximately equal to the diameter of the disc space in which the prosthesis is to be implanted. The two pieces of fabric can be laid one on top of the other and then sealed together around their outer edges and at their centers. An inflation tube is attached and sealed to the fluid port, which is located between the two pieces of the fabric at a point along the outer edges thereof.

To insert the balloon into the disc space; the balloon is rolled up about an axis parallel to the inflation tube. The rolled-up balloon has the shape of a long, narrow cylinder. In this shape, the balloon is passed through the cannula into the disc space, preferably using the same cannula through which the electrocautery probe or other surgical tool was previously passed to clean the disc space of disc matter. Once inside the disc space, the balloon is allowed and/or caused to unroll.

The balloon is then filled with the solidifying fluid via the inflation tube, so that the balloon assumes a generally toroidal shape. The major diameter of the toroid, extending radially across the disc space, is, preferably, approximately equal to the diameter of the disc that the prosthesis has replaced. The minor diameter, extending axially between the two vertebrae adjoining the disc space, is controlled by increasing the inflation pressure of the fluid in the balloon until the vertebrae are held stably at the anatomically correct mutual spacing. Once the fluid has begun to solidify, the inflation tube is first sealed off and then withdrawn through the cannula.

Alternatively, in other embodiments of the present invention, the prosthesis may comprise a balloon of any other suitable size and/or shape, for example, an ellipsoidal or crescent shape. Furthermore, two or more such balloons, of substantially smaller diameter than the radial diameter of the disc space, may be implanted and inflated side-by-side. Such smaller balloons are advantageous in that they are generally easier to insert and manipulate through the cannula than a single, larger balloon.

In some embodiments of the present invention, after the prosthetic balloon is inserted in the disc space, but before it is inflated with the solidifying fluid, the balloon is inflated with a gas, for example, sterile air or carbon dioxide. The position of the balloon in the disc space is then visualized, to verify that it is properly placed and to correct its positioning, if necessary. Once these steps are completed, the balloon is deflated of gas and then inflated with the solidifying fluid or with high pressure fluid.

Various methods may be used for visualizing the implantation of the balloon. Preferably, the entire procedure of percutaneous spinal treatment is performed under open magnetic resonance imaging, as is known in the art. Alternatively or additionally, an endoscope, likewise known in the art, may be inserted into or adjacent to the disc space, preferably through the same cannula that is used for insertion of the prosthesis. Further alternatively, when the balloon includes a radio opaque element, for example, the stainless steel reinforcement wires described above, the position of the balloon may be visualized using X-ray imaging, in which the radio-opaque element is visible.

The disc prosthesis can also be constructed as a metal hollow member which is able to change its volume by high pressure fluid insertion. This metal disc is provided with protrusions in its upper and lower surfaces so as to stick and/or penetrate up and down into the vertebral bone surface. This prevents disc movement and achieves better stabilization until bone fusion is achieved.

In one embodiment, cylindrical shaped tubes are inserted percutaneously. In another embodiment, a donut-shaped (i.e. toroidal) disc is inserted and the inner space is filled with a bone graft. In another embodiment, a tri-dimensional honeycomb shaped structure is created, preferably for expansion using multi-tubed inflation. This honeycomb shaped structure preferably has open cells, facilitating bone ingrowth through the structure.

All of these embodiments can be filled with soldifying fluid or non-compressible fluid. If non-compressible fluid is used, it is preferred that a valve be provided so that the fluid remains at high pressure during use, but can be released from the structure, for deflation if desired. If desired, the device used to remove the prosthesis can attach to the valve to allow release of fluid therefrom.

Although embodiments of the present invention are described with reference to minimally invasive, percutaneous spinal treatment, it will be appreciated that disc prostheses in accordance with the principles of the present invention may similarly be implanted using other surgical methods known in the art.

Remotely Activated Prosthesis

In accordance with the present invention, prostheses are disclosed which allow remote activation after implantion of the prosthesis within the body. The remote activation is used to increase the size of the prosthesis, eliminating the prosthesis loosening effects which develop over time, and thereby eliminating the need for additional surgery as is currently the treatment in the art. The invention is particularly suited for bone prosthesis, such as those disclosed in the present application.

To address the problems of the prior art, a prosthesis is provided having an inflatable member included therein. The chamber has an inner lumen and a shape allowing the chamber to expand in size from a compressed to an expanded configuration. For example, the walls of the chamber can be provided in a curved or undulated construction, which allows initial compression of the chamber in a small sized state, and later expansion into a larger state, by straightening out of the curves. The chamber has a magnet coupled to any appropriate or suitable gear means, as will be apparent to those of ordinary skill in the art. An external unit, such as a rotating magnet or an MRI machine, produces a magnetic field, which is coupled to the implanted magnet from a distance. The magnetic field produced by the external unit causes rotation of the implanted magnet within the inflatable member, causing the magnet to move against a portion of the inflatable member, exerting an internal force which causes the inflatable member to expand. The external field can be applied for a desired duration, to cause the degree of size increase desired, from a partial to a total increase in the potential size of the inflatable member.

When implanted within a prosthesis or fixture, the inflatable member is initially maintained in the compressed position. Expansion of the inflatable member (by use of the external magnetic field, as described above) causes the inflatable member to increase in size due to the force exerted by the internal magnet against the inner walls of the prosthesis. This expansion of the inflatable member exerts pressure against the internal non-compressible fluid of the prosthesis, which causes the prosthesis to likewise expand in size. Expansion of prosthesis nail diameter, in turn, eliminates the loosening problem known in the prior art. The expanded diameter intramedullar nail fits more snugly against the bone, such that loosening has been eliminated.

In the preferred embodiment, the prosthesis is further provided with a pressure gauge having a radioopaque dial. The radioopaque dial has a scale which illustrates the pressure within the prosthesis, thereby illustrating the post implantation size of the prosthesis. The radioopaque dial and scale are readable using an X-ray machine. Thus, the relative diameter or size of the prosthesis can be determined after prosthesis implantation in the bone, without the need for a surgical or an invasive procedure, by using a conventional X-ray machine. By taking an X-ray of the bone, the physician can determine the relative diameter of the prosthesis in the bone by reading the radioopaque readout of the pressure gauge directly off of the X-ray film itself. If desired, the physician can then activate the external unit to expand the prosthesis and adjust the expansion of the prosthesis to the desired level, by checking the X-ray results.

Electrocautery Probe

In preferred embodiments of the present invention, an electrocautery probe used for resection comprises a shaft and a wire loop for resecting tissue. The wire loop protrudes from a side of the shaft, rather than from the distal end of the shaft as is known in the art. Probes made in accordance with the present invention have the advantage that the size of the wire loop can be enlarged and reduced to allow insertion of the loop to various locations within a patient's body, without damaging sensitive tissue within the body.

In some preferred embodiments of the present invention, the wire loop protrudes from a recess in the shaft. Thus, it is possible to reduce the size of the wire loop until it is entirely within the recess.

Preferably a suction channel runs along the probe, allowing suction of smoke and resected tissue. Alternatively or additionally, the probe is passed into the body through a sleeve or a cannula, and the space between the probe and the sleeve or cannula is used for suction and/or water irrigation.

In some preferred embodiments of the present invention, the probe described above is used in a TURP procedure. The probe is rotated about a long axis thereof, so that resection is performed using primarily rotational motion of the probe rather than primarily longitudinal motion as in the prior art. The wire loop of the electrocautery probe is positioned in a first section of the prostatic urethra, preferably, the most distal section of the prostatic urethra. A power source, which passes RF current through the wire loop, is activated so as to resect tissue of the prostate gland in the distal section. The probe is rotated around its axis to smoothly resect a ring-shaped layer of the prostate gland. The wire loop is gradually enlarged and the probe is rotated until a sufficient amount of the prostate gland in the distal section has been resected.

The size of the wire loop is then decreased, and the probe is moved proximally to a second section of the prostatic urethra, adjacent the first section. The wire loop is again enlarged and the probe rotated to resect the second section. This process is repeated section after section, until substantially all of the prostatic urethra has been sufficiently resected. It will be appreciated that in this procedure, the danger of damaging the urethral sphincter is reduced since longitudinal movement of the probe is minimized, and the wire loop is positioned at the proximal end of the prostatic urethra only once.

In other preferred embodiments of the present invention, an electrocautery probe, preferably as described above, is used in percutaneous diskectomy to resect disc tissue of a herniated or protruding disc. The probe is inserted percutaneously into the herniated disc. Preferably, the position of the wire loop is confirmed by fluoroscopic, ultrasonic or magnetic resonance imaging, or by endoscopic imaging, as are known in the art. The electric power of the wire loop is then operated, and the herniated disc material is resected. The loop is enlarged as the tissue is resected, and the probe is repeatedly rotated in order to evenly resect the tissue.

It will be appreciated that in different cases, varying amounts of tissue may be resected. For example, in some cases only part of the disc nucleus is resected, whereas in other cases, substantially all of the nucleus is to be resected. According to the amount of tissue which is to be resected, the surgeon determines the duration of the resection procedure and the maximal loop size used. It will be appreciated that if necessary, the resection procedure can resect substantially all of the disc tissue between the adjacent vertebrae. The wire loop can be enlarged in order to fit into substantially all corners and angles of the disc space.

In preferred embodiments of the present invention, the length of the wire loop is varied dependent on the radial orientation of the probe, so that when the probe is turned, the length of the loop changes. When the probe is used within the disc space, the probe is set such that the wire is lengthened when the loop is oriented sideways, i.e., within the plane of the disc, and the wire is shortened when the loop is oriented up or down, toward the vertebrae.

Preferably, a suction tube, located within the probe or, alternatively, surrounding the probe, is operated during the resection in order to extract smoke and resected disc tissue. Further preferably, a water channel is inserted into the disc space along with the probe, and water irrigation is used to wash out the resected disc parts during resection. Preferably, the water is removed through the suction tube.

The diskectomy procedure according to the principles of the present invention enables thorough resection of the intervertebral disc and of the periosteum, a procedure which is very difficult to perform percutaneously with current technology. Furthermore, the method of the present invention results in more thorough cleaning of the disc space and vertebral bone surfaces adjacent thereto, so that a prosthetic disc may be more easily and successfully implanted. Preferably, the prosthetic disc is also inserted percutaneously, subsequent to the diskectomy, as described, for example, in Israel Patent Application No. 119513 and in a U.S. Provisional Patent application filed Mar. 7, 1997, entitled "Intervertebral Disc Prosthesis," both of which are assigned to the assignee of the prescent application, and whose disclosures are incorporated herein by reference.

Therefore, there is provided in accordance with a preferred embodiment of the present invention, an electrosurgical probe having a distal end and including an elongate shaft and a wire loop protruding radially from the shaft, wherein an electrical current is passed through the wire loop to resect tissue.

In the preferred embodiments of the invention, a variety of features are provided. The wire loop does not protrude beyond the distal end of the shaft, and the size of the wire loop is controllably variable. The probe defines a recess in an outer radial surface of the shaft, and the size of the wire loop is controlled so that the loop is contained within the recess. The wire loop includes a portion of a wire running through the shaft, and the size of the wire loop is controlled by adjusting the length of the wire fed into the shaft. The size of the wire loop is adjusted responsive to a rotational orientation of the probe. The probe is contained in a sleeve having an opening at a distal end thereof through which the wire loop protrudes, and the size of the wire loop is dependent on the orientation of the probe relative to the sleeve. It is also preferred that the probe include a working channel running along the length of the shaft and communicating with an opening adjacent the distal end of the probe. The wire loop is rotated about a longitudinal axis of the probe during resection. The electrical current used is preferably an RF current.

There is also provided in accordance with a preferred embodiment of the present invention, a method of resecting a urinary obstruction due to enlargement of the prostate gland of a subject including inserting an electrosurgical probe comprising a wire loop through the urethra of the subject to a section of the prostate gland, passing current through the wire loop to resect tissue adjacent thereto, and rotating the probe about a longitudinal axis thereof to produce a channel through the section of the prostate gland.

In the preferred embodiments, the method includes enlarging the wire loop and continuing to rotate the probe to increase the diameter of the channel. The probe is then moved in an axial direction to another section of the prostate gland with repetition of the preceding steps. These steps are repeated until a channel has been produced through the entire prostate gland. Moving the probe to another section includes moving the probe proximally and/or distally.

There is also provided in accordance with a preferred embodiment of the present invention, a method of removing tissue from a herniated disc using an electrosurgical probe including a wire loop, including bringing the probe into contact with the tissue, and passing current through the wire loop to resect the tissue.

In the preferred embodiments, bringing the probe into contact with tissue includes inserting the probe into an intervertebral space. Preferably, the probe is inserted into the intervertebral space percutaneously. The disc has an annulus and a nucleus, and passing current through the wire loop to resect the tissue includes resecting the nucleus. The method includes rotating the probe, and changing the size of the loop during resection, if desired. Changing the size of the loop includes changing the size of the loop responsive to the rotational orientation of the probe, and includes enlarging the loop when the probe is oriented so that the loop is in a plane generally parallel to the surface of a vertebra adjacent the disc, and reducing the size of the loop when the probe is oriented so that the loop is generally perpendicular to the plane. The method also includes applying suction to an area in proximity to the wire loop when current is passed through the wire loop.

BRIEF DESCRIPTION OF THE DRAWINGS

FIG. 1 is a schematic, isometric view of a self-expanding intramedullar fixture, in accordance with a preferred embodiment of the present invention.

FIG. 2A is a schematic, sectional illustration showing a self-expanding intramedullar fixture in a first, closed configuration, in accordance with a preferred embodiment of the present invention.

FIG. 2B is a schematic, sectional illustration showing the fixture of FIG. 2A in a second, open configuration, in accordance with a preferred embodiment of the present invention.

FIGS. 3A–3C are schematic, sectional illustrations showing the use of the fixture of FIG. 1 in fixation of a fractured bone, in accordance with a preferred embodiment of the present invention.

FIG. 4A is a schematic, isometric representation of another self-expanding intramedullar fixture, in an open configuration, in accordance with a preferred embodiment of the present invention.

FIG. 4B is a schematic, sectional illustration showing the fixture of FIG. 4A in a closed configuration, wherein a holding pin is inserted along a central axis of the fixture, in accordance with a preferred embodiment of the present invention.

FIG. 5A is a schematic, end view of still another self-expanding intramedullar fixture, in an open configuration, in accordance with a preferred embodiment of the present invention.

FIG. 5B is a schematic illustration showing preparation of material for fabrication of the fixture shown in FIG. 5A, in accordance with a preferred embodiment of the present invention.

FIG. 5C is a schematic, sectional view of the fixture of FIG. 5A, in a closed configuration with an internal holding pin, in accordance with a preferred embodiment of the present invention.

FIG. 6 is a schematic representation of an intramedullar balloon fixture, in a non-inflated state, in accordance with a preferred embodiment of the present invention.

FIGS. 7A–7D are schematic, sectional illustrations showing the use of the fixture of FIG. 6 in fixation of a fractured bone. The figures illustrate the steps of insertion of the fixture, inflation of the balloon and removal of the inflation mechanism.

FIGS. 8A and 8B are side and sectional views, respectively, of an inflatable intramedullar fixture, in a deflated configuration, in accordance with a preferred embodiment of the present invention.

FIGS. 9A and 9B are sectional and isometric views, respectively, of an inflatable intramedullar fixture, in an inflated configuration, in accordance with a preferred embodiment of the present invention.

FIGS. 10($a$)–($d$) are perspective views showing two devices for bone fixation in open and closed positions, in accordance with a preferred embodiment of the present invention. These devices can be opened by a transfer of heat (e.g. if they are constructed from shape memory material), can be opened by use of a balloon, or by any additional suitable mechanical method. FIGS. 10($a$) and ($b$) are illustrations of a first embodiment of the device, shown in compressed and expanded configurations respectively. FIGS. 10($c$) and ($d$) are illustrations of a second embodiment of the device, shown in compressed and expanded configurations respectively.

FIG. 11 is a schematic cross sectional illustration of a bone fixation device whose height can be mechanically varied, in accordance with a preferred embodiment of the present invention. It is shown in closed (FIG. 11$a$) and open (FIG. 11$b$) configurations. The device can include hinges at its joints or joints that undergo plastic deformation.

FIG. 12 is a schematic isometric view of an expandable intervertebral spacer and intramedullar bone fixator, in accordance with a preferred embodiment of the present invention. The design is shown in the figure without a locking finger and with multiple surface openings.

FIG. 13A is a schematic cross sectional view of an intervertebral bone spacer and intramedullar bone fixator, in accordance with a preferred embodiment of the present invention.

FIG. 13B is a schematic cross sectional view of the device of FIG. 13A, shown in its compact, reduced diameter state for insertion.

FIG. 13C is a sectional view of a modified version of the device of FIGS. 13A–B, shown in its expanded state, with multiple locking mechanisms.

FIG. 14A is a schematic, top view of an intervertebral disc prosthesis, in accordance with a preferred embodiment of the present invention.

FIG. 14B is a schematic, cross-sectional view of the prosthesis shown in FIG. 14A.

FIG. 15 is a schematic, isometric illustration showing the insertion of the prosthesis of FIGS. 14A and 14B into the intervertebral disc space of a patient, in accordance with a preferred embodiment of the present invention.

FIG. 16 is a schematic, sectional view in a coronal plane, showing the placement of the prosthesis of FIGS. 14A and 14B in the disc space, in accordance with a preferred embodiment of the present invention.

FIG. 17A is a schematic, sectional view in the coronal plane of FIG. 16, showing the inflation of the prosthesis of FIGS. 14A and 14B, within the disc space, in accordance with a preferred embodiment of the present invention.

FIG. 17B is a schematic, sectional view in an axial plane through the disc space, illustrating the inflated prosthesis as shown in FIG. 17A; and FIGS. 18A, 18B and 18C are respectively a sectional view, a top view and an isometric view of a disc prosthesis (with a portion of an inflator mechanism), in accordance with another preferred embodiment of the present invention.

FIG. 19 is a chart summarizing the various methods and devices for bone fixation and intervertebral spacing, in accordance with the preferred embodiments of the present invention.

FIG. 20 is a schematic illustration of an intervertebral tissue eroder and extractor, in accordance with a preferred embodiment of the present invention. FIG. 20a shows an embodiment of the brush design with vacuum suction. FIG. 20b shows an embodiment of the brush design with the screw suction. FIGS. 20c–e show the length adjustable spinning wire eroder: plain (FIG. 20c), with an orb having sharp edges (FIG. 20d), and with the orb having sharp edges threaded like a bead (FIG. 20e), respectively.

FIG. 21 is a perspective view of an electro-surgical probe, as is known in the art.

FIG. 22 is a sectional view illustrating use of the electro-surgical probe of FIG. 21 in a TURP procedure, as is known in the art.

FIG. 23 is a sectional view of an electro-surgical probe, in accordance with a preferred embodiment of the present invention.

FIG. 24 is a cross-sectional and schematic view of an electro-surgical probe, in accordance with another preferred embodiment of the present invention.

FIGS. 25A–5D are sectional views illustrating a method of TURP surgery using the electro-surgical probe of FIG. 23, in accordance with a preferred embodiment of the present invention.

FIG. 26 is a perspective view illustrating the use of the probe of FIG. 24 in resecting disc tissue, in accordance with a preferred embodiment of the present invention.

FIG. 27A is a schematic view of an electrosurgical probe at a first orientation within a disc space, in accordance with a preferred embodiment of the present invention.

FIG. 27B is a schematic view of the electro-surgical probe of FIG. 27A at a second orientation within the disc space, in accordance with a preferred embodiment of the invention.

FIG. 28 depicts views of additional preferred embodiments of an intramedullar fixation device. FIG. 28A is a perspective view of this intramedullary fixture. FIG. 28B is a cross sectional view of the intramedullary fixture of FIG. 28A. FIG. 28C is a schematic, partial side view of the intramedullary fixture of FIGS. 28A and 28B.

FIG. 29 depicts views of additional preferred embodiments of an intramedullar fixation device having a valve. FIG. 29A illustrates a longitudinal cross section of the device. FIG. 29B illustrates a cross sectional view of the device of FIG. 29A, the device being shown in the compressed configuration, with the view being taken in cross section along line A—A of FIG. 29A. FIG. 29C illustrates a cross-section of the expanded configuration of the device of FIG. 29B, also taken along line A—A of FIG. 29A.

FIG. 29D is an additional embodiment of the device shown in FIGS. 29A–C. The device is further provided with a fixed diameter segment which is located in the area of a fracture.

FIG. 30A presents two cross sectional views of another embodiment of the intramedullar nail invention. Cross sectional views of both the constricted and expanded configurations or states are shown in the figure, with these constricted and expanded configurations being superimposed for comparison purposes.

FIG. 30B presents two cross sectional views of another embodiment of the intramedullar nail invention. As in FIG. 30A, cross sectional views of both the constricted and expanded configurations or states are shown superimposed for comparison purposes.

FIG. 31 illustrates the medial longitudinal canal which can be provided as an additional embodiment of the invention. The canal is provided for location of the fixture on a guide wire to facilitate positioning. FIG. 31A is a perspective view of the fixture, having the canal therein, and FIG. 31B is a schematic of the fixture, showing the canal extending therethrough.

FIG. 32a is a schematic cross section of an inflatable member for insertion into a prosthesis, in accordance with the present invention, and an external activating unit, also shown schematically by FIG. 32 for use outside the body, for use to activate and expand (or retract) the inflatable member.

FIG. 33 is a schematic cross section of the inflatable member of FIG. 32, after expansion.

FIG. 34 is a schematic cross sectional comparison of the inflatable member of the present invention in "before" (compressed) and "after" (expanded) states. The figure illustrates and compares the compressed inflatable member with the expanded inflatable member, the expansion of the inflatable member having been used to cause an increase in the size of the prosthesis.

FIG. 35 is a schematic cross sectional illustration of an intramedullar nail within the bone, the nail having been loosened over time.

FIG. 36 is a schematic cross sectional illustration of the intramedullar nail of FIG. 35, after activation of the inflatable member to increase the diameter of the intramedullar nail, making it fit tightly against the inner surface of the bone cortex, thereby eliminating the loosening illustrated in FIG. 35.

FIG. 37 is a schematic of a preferred embodiment of the present invention, illustrating the inflatable member within a prostheis, the prosthesis being further provided with a radioopaque pressure dial to monitor and check the prosthesis diameter, and for use in guaging and setting the level of desired expansion.

DETAILED DESCRIPTION OF THE INVENTION AND THE PREFERRED EMBODIMENTS

Features of the invention are further illustrated by reference to the figures, the following description and the claims, which provide additional disclosure of the invention in various preferred embodiments.

FIG. 1 is a schematic, isometric representation of a self-expanding intramedullar fixture 20, in accordance with a preferred embodiment of the present invention. Fixture 20 is preferably constructed of two sheets 22 and 24 of resilient, biocompatible material, preferably a superelastic material or a shape memory material, as is known in the art. Nitinol is preferred. Alternatively, the fixture may be constructed from another biocompatible metal, such as titanium, or a plastic or polymer material.

Sheets 22 and 24 are initially rolled tightly together into a cylindrical form. Each sheet of this compacted form is tightly rolled (as generally shown in FIG. 2A), and fixture 20 is inserted, in this compacted form, into the intramedullar cavity of a bone (FIG. 3B), as described below. When the fixture is then released inside the bone, the resilience of sheets 22 and 24 causes them to partially unroll into an expanded state (as generally shown in FIG. 2B), so that fixture 20 expands radially outward to assume an increased diameter, as shown in FIG. 1.

Preferably, outer edges 26 and 28 of sheets 22 and 24, respectively, are formed so that when fixture 20 is released inside the bone, the edges bend radially outward, as shown in FIG. 1. Edges 26 and 28 will then engage an inner surface of the bone surrounding the intramedullar cavity, so as to hold fixture 20 firmly in place and prevent sliding or rotation of the bone relative to the fixture. Preferably, edge 26 is bent at an acute angle, and edge 28 is bent at an oblique angle, as shown in the figure, so that fixture 20 resists rotation in both clockwise and counterclockwise directions about its axis 30.

FIGS. 2A and 2B are schematic, sectional representations of a self-expanding intramedullar fixture 36, similar to fixture 20, illustrating the principle of radial self-expansion of such fixtures, in accordance with a preferred embodiment of the present invention. For simplicity of illustration, fixture 36 comprises only a single sheet 38 of self-expanding material, preferably resilient material. It will be understood that intramedullar fixtures based on the principles of the present invention, as exemplified by fixtures 20 and 36, may comprise one, two, or more sheets of self-expanding material, rolled together as shown in FIGS. 1, 2A and 2B.

FIG. 2A shows fixture 36 in a first, closed configuration, in which the fixture is compressed radially inward to facilitate its insertion into the intramedullar cavity of a fractured bone, as described below. For fixation of phalanx bones of the fingers, for example, fixture 36 preferably has an outer diameter of only about 2 mm in this closed configuration. FIG. 2B shows fixture 36 in a second, open configuration, which the fixture assumes after location within the cavity to fixate the bone. Preferably, the diameter of fixture 36, in the open configuration of FIG. 2B, is at least 50% greater than the diameter in the closed configuration of FIG. 2A. More preferably, the diameter in the open configuration is approximately twice the diameter in the closed configuration. In the case of phalanx bone fixation, for example, the diameter in the open configuration is preferably approximately 4 mm. The large diameter difference between closed and open configurations is advantageous in that it facilitates insertion of fixture 36 into the bone in the closed configuration through a hole of minimal size made at or near the end of the broken bone.

As described above with reference to fixture 20, sheet 38 preferably comprises a superelastic material, preferably Nitinol, having a thickness of about 0.2 mm. The superelasticity of sheet 38 causes fixture 36 to expand until outer edges 39 of the sheet engage the inner bone surface surrounding the intramedullar cavity, to exert strong outward radial force on the bone.

Sheet 38 may comprise shape memory material, such as Nitinol, which is produced, as is known in the art, so as to have the open form shown in FIG. 2B and to be normally in the austenitic state at body temperature. In the closed configuration shown in FIG. 2A, however, the force exerted in rolling up sheet 38 preferably causes the material to assume a state of stress-induced martensite. In this state, the material is relatively flexible and elastic, making it easier to insert fixture 36 into the bone. Once the fixture has expanded inside the bone to the open configuration shown in FIG. 2B, however, the stress on sheet 38 is reduced, and the material reverts to its normal, substantially rigid austenitic state. The rigidity of the material in this state facilitates firm fixation of the bone.

Additionally or alternatively, the shape memory material may have a critical temperature in the range between room temperature and body temperature, preferably around 30° C. As described above, the shape memory material is formed so that in its austenitic state (i.e. above the critical temperature), it has substantially the open, expanded form shown in FIG. 2B. Below the critical temperature, i.e. before insertion or fixture 36 into the bone, the shape memory material is in a martensitic state, in which it is relatively flexible and elastic and is compressed into the closed configuration shown in FIG. 2A. When the fixture is inserted into the bone, it is warmed (e.g. by body heat) to above the critical temperature, whereupon it opens and assumes its substantially rigid, austenitic state. A heating element may be brought into contact with the fixture once it is inside the bone, for example, as illustrated in FIG. 3B and described below, to hasten its expansion and state change.

FIGS. 3A–3C are schematic, sectional illustrations showing the insertion of a fixture 20 into intramedullar cavity 40 of a fractured bone 42, in accordance with a preferred embodiment of the present invention. Although described with reference to a phalanx bone, it will be appreciated that devices and methods in accordance with the principles of the present invention may be applied in the fixation of other long bones (e.g. the humerus), with appropriate adaptations for the differences in size and mechanical strength required of the bones, as will be apparent to one of ordinary skill in the art.

As shown in FIG. 3A, a stylette 46 is inserted into a lumen 47 within a cannula 48. For fixation of phalanx bones, cannula 48 preferably comprises a syringe needle. Stylette 46 and cannula 48 are then introduced percutaneously into intramedullar cavity 40 through an opening 45 at the end of bone 42, and past a fracture site 44 in the bone.

Alternatively, a small incision may be made through the skin and soft tissues, to visualize the bone, and a hole may be drilled in the bone for insertion of the cannula therethrough. Drilling such a hole is the preferable method for inserting fixtures, in accordance with some preferred embodiments of the present invention, particularly for larger bones, such as the humerus. Drilling the hole before inserting the fixture also makes it easier to remove the fixture, if desired, after the bone has healed.

As shown in FIG. 3B, once cannula 48 is properly in place, stylette 46 is withdrawn, and fixture 20, in its compressed, closed configuration, is passed into lumen 47 of the cannula. Preferably, a plunger 43 is used to push the fixture into the needle and hold it in place. Cannula 48 is then fully withdrawn, leaving fixture 20 in cavity 40, with the fixture extending across fracture site 44.

Fixture 20 then expands or is expanded to substantially fill cavity 40, as shown in FIG. 3C. The fixture self expands in the self expandable embodiments disclosed herein. Alternatively, in other embodiments, as disclosed below, the fixture is expanded using external force or energy.

The self-expansion of the fixture forces curved edges 26 and 28 of sheets 22 and 24 (or 39 of fixture 36) radially outward against inner surface 49 of bone 42 across both sides of fracture site 44. This force anchors the fixture in place and prevents relative motion of the sections of the fractured bone. In some preferred embodiments of the present invention, wherein sheets 22 and 24 comprise shape memory material as described above, plunger 43 may optionally comprise a heating element for heating fixture 20 to above the critical temperature.

After fixture 20 is positioned and anchored firmly in place, plunger 43 is withdrawn through opening 45, and the skin wound made by or for cannula 48 is allowed to close. Within a short time after completion of the procedure illustrated in the figures, the subject is able to mobilize fractured bone 42. The mechanical strength of fixture 20 also reinforces the bone against axial and lateral forces that may be exerted on the bone. Moreover, the risk of post-operative infection is minimized since no surgical devices or appliances are left protruding through the skin, in contrast to the expandable intramedullar fixtures known in the art. If desired, the device can be covered with a sheath so as to prevent bone ingrowth and facilitate subsequent device removal.

FIG. 4A is a schematic, isometric view of another self-expanding intramedullar fixture 50, in accordance with another preferred embodiment of the present invention. Fixture 50 comprises a plurality of longitudinal ribs 52, connected by a plurality of circumferential struts 54. Ribs 52 and struts 54 preferably comprise resilient material, preferably superelastic material, or alternatively, shape memory material as described above. FIG. 4A shows fixture 50 in a substantially open configuration, which the fixture assumes when it is located inside the bone and allowed to expand.

FIG. 4B is a schematic, sectional illustration, showing fixture 50 in a closed or constricted configuration for insertion of the fixture into the bone. To compress the fixture into this closed configuration, a long, cylindrical holding pin 56 (seen in sectional view in FIG. 4B) is inserted gradually along central axis 30 of the fixture. As pin 56 is inserted, each circumferential strut 54 is, in turn, bent inward across axis 30. Pin 56 passes through and "captures" or locks the struts in place as they are bent, thus preventing the struts from snapping back to their outward circumferential position. As struts 54 are bent inward and captured by pin 56, ribs 52 are drawn inward as well, as shown in FIG. 4B. By passing pin 56 along the entire length of axis 30 through fixture 50, the fixture is brought into the closed configuration, wherein its outer diameter is substantially reduced. Preferably the diameter or dimension of the fixture in the closed configuration of FIG. 4B is reduced to no more than half the diameter in the open configuration shown in FIG. 4A.

Once fixture 50 has been inserted into the intramedullar cavity of a bone (for example, cavity 40 of bone 42, as illustrated in FIGS. 3A–3C), pin 56 is removed. Upon removal of the pin, struts 54 spring back to their original, circumferential positions, and the fixture resumes the open configuration shown in FIG. 4A.

As described above, fixture 50 may, if desired, be made of shape memory material, which in its normal, austenitic state maintains the open configuration with substantial rigidity. As struts 54 are bent, they assume a state of stress-induced martensite, returning to the austenitic state when the stress is removed as pin 56 is removed. As discussed above, if desired, this device can be covered with a sheath or sleeve (such as an expandable flexible polymer) to prevent bone ingrowth.

As a further embodiment to those described above, another self expandable bone fixator is shown in FIG. 5. The preferred material for this device is Nitinol, although the device can also be made from a polymer, stress-induced martensite (SIM), smooth tin, or other suitable materials.

In accordance with a preferred embodiment of the present invention, FIG. 5A is a schematic, end view of this self-expanding intramedullar fixture 60 in an open configuration. Fixture 60 is preferably formed of resilient material, more preferably superelastic material, as described above. The fixture comprises a plurality of leaves 62, 66, 68, 70, 72, 74, 76 and 78, extending radially outward in a spiral pattern about axis 30 of the fixture, the leaves extending from a central, generally tubular portion 63. As shown in the figure, each of the leaves extends outward at a different angle about axis 30 (as measured off of a single reference line, not shown, extending from the axis to a point located at 0 degrees on the circumference). In the expanded configuration of FIG. 5A, the leaves engage the inner surface of the intramedullar cavity of a fractured bone (for example, surface 49 of cavity 40, as shown in FIGS. 3A–3C), in order to hold fixture 60 in place and fixate the bone. Each of the leaves has a base 67, which forms a part of tubular portion 63 of the fixture, and an inward-curved end portion 64.

FIG. 5B is a schematic illustration showing a flat sheet of resilient material 65, which is cut in preparation for fabrication of fixture 60, in accordance with a preferred embodiment of the present invention. Leaves 62, 66, 68, 70, 72, 74, 76 and 78 are cut out of sheet 65 in a stairstep pattern, i.e. each leaf presents a step-like extension, as shown in the figure. The leaves are then rolled up, one after the other. The leaves are rolled about axis 30, in the direction indicated by arrow 79, so that in the closed configuration shown in FIG. 5C, the leaves will expand to the shape shown in FIG. 5A.

FIG. 5C is a schematic, sectional illustration showing fixture 60 in the closed configuration, in preparation for insertion of the fixture into the intramedullar cavity. Holding pin 56, as described above with reference to FIG. 4B, is inserted along axis 30 of fixture 60. Curved end portions 64 of leaves 62, 66, 68, 70, 72, 74, 76 and 78 are bent inward and hooked around pin 56. Fixture 60 remains in this closed configuration as long as pin 56 is in place. In the closed configuration, the device maintains a smaller external diameter than the open configuration, to facilitate insertion of the device into the bone. After insertion of the fixture in the intramedullar cavity, pin 56 is withdrawn, and the resilience of the leaves causes them to spring outward, so that fixture 60 resumes the open, larger diameter, configuration shown in FIG. 5A. In this larger diameter, bone fixation and support is provided as previously described above.

The device, as with the other devices in the application, can also expand by heating, taking advantage of the material's shape memory properties. As with the other embodiments of the invention disclosed herein, it can be used in treatment of both intramedullary and intravertebral support.

FIG. 6 is a schematic illustration of another expandable intramedullar fixture 80, comprising a balloon 82, shown here in a deflated state, in accordance with an alternative preferred embodiment of the present invention. Balloon 82 can be formed of a flexible, biocompatible plastic, for example, a sleeve of Dacron fabric, as is known in the art, sealed shut at a distal end thereof. Fixture 80 preferably includes strong, resilient longitudinal wires 84, made of biocompatible material (most preferably stainless steel), for strengthening balloon 82. Wires 84 may preferably be woven into the Dacron fabric of balloon 82, for example. Balloon 82 is connected via an inlet port 86 to an inflation tube 88.

Balloon 82 can also be constructed from metal having one extremity sealed shut, the other extremity being provided with a valve. In a metallic embodiment, balloon 82 can likewise have longitudinal wires or bars, as discussed above. In such an embodiment, the balloon can have a thin metal wall between the longitudinal wires or bars, this thin metal preferably being bent inwardly so as to reduce the balloon profile and diameter during insertion.

FIGS. 7A–7D are schematic, sectional illustrations showing the use of balloon fixture 80 in fixating fractured bone 42. As described above with respect to FIGS. 3A–3C, in the preferred embodiments, a hole 45 is first made in the end of fractured bone 42 to provide access to the bone's medulla. As shown in FIG. 7A, fixture 80 is then inserted through hole 45 into intramedullar cavity 40 using cannula 48. Although a thin hollowed out space can be created within the medulla prior to insertion of the fixture, in the preferred embodiment, insertion of the fixture 80 using cannula 48 itself creates the intermedullary space.

Preferably, inflation tube 88 is used in place of plunger 43 (shown in FIG. 3B) to push fixture 80 through the cannula 48 and position the fixture 80 within cavity 40. It is preferred that the fixture be provided with a medial longitudinal canal so as to allow insertion of the inflatable rod over a guide wire. Longitudinal wires 84 help to hold balloon 82 in a narrow, elongated profle, so as to ease the insertion of the balloon into cavity 40. After canula 48 is withdrawn from the bone, fixture 80 is left extending through a substantial portion of cavity 40, across both sides of fracture site 44, as shown in FIG. 7B.

Inflation with the non-compressible fluid is preferably accomplished with an inflator having a pressure gauge. The pressure gauge is monitored during the inflation of the fixture. When the pressure begins to rise in slope, it indicates that good alignment has been achieved of the rod within the bone's inner surface. Later, to remove the device, a hub for fixture retrieval is inserted over the proximal part of the fixture where the valve is positioned. This hub can be used to open the valve, allowing fluid to be removed so that reduction of fixture diameter can be achieved to facilitate removal.

As illustrated in FIG. 7C, after fixture 80 is inserted in cavity 40, balloon 82 is inflated via tube 88. Preferably, the balloon is first inflated with water (e.g. saline), whereupon the fixture expands to fill substantially the entire width of cavity 40. At this stage, an X-ray image of bone 42 can be produced. In the image, wires 84 and the bone are both visible, so that proper positioning of the fixture 80 can be verified.

Balloon 82 is then emptied of the saline and filled with a biocompatible, solidifying fluid which fills the balloon 82 so as to fixate the bone. Preferably, the solidifying fluid comprises a monomer material that polymerizes within the balloon, or alternatively, a two component cement, such as an epoxy. The fluid's solidification is preferably catalyzed by the increased temperature and/or humidity within the bone medulla.

As shown in FIG. 7D, after balloon 82 has been filled and the fluid has at least partly solidified, inlet port 86 is sealed shut, and tube 88 is withdrawn. Within a short time, the solidified fluid fully hardens, anchoring fixture 80 in place and fixating bone 42. Wires 84 provide additional mechanical strength to fixture 80, particularly improving the fixture's resistance to lateral, bending and shear forces. In a further embodiment, a sheath or cup can be located over the valve, after insertion, to prevent bone ingrowth within or into the valve.

As in the other preferred embodiments described above, the skin wound made for insertion of fixture 80 into bone 42 is closed and allowed to heal. Bone 42 may then be mobilized within a very short time after the bone fixation surgery.

If desired, after bone 42 has healed, fixture 80 may be removed through hole 45 or via an osteotomy elsewhere in bone 42. Preferably, at least a portion of the solidified fluid is drilled out or broken up, and the fixture is then collapsed and removed. (If, in an alternate embodiment, liquid or gel is used, they are merely suctioned or pumped out, for collapse and removal of the fixture. Alternatively, in those embodiments using a valve, the valve can merely be opened so that when the rod is pulled out of the bone through a narrow canal, the rod will be caused to reduce in diameter.)

Further preferred embodiments are shown in FIGS. 8–11. FIGS. 8 and 9 illustrate embodiments in which the balloon is designed so that only a portion is inflated with fluid. As shown in the figures, the shaded sections represent the fluid filled areas of the balloon.

As an alternative to a folded construction, the expandable bone fixation device can be formed based on a lattice configuration. Representative embodiments are shown in FIG. 10, which illustrates a series of perspective views of two embodiments of the configuration in both the small, constricted, diameter and the large, expanded, diameter. These embodiments can be inserted into the bone taking advantage of the self-expanding principle inherent to superelastic or shape memory alloys discussed above.

In the preferred embodiments of FIG. 10, the devices are each formed in a meshwork or lattice configuration. FIGS. 10(*a*) and 10(*b*) provide an illustration of a first embodiment of this lattice configuration, while FIGS. 10(*c*) and 10(*d*) provide an illustration of a second embodiment. As shown in FIGS. 10(*a*) and 10(*c*), a first, small profile state is illustrated for each of the devices in which the devices are compressed into small diameters d. This reduced diameter facilitates ease of insertion into the bone. FIGS. 10(*b*) and 10(*d*) show the respective first and second embodiments, each with increased diameters d' after expansion. After insertion into bone, the properties of the superelastic or shape memory material cause the device to expand outward into these expanded diameters.

Although of similar construction, these first and second embodiments differ in the design of their respective lattices. The first embodiment (FIGS. 10A and 10B) is contructed as a lattice which is initially in a configuration that is substantially diamond shaped, and which expands outward into a series of expanded diamonds or squares. The second embodiment is constructed as a reduced-size lattice having a series of rectangular shaped subunits, which expand outward to form a series of interconnected hexagons (sixsided polygons), like a honeycomb.

In addition to the two embodiments shown, other meshworks or lattices may also be provided. Likewise, although the embodiments shown are preferably for use in self-expanding designs, they can be constructed out of other materials to serve as expandable devices. Such expandable devices, as disclosed below, will expand from the reduced to the expanded diameter state upon application of suitable energy or force.

FIG. 11 illustrates a further preferred embodiment of the present invention. The fixator is constructed as a round or square device which can be set to two heights, H1 and H2. Rigid rods or bars 85 are hinged at points 83. By applying external force 81 on the hinge 83, the height of the device can be changed, thereby providing its expansion and fixation properties at its new height, H2 (compare FIG. 11B to FIG. 11A).

Although preferred embodiments are described herein with reference to fixation of fractured phalanx and humerus bones, intramedullar fixtures in accordance with the principles of the present invention may be produced and used in fixating substantially any of the body's long bones. Such fixtures may be used, for example, both in small bones of the hands and feet, such as the metacarpal and metatarsal bones, and in large bones, such as the femur.

The fixtures and minimally-invasive methods of bone fixation in accordance with the present invention, appropriately adapted for the anatomical features of the bone being fixated, have the advantages of minimizing operative trauma and damage to soft tissues. Furthermore, because no parts of the fixtures are left protruding through the skin, the risks of infection are reduced, and the patient is able to mobilize the broken bone more quickly than the prior art.

Treatment of Intervertebral Pathologies By Spinal Fusion

The principles set forth above may further be used to treat problems of the spine and vertebrae, such as in spinal fusion procedures. In accordance with the present invention, in order to achieve spine fusion, we optimally use three procedures:

1. An intervertebral tissue extractor thoroughly extracts the vertebral periosteum in the intervertebral space with the nucleus material. This enhances bone growth (osteosynthesis).
2. The intervertebral hollow and an intercommunicating spacer (shown e.g. in FIG. 12–13) enable bone graft interpositioning in its lumen which, together with its porous design, enables bone tissue to grow through it and enhances bone synthesis and vertebral fusion.
3. The intervertebral spacer of the elastic type, such as a Nitinol spacer, has flexible compressive characteristics so as to enable weight bearing on the interpositioned bone and to enable bone synthesis. One material which can be used is a nitinol, sponge type material (i.e. a porous nitinol).

As further discussed in the section on tissue extraction devices below, various tissue eroders and electrocautery probes are provided herein for the percutaneous removal of tissue and disc material from the intervertebral space. These devices further facilitate performing the methods of the present invention without the need for major surgery, which is currently the treatment of choice for disc ablation.

As the first step in the procedure, a syringe is inserted into the damaged disc area, with or without a stylet. Once the stylet is taken out of the syringe, it is possible to insert the intervertebral tissue erosion and extraction device through the syringe lumen. These tissue eroders "nibble" at or erode soft tissue only, including the vertebral periosteum, causing no damage to the bone itself.

Once the tissue erosion and extraction has been completed, it is possible to insert the expandable intervertebral spacer or another expandable spacer percutaneously through that same hollow syringe, as with the embodiments of the intramedullary fixation device disclosed above. The function of this spacer is to stabilize the vertebrae and to enhance bone growth up to bone fusion between the two vertebrae adjacent to the intervertebral spacer.

As shown in FIGS. 12 and 13, preferred embodiments of the intervertebral bone spacer 125 or 130 are illustrated (although the device can be used for intramedullary fixation as well). The intervertebral spacer 125 or 130 is initially inserted through the syringe in the compressed, reduced diameter form illustrated in FIG. 13B. This spacer, like the intramedullary fixation device, is initially maintained in a reduced diameter profile for insertion into the intervertebral space. This ability to percutaneously insert the spacer, due to the reduced diameter profile of the spacer, allows major surgery to be avoided, as disclosed above, and reduces the trauma and risk of infection to the patient.

Upon insertion of the intervertebral spacer 125 or 130 into the intervertebral space, the spacer uncoils to reach the expanded state shown in FIG. 13C, by virtue of its expandable properties. As with the embodiments of the inventions disclosed above, the spacer 125 or 130 is preferably made of biocompatible metal or polymer and is initially inserted through the syringe in the compressed, reduced diameter form illustrated in FIG. 13B. The spacer can also be made of materials such as annealed 316-L stainless steel, shape memory alloy (e.g. Nitinol), or a polymer such as polyurethane. In the event that annealed material is used, the spacer 125 or 130 will require the assistance of an expander to expand its diameter after insertion. This expander can be a balloon inserted through the syringe which is inflated to dilate the spacer to the diameter of the intervertebral space. Alternatively, the expander can be a mechanical expander which is inserted into the spacer lumen and which self-expands, or which is expanded using outside assistance. In the event that a self expandable material is used for the spacer, this expander can still be employed merely to assist with the expansion, if desired or needed.

As can be seen with reference to FIGS. 12 or 13C, the spacer 125 or 130 is provided with a series of pores or gaps 120 in its surface. These pores 120 (which are circular, rectangular, or any other shape) enhance vertebral stability by allowing bone growth through the pores, and eventually direct fusion between adjacent vertebrae, while the spacer is in place. Protrusions or spikes 153 can also be provided, which penetrate the bone surface and assist with fixation and stabilization of the spacer.

As further shown in FIGS. 13A and 13C, in the preferred embodiments, spacer 130 is provided with a locking mechanism such as one or more locking fingers 115 or teeth 119. This locking mechanism further maintains the expanded diameter of the intervertebral spacer 130 and retards or prevents compression of the spacer 130 back to its reduced diameter state. FIG. 13A illustrates the use of one or more locking fingers 115 in spacer 130. When spacer 130 expands, leading edge 122 of the spacer travels past and over locking fingers 115 or teeth 119. Locking fingers 115 or teeth 119 resist retrograde movement of the leading edge 122 or contraction of the spacer 130 by trapping the leading edge 122 within the "V" shaped gap of the locking finger 115, or the groove of one of the teeth 119. As a result, in response to the application of force to spacer 130 while it rests between the vertebrae, the spacer exhibits flexible compressive characteristics yet resists undue compression, due to the counteraction provided by the locking mechanism.

Accordingly, the combination of the thorough cleaning of the bone surface, the special spacer porous design with its flexible compressive characteristics, and the implanted bone graft, enables and enhances bone fusion in the intervertebral space and stabilization of vertebrae up to the point of bone fusion.

Intervertebral Disc Prosthesis

Reference is now made to FIGS. 14A and 14B, which are schematic illustrations showing a balloon prosthesis 140, for insertion in the intervertebral disc space of a patient, in accordance with a preferred embodiment of the present invention. FIG. 14A is a top view of the prosthesis, whereas FIG. 14B is a sectional view, in which the balloon is shown in an inflated state, as described below.

Balloon prosthesis 140 comprises two circular pieces of biocompatible fabric or polymer 142, preferably having a diameter approximately equal to the diameter of an intervertebral disc. Fabric 142 is preferably woven out of strong, inert, synthetic fibers, such as Dacron, Gore-Tex or other fiber materials known in the art. Alternatively or additionally, the fabric may comprise bioabsorbable material, known in the art, either by itself or, preferably, interwoven with the inert fibers. The fabric preferably has a rough weave, so that after implantation of prosthesis 140, as described below, bone ingrowth into the prosthesis is enhanced.

Further alternatively, the two pieces of fabric 142 may be replaced by any suitable biocompatible material, as long as it is flexible, elastic and strong enough to be inserted into the disc space and inflated to a sufficient pressure, as described below.

It is preferred that ground bone substance (taken, for example, from the patient's pelvic bone) be placed on the outer surface of fabric 142, before and/or after implanting prosthesis 140. Moreover, a substantial quantity of the bone substance may preferably be contained in the hollow at center 146 of the balloon. The ground substance further enhances the desired bone growth and fixation to bone.

It is also preferred that the balloon further be provided with protrusions 153 in its upper and lower surfaces so as to stick and/or penetrate up and down into the bone surface. These protrusions prevent balloon movement and achieve better stabilization of the balloon.

Although preferred embodiments are described herein with reference to the generally toroidal balloon shown in FIGS. 14A and 14B, it will be appreciated that the principles of the present invention may be applied to produce and implant balloon prosthesis of different sizes and/or shapes, such as ellipsoidal and crescent-shaped balloons, or two parallel, cylindrical, rods.

Fabric pieces 142 are sealed to one another around their outer edge 144 and at their circular center 146. As one example, heat sealing can be used, a technique which is known in the art. Preferably, one or more strong, resilient wires 152, preferably stainless steel wires, are interwoven with fabric 142 to reinforce the structure of balloon 140. Wires 152 are shown in FIGS. 14A and 14B at outer edge 144 of the balloon, where the presence of the wires is helpful in preventing rupture of the balloon along the seam between pieces 142. The wires are also useful in stiffening the balloon, to make it easier to manipulate and position within the disc space, as described below. Alternatively or additionally, such wires may be interwoven at other locations in fabric pieces 142. They can also be useful in positively locating the wire when used in conjunction with X-ray imaging.

A fluid port 148 is left open at a point along edge 144. An inflation tube 158 is fitted and sealed to port 148. When a pressurized fluid is injected through tube 158 into port 148, the fluid fills and inflates space 150 within balloon 140 to a predetermined fluid pressure.

FIG. 15 is a schematic, isometric view illustrating the implantation of prosthesis 140 into a disc space 162 intermediate two vertebrae 164 and 166, in accordance with a preferred embodiment of the present invention. Prosthesis 140 is implanted in disc space 162 to replace an injured natural disc, e.g., a disc that has been herniated. In preparation for implantation of the prosthesis, a cannula 160 is inserted percutaneously into disc space 162, in a lateral approach. Substantially all of the natural disc matter is removed from the disc space prior to implantation of the prosthesis.

In order to insert prosthesis 140 into cannula 160, the prosthesis is rolled into a narrow, elongate, generally cylindrical form, as shown in FIG. 15. The prosthesis is fed in this shape through the cannula and into now eroded out disc space 162. Preferably, inflation tube 158 is stiff enough so that it can serve to push the prosthesis through the cannula. Otherwise, other surgical probes known in the art may be used for this purpose.

It will be appreciated that the unique reduced diameter structure and flexibility of prosthesis 140, in accordance with the principles of the present invention, make it possible to implant the prosthesis through narrow cannula 40. Disc prostheses known in the art cannot be compacted in this manner nor can they be subsequently opened and inflated within disc space 162, as described below. Thus, prosthesis 140 can be implanted percutaneously, without the need for substantial skin incisions, laminectomy or dissection of large masses of muscle.

FIG. 16 is a schematic, sectional view showing vertebrae 164 and 166, seen along a coronal plane therethrough, with prosthesis 140 positioned in disc space 162 between the vertebrae. Once prosthesis 140 has been fed all the way through cannula 40 and into the disc space, the prosthesis unrolls in the open space, assuming a generally flat shape (as shown in the figure), until it is inflated. The resilience of wires 152 aids the balloon fabric in unrolling. It also stiffens the fabric to make it easier to center the prosthesis in the disc space, preferably by pushing and pulling it using tube 158 through cannula 160.

Correct placement of prosthesis 140 in disc space 162 is preferably verified by visualization of the vertebrae, disc space and prosthesis, most preferably using an open magnetic resonance imaging (MRI) system. Alternatively, X-ray imaging may be used to observe the position of wires 152 relative to vertebrae 164 and 166. Further alternatively or additionally, a narrow endoscope, as is known in the art, may be inserted into or adjacent to disk space 162 to visually observe the prosthesis.

In a preferred embodiment of the present invention, after insertion of prosthesis 140 as shown in FIG. 16, the prosthesis is inflated with saline, so that it assumes the form shown in FIG. 14B. Inflating the prosthesis allows it to be visualized in substantially the shape and position that it will have when filled with solidifying fluid, as described below. If the prosthesis is seen to be incorrectly positioned, it can easily be deflated, repositioned and then reinflated. After correct positioning is verified, the saline is removed and the prosthesis deflates.

Once prosthesis 140 is suitably positioned in disc space 162, a biocompatible solidifying fluid is injected through tube 158 and port 148, to inflate the prosthesis. Preferably, the solidifying fluid comprises a bone epoxy, known in the art, such as DuPuy Orthopedic Bone Cement, produced by the DuPuy Company, England. Alternatively, the solidifying fluid may comprise a polymerizing monomer.

Prosthesis 140 is inflated to such pressure as is necessary to maintain an anatomically correct spacing between vertebrae 164 and 166. Because of the elasticity of fabric pieces 142 that form the balloon and the equalization of the pressure of the fluid throughout space 150 (as seen in FIG. 14), the balloon will tend naturally to maintain a generally uniform pressure on the surfaces of vertebrae 164 and 166 that adjoin disc space 162 and to hold the vertebrae in an anatomically correct mutual orientation. Preferably, vertebrae 164 and 166, along with prosthesis 140 and surrounding structures, are imaged, most preferably using MRI, as described above, to verify that the spacing and orientation of the vertebrae are correct.

When the fluid has solidified sufficiently, port 148 is sealed and tube 158 is removed, preferably by twisting and pulling tube 158 back through cannula 160.

FIGS. 17A and 17B are coronal and axial sectional views, respectively, showing prosthesis 140 inserted and inflated within disc space 162. The prosthesis has been inflated with solidifying fluid 170, and tube 158 has been detached and removed, as described above. Vertebrae 164 and 166 remain substantially intact, including lamina 172, thereof.

Following the implantation of prosthesis 140, as shown in FIGS. 17A and 17B, vertebrae 164 and 166 will grow into disc space 162, around and through the prosthesis. Preferably, as described above, ground bone is placed on the outer surfaces of prosthesis 140, and particularly in the hollow at center 146 thereof, in order to aid this bone growth. Ultimately, the growth of vertebrae 164 and 166 will cause them to fuse together, so that the bones are permanently stabilized and protected from any further injury.

Although in the preferred embodiments described above with reference to FIGS. 14–17, a single prosthesis, comparable in size to the natural intervertebral disc, is implanted in disc space 162, in other preferred embodiments of the present invention, two or more smaller prostheses may be implanted side-by-side in the disc space.

Furthermore, although in the above-described preferred embodiment, prosthesis 140 is implanted percutaneously in a lateral approach, it will be appreciated that inflatable disc prostheses in accordance with the principles of the present invention may also be implanted using other surgical techniques known in the art, such as open and laparoscopic surgical procedures with an anterior or posterior approach.

Additional preferred embodiments of the present invention are shown in FIGS. 18A–18C. These embodiments present flat annular top and bottom walls, like a washer, in contrast to the donut (toroidal) shape shown in FIGS. 14–17. Further preferred embodiments are also described below in the following section regarding metal balloons for intramedullar fixation and disc prostheses.

Metal Balloons for Intramedullar Fixation and Disc Prosthesis

As described above, in accordance with the present inventions, a small opening is made from outside a bone to accommodate insertion of a device percutaneously into the bone (whether it be long or small bone); or, to replace a disc, a hole is made in the intervertebral space. In some of the preferred embodiments of the invention, the device includes a metallic balloon.

In the preferred embodiments, the balloon is made from thin metal such as Titanium, Tantalum, Stainless Steel (e.g. S.S. 316L), Platinum, another medical grade metal, or so forth. The balloon is preferably constructed with a balloon wall thickness between 10 and 300 microns, although wall thicknesses which are greater or less than these dimensions are possible, as well.

The balloon can be constructed with several metal strings or rods to provide the balloon with greater strength against axial, bending and rotational forces, and to provide the balloon with greater rigidity that eases its manipulation and insertion into the patient. The rods can be connected to the exterior or interior surface of the balloon (e.g. by soldering, milling or as a part of the balloon). For example, to produce the the metal balloon and the rods they could all be annealed or could all be cold worked. Alternatively, the rods could be cold worked, while the balloon itself is annealed to allow easier expansion after insertion within the bone. This can be done by producing a one piece cold worked rod and annealing afterwards only the thin wall part of the metal balloon. The balloon extremities can be manufactured by soldering, spot welding, laser welding or any other suitable way of connecting the metal cone to each extremity of the device.

The outer surface of the balloon may be abrasive or roughened with protruding edges engaging the bone surface to anchor the fixture firmly in place and prevent sliding or rotation of the parts of the broken bone in the intramedullar embodiments, or, likewise provide non-movement in the intervertebral embodiments. This system has the advantage of not requiring or using interlocking screws in intramedullar nailing.

Additionally, or alternatively, the balloon can comprise a biocompatible polymer. Additionally or alternatively, the balloon can comprise an outer thin surface of metal as described above and an inner surface of biocompatible plastic, polymer or fabric.

Once the balloon has been inserted into its proper place within the bone or adjacent to the vertebrae, it is then inflated with a biocompatible material. In the preferred embodiments, a liquid is used as the inflation fluid in intramedullary fixation, and a biocompatible solidifying fluid is used as a disc prosthesis. As liquids for intramedullary fixation, water, gel or air are preferred. As a further alternative, however, a solidifying fluid can be used, if desired.

In alternative embodiments of the invention, the inflation fluid (either for the intramedullar nail or the disc prosthesis) is a filler material which is itself capable of expansion. This filler material is preferably capable of changing its volume or stiffness in response to an external stimulus. For example, the external stimulus can be a magnetic field, an electric field, radiation and/or temperature. Rheological materials, polyelectrolyte gels or other suitable expandable materials which change their volume or stiffness in response to external stimuli can be used as the filler material.

For disc prosthesis, a biocompatible solidifying fluid or other noncompressible fluid is used in the preferred embodiments. Preferably, this solidifying fluid or noncompressible fluid comprises a monomer material that polymerizes within the balloon, or alternatively, a two-component cement, such as epoxy. This provides a prosthesis with sufficient strength to replace the disc.

This inflation fluid is placed in communication with the lumen of the balloon, while also being under pressure from an external source, causing the balloon to expand radially outward to fixate the bone. The balloon is then sealed, e.g. by using a valve, and the external fluid source is disconnected. In the valve embodiments, it is preferred that a protective cup be provided over the valve to shield and protect the valve from bone ingrowth.

In the embodiments using a solidifying fluid, the disc prosthesis becomes extremely strong and can replace the disc. This balloon can also be provided with one or more tunnels or holes between surfaces that allow the vertebral bone surfaces to contact each other between two adjacent vertebrae, thereby enabling those two vertebrae to undergo fusion. In addition, the outside surface of the metal balloon is stronger than the vertebrae, which keeps the vertebrae from eroding. The outside surface of the metal balloon can also be abrasive or roughened, and be provided with protruding edges to engage the vertebrae and anchor the fixture firmly in place, preventing sliding or rotation.

Additionally or alternatively, the balloon can comprises a biocompatible plastic which is of sufficient strength that it is stronger than the vertebrae. Additionally or alternatively, the balloon comprises an outside surface of metal as described above and an inner surface of biocompatible plastic or fabric.

In the case of the intramedullary device, once the bone has healed, the balloon can be deflated by opening the valve and removing the liquid, thereby easing the device's removal. In the case of the intervertebral disc prosthesis, the prosthesis may be left in place permanently. In both cases, using fluid allows the possibility of subsequent open or remote inflation of the prosthesis, thereby reducing or eliminating bone to implant loosening, and relative movement between the implant and the bone.

FIGS. 28–31 illustrate some preferred embodiments of the present invention. These embodiments are useful with respect to the intramedullary nail, and the balloon embodiments of the nail, in particular, although features of these embodiments can also be used in conjunction with self-expanding or expandable devices and/or in conjunction with the other intervertebral devices and prostheses disclosed herein. Thus, the valve, fixation elements, etc. can also be used with the other inventions disclosed in the present disclosure.

FIG. 28 illustrates an additional preferred embodiment of the intramedullary nail or fixture of the present inventions. As shown in the figures, it is preferred that the nail be constructed having longitudinal, outwardly extending, bars 300. FIG. 28B is a cross sectional view illustrating the protuberance of longitudinal bars 300 above the surface of intramedullary nail 310. These longitudinal bars 300 may be placed upon a portion of the length of intramedullary nail 310, although it is preferred that they extend along all, or substantially all, of the length of the intramedullary nailing device. In the preferred embodiment, as shown in the figure, four longitudinal bars are provided, located at 90 degree intervals around the nail's circumference. Alternatively, other numbers of longitudinal bars can be provided as well.

Longitudinal bars 300 act as fixational elements, improving the function of the device and facilitating bone healing. When the intramedullar nail is inflated, the longitudinal bars or fixational elements 300 are pressed against the inner surface of the bone cortex, preventing rotational movement between the broken parts of the bone and preventing bending. The addition of these fixational elements presents an advantage over standard intramedullar nails as no interlocking is needed due to the fact that the longitudinal rods prevent rotation. This further stabilizes the bone, and facilitates the healing process. These longitudinal bars or fixational elements 300 can be provided to various embodiments of the present invention, whether the self expandable, balloon expandable, or balloon embodiments, disclosed herein.

FIG. 29 illustrates additional aspects of a preferred embodiment of the intramedullar fixture disclosed herein. As shown in the figure, in preferred embodiments of the invention, a metal balloon or fixture 320 is utilized having a pipe or body 321 and a distal end cover 323. Metal balloon or fixture 320 is further provided with a valve 318 located at proximal tip 330 of the fixture for controlling the passage of fluid into and out of fixture 320. Valve 318 includes ventilation pin 325, O-ring 326, and spring 327 housed within a head cover 322, and terminating in a head cap 328. Head cover 322 and head cap 328 shield valve 318, preventing bone growth into the valve.

In a preferred embodiment, a high pressure fluid (e.g. saline) is first inserted or pumped into the intramedullar fixture through valve 318. Pumping of the saline into the balloon through the valve causes fixture 320 to expand in diameter, as shown in comparison of FIG. 29B to FIG. 29C. The valve prevents fluid from escaping the intramedullar fixture, maintaining the fixture in the expanded state for the length of time needed. If desired, the fixture can be subsequently deflated using valve 318 to release fluid or saline from the fixture.

A further embodiment of the invention is illustrated in FIG. 29D. The invention is illustrated as located within a bone 313. The fixture is provided with a tubular element 311 for location in the vicinity of the bone fracture. Element 311 is of a fixed diameter less than the diameter of inflated fixture segments 315. The diameter of element 311 is fixed such that upon radial expansion of the fixture, element 311 prevents or restrains expansion of the fixture so that it cannot contact the inner bone surface. Thus, although segments 315 expand to a diameter which contacts the inner surface of the bone, element 311 prevents the fixture surrounded by the element from achieving the degree of expansion achieved by the remainder of the fixture. The device, for example, can be provided with a ring for restraining expansion of in that area. This embodiment is particularly useful to prevent "butterfly fractures", or complications in fractures with multiple bone fragments.

An embodiment of the intramedullar nail of the present invention is disclosed in FIG. 30A. FIG. 30A consists of two cross sectional views of a fixture embodiment, both before and after expansion, these views being superimposed on each other (for appreciation of relative constricted and expanded diameters). In this embodiment of the invention, the constricted intramedullar nail includes a curved or undulated surface, preferably having longitudinal bars 300 located thereon. It is preferred that intramedullar fixture, before expansion, have its surface be curved or folded inward to form a series of connected bulbous sections 336. In the preferred embodiment, the bulbous sections form a clover like configuration in the compressed state, as shown in the four leaf clover configuration illustrated in FIG. 30A.

As shown in FIG. 30A, in the compressed configuration or state 332, intramedular nail 330 maintains a compressed diameter $D_1$. Compressed diameter $D_1$ is a small diameter such that the intramedullar nail is suitable for insertion into the bone through a small hole in the bone or through a syringe, as discussed above. In contrast, in the expanded configuration or state 334, the intramedular nail 330 is maintained within the bone at an expanded diameter $D_2$. Expanded diameter $D_2$ is a larger diameter, measured from the outside surface of longitudinal bar 301 to the outside surface of opposing longitudinal bar 302, this diameter being sufficient such that the longitudinal bars are pressed up against the inner wall of the desired bone. The figure, although not to scale, shows both the compressed and expanded states of the fixture superimposed on each other, illustrating the substantial increase of diameter achieved by inflation of the fixture from the compressed to the expanded state.

FIG. 30B is a further embodiment of the invention, illustrated in the same manner as in FIG. 30A. In this embodiment, one or more hairpin loops or arcs 337 are provided between longitudinal bars 300. In the embodiment shown, four longitudinal bars 300 are provided, each at 90 degrees to each other, with one hairpin loop 337 centrally located between and connecting each adjacent pair of longitudinal bars. One or more or no hairpin loops can be provided between any or all of the pairs of adjacent longitudinal bars, if desired.

As shown in FIGS. 31A and 31B, in preferred embodiments, the intramedullar nail can also be provided with a medial longitudinal canal, bore or tunnel 344. This canal 344 facilitates the insertion of the nail into the bone, allowing the insertion procedure to be performed using a guide wire. The medial canal 344 is threaded over the guide wire to allow the fixture to be easily guided into the appropriate position during insertion into the bone, and to allow the guide wire to be pulled out once positioning has been completed.

Particularly in the embodiments having a valve, a retrieval mechanism can be provided which is mounted on the tip of the implanted nail to assist in withdrawal of the nail from the bone. Upon mounting the retrieval device on the tip of the valve, the valve can be opened, releasing the high pressure within the nail and thereby allowing the diameter to decrease in preparation for removal.

Remotely Activated Prosthesis

In accordance with the present invention, prostheses are also herein provided which can be remotely activated, from outside the body, after they have been implanted within the body. The invention is particularly suited for orthopedic applications. The remote activation is used to expand or increase the size of the prosthesis (e.g. its length and/or diameter) to eliminate the loosening effects which develop over time between fixture and bone, and which have posed a problem in the prior art.

As shown in FIGS. 32 and 33, an inflatable member 400 is provided, having a chamber 401 preferably made of metal or polymer. The chamber 401 has an inner lumen 402 and is of a shape and material allowing the chamber 401 to expand in size, whether length, diameter, and/or volume 403. In the figure, the walls of the chamber 401 are shown in a curved or undulated construction, which allows the chamber 401 to be initially compressed into a first, small length state, and then later expanded into a second, larger length state, in which the curves have been strengthened. Chamber 401 has an inner support 404, a screw 408 and fixed nut 405 at the inflatable member's proximal end, and a magnet 406 attached to either the nut or the shaft. The fixed nut 405 is preferably secured to the inside of chamber 401. The magnet 406 is preferably cylindrical, and is rotatable on magnet support 404 along with screw 408 which mates with the threads of nut 405. An external unit 407 which produces a magnetic field is magnetically coupled to the implanted magnet 406. The magnetic field produced by the external unit causes rotation of the magnet 406 within the inflatable member's inner chamber, rotating the magnet and screw with respect to the nut so that the magnet and screw move distally with respect to the nut. This causes the magnet 406, which remains in contact with the chamber support 404 to press the distal wall of the chamber outward. Likewise, due to the rotation of the screw within fixed nut 405, the rotation of the magnet causes the fixed nut to move in the opposite direction, proximally, to force the proximal walls of the chamber outward, as well. Thus, the rotation exerts a force on the inside of the chamber's walls, to force the proximal and distal walls apart, such that the walls of the chamber 401 begin to straighten from their curved shape to a more straight configuration, causing a lengthening of the chamber 401.

The external field can be applied for the duration desired, causing partial lengthening, or complete lengthening of the inflatable member to its fully extended diameter. The external unit 407 can be an MRI machine, or a rotating magnet or member which produces a magnetic field. Examples of internal magnets which are magnetically coupled to external units are disclosed in U.S. patent application Ser. No. 08/236,448, filed May 2, 1994 and entitled, "Magnetically-Coupled Implantable Medical Devices", and in International Patent Application Serial Number WO 97/41799, the disclosures of which are fully incorporated herein by reference.

FIG. 33 illustrates the inflatable member when maintained in an almost fully inflated position relative to the compressed condition. As can be seen from the figure, magnet 406 has rotated such that screw 408 within nut 405 has rotated until the majority of the screw has exited the nut 405. The external magnetic field created using remote activator 407 caused rotation of magnet 406 such that magnet 406 exerted a force on chamber shaft 404 and rotated the screw within fixed nut 405. This exerted an outward force on the internal walls of the inflatable member which extended the length of the walls 409 to a straighter configuration, thereby lengthening the inflatable member.

FIG. 34 is a schematic view showing the inflatable device of FIGS. 32 and 33 when installed in a nail 418. The figure illustrates a comparison of the inflatable member in both compressed and expanded configurations, while located within the intramedullar nail 418. The inflatable member within the upper intramedullar nail is shown in the compressed position, while the inflatable member within the lower intramedullar nail is shown in the expanded position. The two views are, therefore, "before" and "after" illustrations of the same inflatable member, before and after expansion. As shown in the figure, expansion of the inflatable member (by use of the external magnetic field, as described above) causes it to increase in length from length $L_1$ to length $L_2$. This expansion of the member while within the intramedular nail, itself having incompressible fluid, causes the nail to expand in diameter from diameter $D_1$ to diameter $D_2$, while keeping the nail length constant. Although an intramedullar nail is shown in the figure, the inflatable member can be used for any fixture within the body. The inflatable member is particularly suited for bone related applications, such as an intervertebral cage or prosthesis, a hip prosthesis, a dental implant, or so forth.

FIG. 35 illustrates the loosening pathology which is currently a problem in the art. As shown in the figure, over the course of time a distance can develop between the inner surface of the bone cortex and the outer surface of the intramedullary nail, resulting in loosening of a nail, and a substantial or complete reduction in the nail's effectiveness.

In accordance with the present invention, FIG. 36 shows the results of remote expansion of the nail volume and diameter. Expansion of the nail diameter, as shown in FIG. 36, eliminates the problem shown in FIG. 35. The expanded diameter intramedullar nail more snugly fits against the bone, eliminating the loosening problem of the prior art. This eliminates the need, which was present in the prior art, to perform an additional surgical operation to tighten up the loosened fixture.

In accordance with a further embodiment, FIG. 37 illustrates a fixture or prosthesis 430 having implanted inflatable member 431, substantially like that described and shown in FIGS. 32 and 33. Inflatable member 431 has a rotatable magnet 432, and any type of gear mechanism 433 which enables changes in the chamber volume of the inflatable member by rotation of an activator, preferably external.

As shown in the figure, it is preferred that the prosthesis further be provided with a pressure gauge 435 having a radioopaque, readable dial 436. Radioopaque dial 436 has a scale 437 and an indicator arrow 435 which together illustrate the pressure within prosthesis 430, and thereby illustrates the level of expansion and relative diameter of the prosthesis. Radioopaque dial 436 with scale 437 and arrow 435 are readable using an X-ray machine. In this manner, the relative diameter of the prosthesis 430 can be determined after implantation of the prosthesis in the bone, without the need for a surgical or an invasive procedure. By taking an X-ray of the bone, the physician can determine the relative diameter of the prosthesis in the bone. The physician can then activate the external unit to expand the prosthesis and subsequently (or simultaneously) check (or monitor) the expansion of the prosthesis by taking another X-ray and checking the reading on the radioopaque dial 436.

Tissue Erosion and Extraction Devices

As discussed above, during implantation of the prostheses of the present invention, tissue extraction and erosion is often desirable and/or necessary. Accordingly, a variety of suitable tissue extraction devices are provided for use during implantation of the prosthesis, in accordance with the present inventions.

Tissue Eroders

Reference is now made to FIG. 20, which depicts a spinning intervertebral disc tissue extraction device, in accordance with the present inventions. As discussed above, the intervertebral disc tissue extraction devices provided herein have the major advantage of allowing a percutaneous procedure, which avoids the major surgery that is currently the treatment for disc ablation.

As described above, in the first step of the inventive procedure, a syringe is inserted into the damaged disc area, with or without a stylet. Once the stylet is taken out of the syringe, it is possible to insert the intervertebral tissue eroder and extractor through the lumen of the syringe.

As shown more fully in conjunction with the attached figures, several preferred embodiments for tissue eroders are provided herein.

In the case of the design shown in FIG. 20A, the eroder 190 is a tube having a series of radial, exterior directed and rotatable brushes 182 (about the longitudinal axis) to erode the desired material. The material it erodes is sucked out of the patient by a vacuum machine, and is preferably sucked out through the tissue eroder's shaft 183. This aspect of the device can be situated in or connected to the inner part of the intervertebral tissue eroder shaft, or at any point between the spine and the syringe lumen. A spinning shaft 183 can be used to provide suction, if desired. This tissue eroder 190, as with the other embodiments to be described, nibbles at or erodes soft tissue only, including the vertebral periosteum, causing no damage to the bone itself.

In the case of FIG. 20B, the eroder is also brush-like, although here the material it erodes is removed by means of an inner screw 185 inside or outside the tissue extractor's rotating shaft. Inner screw 185 spins in relation to the inner lumen of the tube 181 drawing the eroded tissue remains away from the cutting site and taking them out of the body.

FIG. 20C shows another design of the intervertebral tissue eroder, which works according to the principle employed in a flexible wire grass trimmer. The length of the wire in the intervertebral tissue eroders 194, 196 and 198 of FIGS. 20C–E, respectively, is adjustable during the procedure, thus enabling precise control and gradual widening of the tissue erosion or eradication diameter, until reaching the bone. In FIG. 20C, the wire 187, which whips to cut tissue, is unadorned or plain. In FIG. 20D, an orb 189 with sharp edges is attached to the end of the wire 188. That orb 189 can also be made of the wire-material itself (for example, it can be an extension of the wire material formed by heating and melting of its tip), or it can be made of another, harder material, such as a suitable metal, for example. In the preferred embodiment, the orb 189 has a spherical or sphere-like design. The orb operates much like a miniaturized medieval mace on a chain.

FIGS. 20D–E show two different ways of holding the orb 189 at the tip of the wire. In FIG. 20D, the orb 189 is attached at the end of the wire 188 and preferably has a hole into which the wire passes and the orb crimped thereon. In FIG. 20E, the orb has a through bore, through which the wire is threaded. The orb is then like a bead on wire 188 or like a bead on a sling.

All of the above-mentioned rotating wires have adjustable lengths. The lengths are adjustable by pulling or releasing the wire within the rotating shaft 193. To remove the eroded tissue when using these devices, either a vacuum or screw tissue extractor can be concurrently employed.

Electrocautery Probes

Reference is now made to FIG. 23, which is a sectional view of an electro-surgical probe 220 in accordance with a preferred embodiment of the present invention. Probe 220 comprises an elongate shaft 221 having an outer surface 222. A wire 242 runs along the inside of probe 220, within a lumen 240 therein, from proximal end 227 of probe 220 to an opening 228 at its distal end 226. An arc-shaped loop 224 formed at the distal end of wire 242 is used for surgical resection of body tissue. Loop 224 is a lateral portion of wire 242, which extends from opening 228 to a point 248 where wire 242 is fixed within distal end 226.

Wire 242 is connected at its proximal end to an electro-surgical power source 219. Radio frequency currents of suitable power and frequency, as are known in the art, are passed from the power source through wire 242 to tissue adjacent the loop 224 (which is the outside extension of wire 242), causing resection of the tissue. Except for loop 224, wire 242 is generally situated within probe 220, which preferably comprises an electrically and/or heat-isolating material, which prevents unintended damage to human tissue.

A control handle 246 at proximal end 227 of probe 220 allows a surgeon to adjust the length of wire 242 within the probe and consequently the size of cutting loop 224. Preferably, a control wheel 247 within handle 246 allows easy adjustment of the size of loop 224. By pulling on wire 242 proximally, the size of loop 224 decreases, and when wire 242 is pushed distally the size of cutting loop 224 increases.

Preferably, an arc-shaped recess 244 is located within probe 220 at opening 228, so that when the size of loop 224 is minimized the loop does not protrude beyond the radial perimeter of probe 220. Further preferably, a suction lumen 234 runs along probe 220, allowing suction of smoke and particles from the resection area. Additionally, other functional elements, not shown in the figures, may be incorporated with probe 220, for example, a visualization device, an illumination device, a deflection mechanism, insufflation and irrigation channels, etc., all as are known in the art.

FIG. 24 illustrates an electro-surgical probe assembly 250, in accordance with another preferred embodiment of the present invention. Assembly 250 comprises a probe 280, contained in an outer sleeve 285, which is used to guide probe 280 to the resection location and to isolate it from the patient's body.

A wire 242 runs within probe 280, and forms an exterior loop 224 at its distal end as in probe 220, shown in FIG. 23. Radio frequency currents are passed through wire 242 from an electrosurgical power source 219, as described above.

Sleeve 285 comprises a suitable material to insulate probe 280 from the patient's body. At its distal end, sleeve 285 has a window 290 which allows wire loop 224 to contact the patient's body. Preferably, window 290 is sufficiently wide with respect to a longitudinal axis of sleeve 285, to allow side-to-side motion of loop 224 within the window. For example, an angular extent of approximately 180 degrees can be provided. The diameter of sleeve 285 is larger than the diameter of probe 280, so as to leave a space 295 through which water may be introduced to the resection area in the patient's body, and through which suction is applied to remove water, smoke and resected particles.

Preferably, probe 280 and sleeve 285 are coupled at a handle 292, by means of which the rotational orientation of probe 280 relative to sleeve 285 can be varied, up to the angular extent of window 290. Further preferably, assembly 250 includes an angular loop adjustment mechanism whereby the size of wire loop 224 is dependent on the orientation of probe 280 relative to sleeve 285. Preferably, probe 280 is connected to sleeve 285 via a linkage as is known in the art. The linkage preferably includes an eccentric gear or cam which sets the size of wire loop 224. Alternatively, an electronic processor automatically controls the size of loop 224 according to preprogrammed settings, responsive to the relative orientation of probe 280. Although the present electrocautery probes are described herein as preferred embodiments with respect to bone and intramedullary applications, these probes may be used in other procedures, as well.

FIGS. 25A–25D illustrate a TURP procedure, using a preferred embodiment of the present invention. As shown in FIG. 25A, the electrosurgical probe is inserted through urethra 300 so that distal end 226 thereof is at the distal end 304 of prostatic urethra 308. During insertion of probe 220, wire 242 (See FIG. 23) is preferably drawn in proximally, so that loop 224 is of minimal size and does not protrude from recess 244. When loop 224 is positioned adjacent to distal end 304, the power source is activated. Loop 224 is enlarged until it touches the inner surface of prostatic urethra 308, and probe 220 is rotated around its axis 314, in a direction described by an arrow 316, so as to evenly resect tissue around the circumference of a sector 318 of the urethra.

As loop 224 resects the tissue, the lumen of sector 318 enlarges, as shown in FIG. 25B. Loop 224 is enlarged again by the user to touch the circumference, and the process of resection is repeated. The process is continued until prostate gland 320 has been sufficiently resected in sector 318.

Once the prostate gland 320 has been resected in sector 318, loop 224 is made smaller, and probe 220 is pulled back to a second sector 330, preferably adjacent to sector 324, as shown in FIG. 25C. At this sector, the process is repeated, i.e., the loop is gradually enlarged and the prostate gland gradually resected. This process continues, until all of prostate gland 320 has been resected sufficiently, as shown in FIG. 25D.

It will be appreciated that in the procedure illustrated in FIGS. 25A–25D, probe 220 is preferably moved proximally toward urethral sphincter 344 only once. It is therefore relatively easy to take precautions to prevent loop 224 from touching urethral sphincter 344. Such precautions may include keeping loop 224 totally within recess 244 and/or deactivating the power source every time probe 220 is pulled proximally, until it is established in a safety check that the probe is properly positioned.

It will further be appreciated that the above described procedure may be performed in the opposite direction, that is, beginning at proximal end 332 of prostate gland 320 and moving toward distal end 304. In this case, the safety check is performed at the beginning of the process.

FIG. 26 illustrates a diskectomy procedure in accordance with a preferred embodiment of the present invention. A herniated disc 365 is located between an upper vertebra 372 and a lower vertebra 374. Upper vertebra 372 has a vertebral body 376 from which a lamina 378 extends in a posterior direction. The spinal cord (not shown) runs through a vertebral foremen 380 which is surrounded by lamina 378. Disc 365 or herniated tissue from its nucleus exerts pressure on nerves associated with the spinal cord, causing back pains. In order to alleviate these pains, at least a portion of the herniated tissue is resected. Subsequently a prosthesis may be inserted to replace the removed disc material and maintain vertebrae 372 and 374 in a defined mutual spacing.

In the procedure shown in FIG. 26, probe assembly 150 is brought into proximity with disc 365, preferably in a lateral approach through a small incision in the patient's side, as described in U.S. Pat. Nos. 5,285,795 and RE33258, which are incorporated herein by reference. Preferably, probe 280 (see, FIGS. 27A and 27B) is introduced into the disc space through sleeve 285, as shown in the figure. Thus, probe 280 can be removed and reinserted into the disc several times, if necessary, without reestablishing the insertion path. In addition, several tools may be inserted simultaneously, and/or sequentially without having to reestablish the insertion path.

Alternatively, probe 280 is inserted in a posterior approach as described, for example in PCT publication WO 96/11643, which is also incorporated herein by reference.

During the procedure, the position of wire loop 224 is preferably ascertained using an imaging system, preferably fluoroscopy, ultrasound or magnetic resonance imaging (MRI), as is known in the art. Alternatively or additionally, probe 280 is visualized using an endoscope, inserted into the patient's body to the vicinity of herniated disc 365. Once wire 224 is in place, power source 219 is activated.

During resection of the disc tissue, suction is preferably applied through space 295 (See FIG. 24), in order to remove smoke and other tissue particles. During the resection process, probe 280 is preferably rotated, and wire loop 224 successively enlarged and reduced in size, allowing the probe to be maneuvered easily into corners in which there is herniated tissue, while avoiding contact with the spinal cord and nerves.

Preferably, the size of loop 224 automatically adjusts according to the orientation of probe 280, as described above, wherein when probe 280 faces up or down, as in FIG. 27A, loop 224 remains small, while loop 224 is enlarged when probe 280 faces sideways, as shown in FIG. 27B.

Generally, it is desired to resect tissue from the nucleus of disc 365 without substantially resecting the annulus of the disc. Therefore, probe assembly 280 is preferably inserted into disc 365 through a hole cut in the annulus of disc 365, as described, for example, in the above-mentioned PCT publication WO 96/11643. The duration of the procedure, and its RF power level are chosen according to the amount of tissue to be resected.

Diskectomy in accordance with the present invention is advantageous as a preparatory step for other disc-related procedures, such as artificial disc nucleus implantation. The present invention provides cleaner disc space and vertebral bone surfaces than the prior art, and encourages quick vertebral bone growth around the prosthetic disc.

In summary, the above descriptions of the present invention describe minimally invasive insertion of intramedullary and intervertebral fixation devices, intervertebral bone spacers and supporters, intervertebral disc prostheses, tissue eroders, electrocautery probes, and methods of treatment. It must be understood that, although preferred embodiments are described, the embodiments of the present inventions are directed to expandable fixation and prosthesis devices which expand either spontaneously or by an expander inserted through its lumen to an expansion level that enables percutaneous insertion of the bone fixator.

Having described the inventions with regard to specific embodiments, it is to be understood that the description is not meant as a limitation since further variations or modifications may be apparent or may suggest themselves to those skilled in the art. It is intended that the present application cover all variations and modifications of the inventions as fall within the scope of the claims.

What is claimed is:

1. A medical device for treatment of broken bones having an intramedullary cavity, the bone being provided with a bore formed through the exterior surface of the bone and extending into the intramedullary cavity, comprising:
    a bone fixture for insertion through the bore of the bone and into the intramedullary cavity, said bone fixture comprising a diameter-expandable, metallic balloon tube having an exterior circumferential surface, said tube having a reduced first diameter for insertion through the bore and into the intramedullary cavity and a second expanded diameter, wherein when fluid is introduced into said bone fixture it radially increases in diameter from said reduced first diameter to said second expanded diameter, at least a portion of said exterior circumferential surface coming into contact with a portion of the side wall of said intramedullary cavity.

2. A medical device as claimed in claim 1, wherein said metallic balloon tube is manufactured of a material selected from the group comprising: titanium, stainless steel, SS316, and Nitinol.

3. A medical device as claimed in claim 1, wherein said reduced first diameter is sufficiently small such that said bone fixture can be inserted into the bore of the bone through a syringe.

4. A medical device as claimed in claim 1, wherein said device is basically cylindrical when expanded to said second expanded diameter.

5. A medical treatment device as claimed in claim 1, wherein said bone fixture is sized for treatment of a broken bone selected from the group comprising: the hand, the foot, the leg, and the arm.

6. A medical device as claimed in claim 1, wherein said device further comprises a restraining means for restraining radial expansion of a portion of said device, when said device expands from said reduced first diameter to said expanded second diameter.

7. A medical device as claimed in claim 1, wherein said bone fixture increases in diameter by at least 40% when said fixture increases from said reduced first diameter to said expanded second diameter.

8. A medical device as claimed in claim 1 wherein said bone fixture will expand in diameter from said reduced first diameter to said expanded second diameter when fluid is supplied to the interior of said device.

9. A medical device as claimed in claim 8, wherein said bone fixture is supplied with a valve, at least allowing for one-way fluid flow, for selective entry of the fluid into the interior of said device.

10. A medical device as claimed in claim 9, wherein said valve is bi-directional.

11. A medical device as claimed in claim 1 further comprising at least one rib longitudinally extending along the exterior circumferential surface of said bone fixture.

12. A medical device as claimed in claim 1 wherein at least two ribs longitudinally extend along the exterior circumferential surface of said bone fixture.

13. A medical device as claimed in claim 12 wherein said ribs define wall web portions therebetween and said wall web portions are folded upon themselves prior to expansion of said bone fixture.

14. A medical device as claimed in claim 1 further comprising four ribs longitudinally extending along the exterior circumferential surface of said bone fixture.

15. A medical device as claimed in claim 13, wherein said wall web portions are initially, pre-expansion, folded into individual bulbous sections, said sections being approximately S-shaped.

16. A medical device as claimed in claim 13, wherein said device comprises four of said longitudinal ribs and wherein said wall web portions are initially, pre-expansion, folded into individual bulbous sections, said bulbous sections being approximately S-shaped.

17. A medical device as claimed in claim 13, wherein each of said wall web portions are folded, pre-expansion, into a hairpin-like loop.

18. A medical device as claimed in claim 13, wherein said device comprises four of said longitudinal ribs and wherein each of said wall web portions are curved, pre-expansion, into a hairpin-like loop.

19. A medical device as claimed in claim 11, wherein said reduced first diameter is sufficiently small such that said bone fixture can be inserted into the bone through a syringe.

20. A medical treatment device as claimed in claim 11, wherein said bone fixture is sized for treatment of a broken bone selected from the group comprising: the hand, the foot, the leg, and the arm.

21. A medical device as claimed in claim 11, wherein said device further comprises a restraining element for restraining radial expansion of a portion of said device, when said device expands from said reduced first diameter to said expanded second diameter.

22. A medical treatment device as claimed in claim 11, wherein said bone fixture increases in diameter by at least 40% when said fixture increases from said reduced first diameter to said expanded second diameter.

23. A medical device as claimed in claim 11, wherein said bone fixture will expand in diameter from said reduced first diameter to said expanded second diameter when fluid is supplied to the interior of said device.

24. A medical device as claimed in claim 23, wherein said bone fixture is supplied with a valve, at least allowing for one-way fluid flow, for selective entry of the fluid into the interior of said device.

25. A medical device as claimed in claim 23, wherein said valve is bi-directional.

26. A medical device as claimed in claim 23 wherein said bone fixture is in the basic shape of a cylinder tapered on at least one end.

27. A medical device as claimed in claim 11, wherein said metallic tube is manufactured of a material selected from the group comprising: titanium, stainless steel, SS316, and Nitinol.

* * * * *